(12) United States Patent
Schraga

(10) Patent No.: US 8,971,982 B2
(45) Date of Patent: *Mar. 3, 2015

(54) CARTRIDGE WITH LANCETS AND TESTING DEVICE USING THE CARTRIDGE

(75) Inventor: Steven Schraga, Surfside, FL (US)

(73) Assignee: Stat Medical Devices, Inc., North Miami Beach, FL (US)

( * ) Notice: Subject to any disclaimer, the term of this patent is extended or adjusted under 35 U.S.C. 154(b) by 1146 days.

This patent is subject to a terminal disclaimer.

(21) Appl. No.: 11/073,736

(22) Filed: Mar. 8, 2005

(65) Prior Publication Data

US 2006/0157362 A1    Jul. 20, 2006

Related U.S. Application Data

(63) Continuation-in-part of application No. 11/035,978, filed on Jan. 18, 2005, now Pat. No. 8,934,955.

(51) Int. Cl.
| | | |
|---|---|---|
| *A61B 5/157* | (2006.01) | |
| *A61B 5/00* | (2006.01) | |
| *A61B 5/15* | (2006.01) | |
| *A61B 5/145* | (2006.01) | |
| *A61B 5/151* | (2006.01) | |
| *A61M 5/00* | (2006.01) | |

(52) U.S. Cl.
CPC ............ *A61B 5/1411* (2013.01); *A61B 5/14532* (2013.01); *A61B 5/15146* (2013.01); *A61B 2562/0295* (2013.01); *A61M 5/008* (2013.01)
USPC ............ 600/347; 600/365; 600/583; 600/584

(58) Field of Classification Search
USPC ........... 600/583, 584, 347, 365; 606/181, 182
See application file for complete search history.

(56) References Cited

U.S. PATENT DOCUMENTS

| | | |
|---|---|---|
| 5,035,704 A | 7/1991 | Lambert et al. |
| 5,201,324 A | 4/1993 | Swierczek |
| 5,395,388 A | 3/1995 | Schraga |
| 5,643,306 A | 7/1997 | Schraga |
| 6,228,100 B1 | 5/2001 | Schraga |
| 6,506,168 B1 | 1/2003 | Fathallah et al. |

(Continued)

FOREIGN PATENT DOCUMENTS

WO    WO 2005/018710    3/2005

OTHER PUBLICATIONS

U.S. Appl. No. 11/035,978 in the of Schraga, filed Jan. 18, 2005.

(Continued)

*Primary Examiner* — Lee S Cohen
*Assistant Examiner* — Emily Lloyd
(74) *Attorney, Agent, or Firm* — Greenblum & Bernstein, P.L.C.

(57) ABSTRACT

Cartridge for a testing device and method of testing using the testing device with the cartridge is disclosed. The cartridge includes a plurality of lancet needles and a mechanism allowing the cartridge to be mounted to the testing device. The method provides for puncturing a surface of skin using the testing device by arranging the testing device adjacent or against a user's skin, triggering the testing device so that one of the plurality of lancet needles is caused to penetrate the user's skin, and rotating the cartridge to another position. This Abstract is not intended to define the invention disclosed in the specification, nor intended to limit the scope of the invention in any way.

27 Claims, 54 Drawing Sheets

(56) References Cited

U.S. PATENT DOCUMENTS

| | | | |
|---|---|---|---|
| 7,299,081 B2 * | 11/2007 | Mace et al. | 600/573 |
| 2003/0083686 A1 * | 5/2003 | Freeman et al. | 606/181 |
| 2004/0092995 A1 * | 5/2004 | Boecker et al. | 600/576 |
| 2004/0230216 A1 | 11/2004 | Levaughn et al. | |
| 2005/0118071 A1 | 6/2005 | Sacherer | |
| 2012/0220895 A1 | 8/2012 | Vine et al. | |

OTHER PUBLICATIONS

Chinese Office Action dated Sep. 10, 2010 that issued with respect to patent family member Chinese Patent Application No. 2006-80007541.0. 5 pages.

European Search Report issued in EP 06 73 7254 Mar. 1, 2010, 6 pages.

* cited by examiner

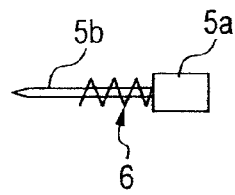  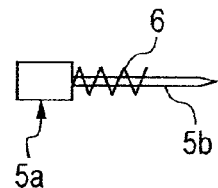
FIG. 5a  FIG. 5b  FIG. 5c
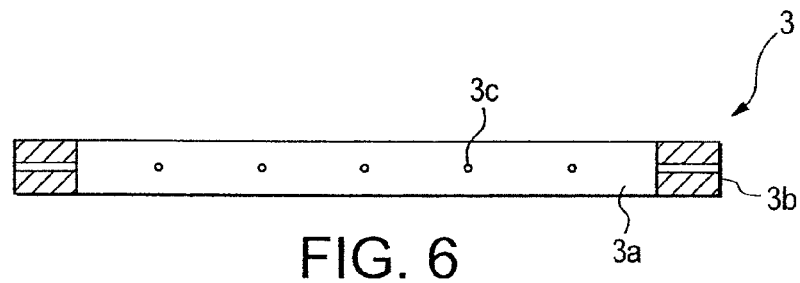
FIG. 6
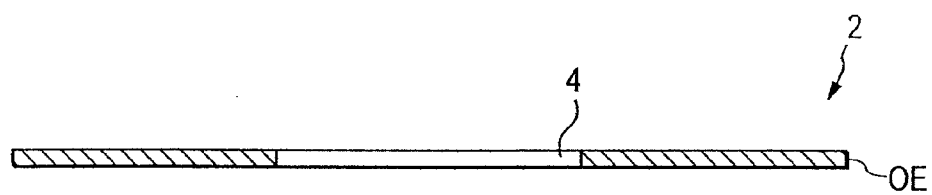
FIG. 7
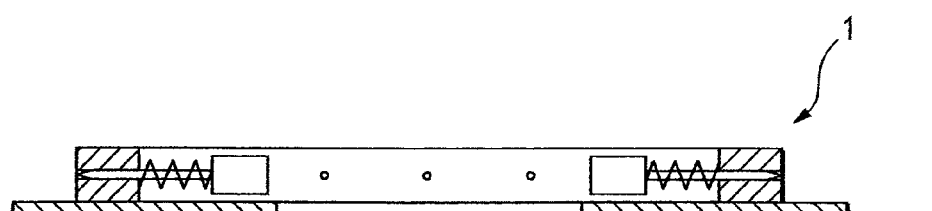
FIG. 8

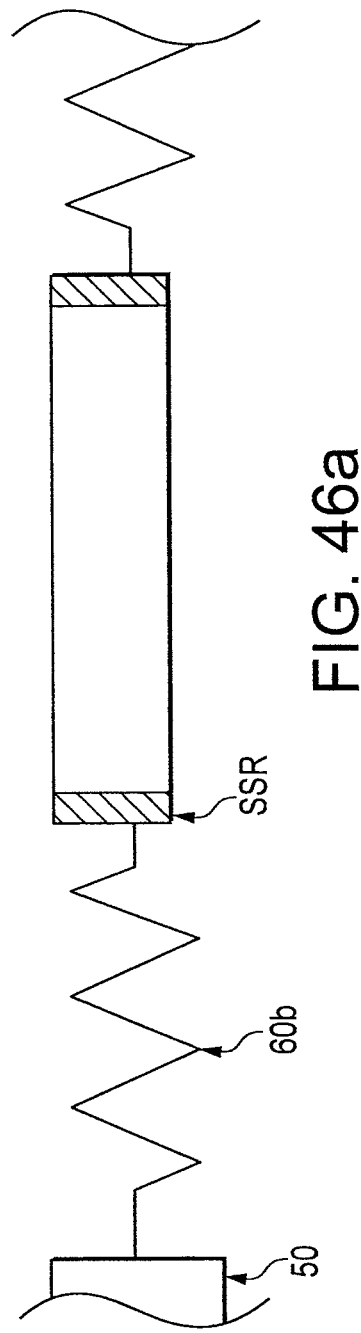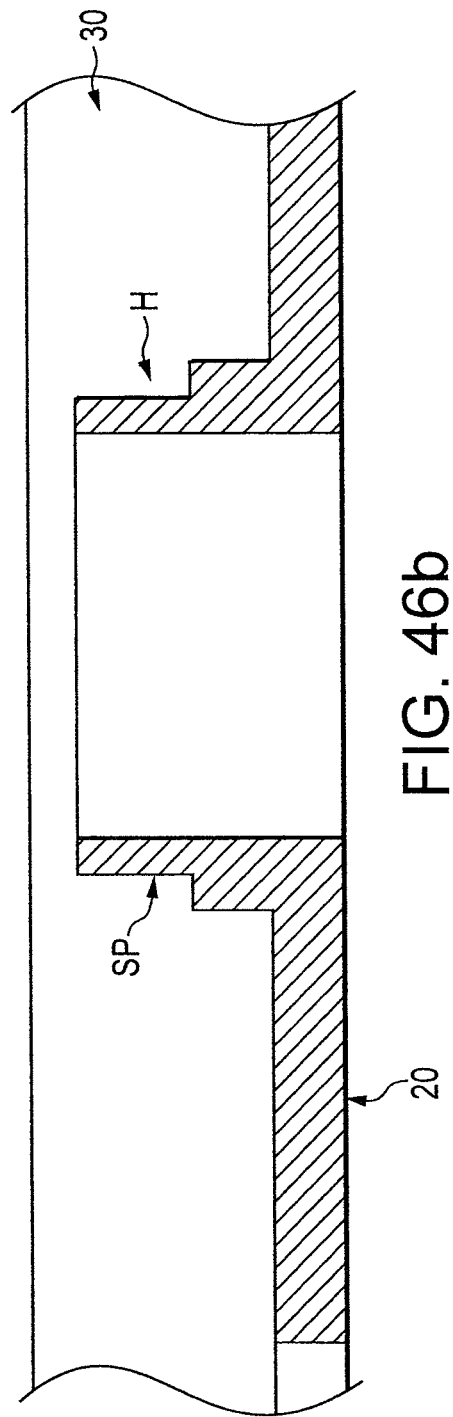

CARTRIDGE WITH LANCETS AND TESTING DEVICE USING THE CARTRIDGE

CROSS-REFERENCE TO RELATED APPLICATIONS

The instant application is a continuation-in-part of U.S. patent application Ser. No. 11/035,978 filed on Jan. 18, 2005, the disclosure of which is hereby expressly incorporated by reference hereto in its entirety.

BACKGROUND OF THE INVENTION

1. Field of the Invention

The invention relates to a cartridge which includes a plurality of movably mounted lancets or lancet needles. The invention also relates to a disposable disk-shaped cartridge for a testing device such as glucose meter. The invention further relates to a method of using a testing device such as a blood glucose meter with a removable/replaceable cartridge. In particular, the invention relates to a cartridge having lancet needles which may be disposable, i.e., which can be used once and discarded, and/or which utilizes an arrangement which protects a user from contacting his or her skin with the same surface of the skin engaging portion after the device has been triggered and/or fired.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Known single-use/disposable lancet devices are not sufficiently and/or properly designed to ensure that they cannot be reused. Moreover, such devices generally do not protect a user from coming into contact with body fluids such as blood which may be on the device after the device has been used.

An improved device would allow the user to use the lancet needle only a single time and more reliably and safely prevent reuse of the lancet needle. The device should also ensure that a contaminated surface of the device cannot come into contact with a user after the device is used. Finally, an improved device would utilize a cartridge which is safe to dispose of, is simple in design, and is inexpensive to produce.

SUMMARY OF THE INVENTION

According to one illustrative aspect of the invention there is provided a disposable cartridge for a testing device or glucose meter.

According to another illustrative aspect of the invention there is provided a cartridge for a testing device, wherein the cartridge comprises a plurality of lancet needles, a plurality of test strips, and a mechanism allowing the cartridge to be mounted to the testing device.

The mechanism may allow the cartridge to be mounted to the testing device and may comprise an opening. Each of the plurality of lancet needles may be generally radially oriented. Each of the plurality of test strips may be generally radially oriented. Each of the plurality of lancet needles may be movably mounted to a disk-shaped body. Each of the plurality of test strips may be non-movably mounted to a disk-shaped body. The cartridge may comprise a generally circular shape. The cartridge may comprise a generally circular shape having an outer diameter of no greater than about 2 inches. The cartridge may comprise a generally circular shape having a thickness of no greater than about 0.25 inches.

The cartridge may further comprise a plurality of springs, wherein each spring is mounted to one of the plurality of lancet needles. Each of the plurality of lancet needles may comprise a head portion and a needle portion.

The cartridge may further comprise a ring-shaped member, wherein each needle portion is arranged within an opening of the ring-shaped member.

The cartridge may further comprise a ring-shaped member, wherein each needle portion is movably mounted in a radial opening of the ring-shaped member.

The cartridge may further comprise a ring-shaped member, wherein each of the plurality of lancet needles is movably mounted to the ring-shaped member.

Each of the plurality of test strips may be non-movably mounted to a planar disk-shaped body. The planar disk-shaped body may comprise a thickness of less than about 0.10 inches. Each of the plurality of test strips may comprise electrical contacts. Each of the plurality of test strips may be generally radially aligned with the plurality of lancet needles.

The cartridge may further comprise an alignment mechanism allowing the cartridge to be mounted to the testing device in only a single position.

The cartridge may further comprise one of a notch and a groove which ensures that the cartridge is mounted to the testing device in a predetermined position.

The cartridge may further comprise a locking mechanism preventing rotation of the cartridge once the cartridge has rotated in the testing device to a locking position.

The cartridge may further comprise an opening which prevents rotation of the cartridge after the cartridge has rotated in the testing device to a locking position.

The invention also provides a method of puncturing a surface of skin using a testing device comprising the cartridge of the type described above, wherein the method comprises arranging the testing device adjacent or against a user's skin, triggering the testing device so that one of the plurality of lancet needles is caused to penetrate the user's skin, placing an amount of blood on one of the plurality of test strips, and rotating the cartridge to another position.

According to another illustrative aspect of the invention there is provided a cartridge for a glucose meter, wherein the cartridge comprises a planar disk-shaped body comprising a plurality of radially oriented test strips and a plurality of radially oriented lancet needles, wherein the cartridge is mountable to the glucose meter.

The planar disk-shaped body may comprise a center opening, wherein the plurality of radially oriented lancet needles are movably mounted, and wherein the center opening allows the cartridge to be removably mounted to the glucose meter.

According to another illustrative aspect of the invention there is provided a method of puncturing a surface of skin using a glucose meter which comprises the cartridge of the type described above, wherein the method comprises arranging the glucose meter adjacent against a user's skin, triggering the glucose meter so that one of the plurality of lancet needles is caused to penetrate the user's skin, placing an amount of blood on one of the plurality of test strips, and rotating the cartridge to another position.

According to another illustrative aspect of the invention there is provided a testing device comprising a housing and a cartridge comprising a plurality of lancet needles and a plurality of test strips, wherein the cartridge is movably mounted within the housing.

The cartridge may be generally disk-shaped and comprise a center opening which is rotatably mounted about a hub arranged within the housing. The plurality of lancet needles may be movably mounted to a disk-shaped body and the plurality of test strips may be generally radially oriented. The plurality of lancet needles may be generally radially oriented. The cartridge may be removably mounted to the housing. The housing may comprise a door which can be opened to remove the cartridge.

According to another illustrative aspect of the invention there is provided a glucose meter comprising a housing and a cartridge comprising a plurality of lancet needles and a plurality of test strips. The cartridge is movably and removably mounted within the housing. A mechanism retains the cartridge in a rotational position. A device allows a user to rotate the cartridge between a plurality of positions.

The housing may comprise a door which can be opened to remove the cartridge. The mechanism which retains the cartridge in a rotational position may comprise a deflecting member. The device which allows a user to rotate the cartridge between a plurality of positions may comprise a motor. The mechanism which retains the cartridge in a rotational position may comprise a motor.

The glucose meter may further comprise an alignment mechanism allowing the cartridge to be initially mounted within the housing in only a single position.

The glucose meter may further comprise one of a notch and a groove which ensures that the cartridge is mounted to the housing in a predetermined position.

The glucose meter may further comprise a locking mechanism preventing rotation of the cartridge once the cartridge has rotated in the housing to a locking position.

The cartridge may comprise an opening which prevents rotation of the cartridge after the cartridge has rotated in the housing to a locking position.

According to another illustrative aspect of the invention there is provided a method of puncturing a surface of skin using the glucose meter of the type described above, wherein the method comprises arranging the housing adjacent or against a user's skin, triggering the glucose meter so that one of the plurality of lancet needles is caused to penetrate the user's skin, placing an amount of blood on one of the plurality of test strips, and rotating the cartridge to another position.

According to another illustrative aspect of the invention there is provided a cartridge for a testing device, wherein the cartridge comprises a plurality of movably mounted lancet needles and a mechanism allowing the cartridge to be mounted to the testing device.

The mechanism allowing the cartridge to be mounted to the testing device may comprise an opening. Each of the plurality of lancet needles may be generally radially oriented and may move without rotating along a generally linear path. The cartridge may further comprise a plurality of test strips which are generally radially oriented. Each of the plurality of lancet needles may be movably mounted to a disk-shaped body. The cartridge may further comprise a plurality of springs, each spring having one end coupled to one of the plurality of lancet needles. The cartridge may comprise a generally circular shape. The cartridge may comprise a generally circular shape having an outer diameter of no greater than about 2 inches. The cartridge may comprise a generally circular shape having a thickness of no greater than about 0.25 inches. The cartridge may further comprise a plurality of springs, wherein each spring is mounted to one of the plurality of lancet needles. Each of the plurality of lancet needles may comprise a head portion and a needle portion.

The cartridge may further comprise a ring-shaped member, wherein each needle portion is arranged within an opening of the ring-shaped member. The cartridge may further comprise a removable retaining device structured and arranged to maintain one of the plurality of lancet needles in at least a partially retracted position. The cartridge may further comprise a ring-shaped member, wherein each of the plurality of lancet needles is movably mounted to the ring-shaped member. The cartridge may further comprise a plurality of test strips non-movably mounted to a planar disk-shaped body. The planar disk-shaped body may comprise a thickness of less than about 0.10 inches. Each of the plurality of test strips may comprise electrical contacts. Each of the plurality of test strips may be generally radially aligned with the plurality of lancet needles.

The cartridge may further comprise an alignment mechanism allowing the cartridge to be mounted to the testing device in only a single position. The cartridge may further comprise one of a notch and a groove which ensures that the cartridge is mounted to the testing device in a predetermined position. The cartridge may further comprise a locking mechanism preventing rotation of the cartridge once the cartridge has rotated in the testing device to a locking position. The cartridge may further comprise an opening which prevents rotation of the cartridge after the cartridge has rotated in the testing device to a locking position.

According to another illustrative aspect of the invention there is provided a method of puncturing a surface of skin using a testing device comprising the cartridge of the type described above, wherein the method comprises arranging the testing device adjacent against a user's skin, triggering the testing device so that one of the plurality of lancet needles is caused to penetrate the user's skin, and rotating the cartridge to another position.

According to another illustrative aspect of the invention there is provided a cartridge for a test device, wherein the cartridge comprises a planar disk-shaped body, a plurality of radially oriented lancet needles, a plurality of springs, and each spring being structured and arranged to at least one of move one of the plurality of lancet needles towards an extended position and move one of the plurality of lancet needles towards a retracted position, wherein the cartridge is structured and arranged to be removably mountable to the test device.

The planar disk-shaped body may comprise a center opening and a plurality of radially oriented guide slots, wherein the plurality of radially oriented lancet needles are movable along a generally linear path without substantially rotating, and wherein the center opening allows the cartridge to be removably mounted to the test device.

According to another illustrative aspect of the invention there is provided a method of puncturing a surface of skin using a test device comprising the cartridge of the type described above, wherein the method comprises arranging the test device adjacent against a user's skin, triggering the test device so that one of the plurality of lancet needles is caused to penetrate the user's skin, and rotating the cartridge to another position.

According to another illustrative aspect of the invention there is provided a testing device comprising a housing and a cartridge comprising a plurality of lancet needles and a plurality of springs, wherein the cartridge is movably mounted within the housing.

The cartridge may be generally disk-shaped and may comprise a center opening which is rotatably mounted about a hub arranged within the housing. The plurality of lancet needles may be movably mounted to a disk-shaped body. The plurality of lancet needles may be radially oriented. The cartridge may be removably mounted to the housing. The housing may comprise a door which can be opened to remove the cartridge.

According to another illustrative aspect of the invention there is provided a glucose meter comprising a housing and a cartridge comprising a plurality of lancet needles. The cartridge is movably and removably mounted within the housing. A mechanism retains the cartridge in at least one rotational position and a device allows a user to rotate the cartridge between a plurality of positions.

The housing may comprise a door which can be opened to remove the cartridge. The mechanism which retains the cartridge in at least one rotational position may comprise a deflecting member. The device which allows a user to rotate the cartridge between a plurality of positions may comprise a motor. The mechanism which retains the cartridge in at least one rotational position may comprise a motor. The device which allows a user to rotate the cartridge between a plurality of positions may comprise the motor. The glucose meter may further comprise an alignment mechanism allowing the cartridge to be initially mounted within the housing in only a single position. The glucose meter may further comprise one of a notch and a groove which ensures that the cartridge is mounted to the housing in a predetermined position. The glucose meter may further comprise a locking mechanism preventing rotation of the cartridge once the cartridge has rotated in the housing to a locking position. The cartridge may comprise an opening which prevents rotation of the cartridge after the cartridge has rotated in the housing to a locking position.

According to another illustrative aspect of the invention there is provided a method of puncturing a surface of skin using the glucose meter of the type described above, wherein the method comprises arranging the housing adjacent against a user's skin, triggering the glucose meter so that one of the plurality of lancet needles is caused to penetrate the user's skin, and rotating the cartridge to another position.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 5a shows a left side view of one of the lancet needles used in the cartridge embodiment shown in FIG. 1. A coil spring is mounted to the needle portion of the lancet needle;

FIG. 5b shows an end view of the lancet needle of FIG. 5a;

FIG. 5c shows a right side view of the lancet needle shown in FIG. 5a;

FIG. 6 shows a cross-section view of the lancet needle holding ring shown in FIG. 3. The lancet needles and springs have been removed;

FIG. 7 shows a cross-section view of the disk-shaped body containing the test strips shown in FIG. 2;

FIG. 8 shows a cross-section view of the cartridge shown in FIG. 1. For the sake of clarity, only the lancet needles positioned at three o'clock and nine o'clock are shown installed on the cartridge. The lancet needles and the springs are not shown in cross-section;

FIGS. 46a and 46b show the partial cross-section view of FIG. 45 in a dis-assembled state with the spring hub being disconnected from the hub of the disk-shaped member;

DETAILED DESCRIPTION OF THE PRESENT INVENTION

Figure 1:
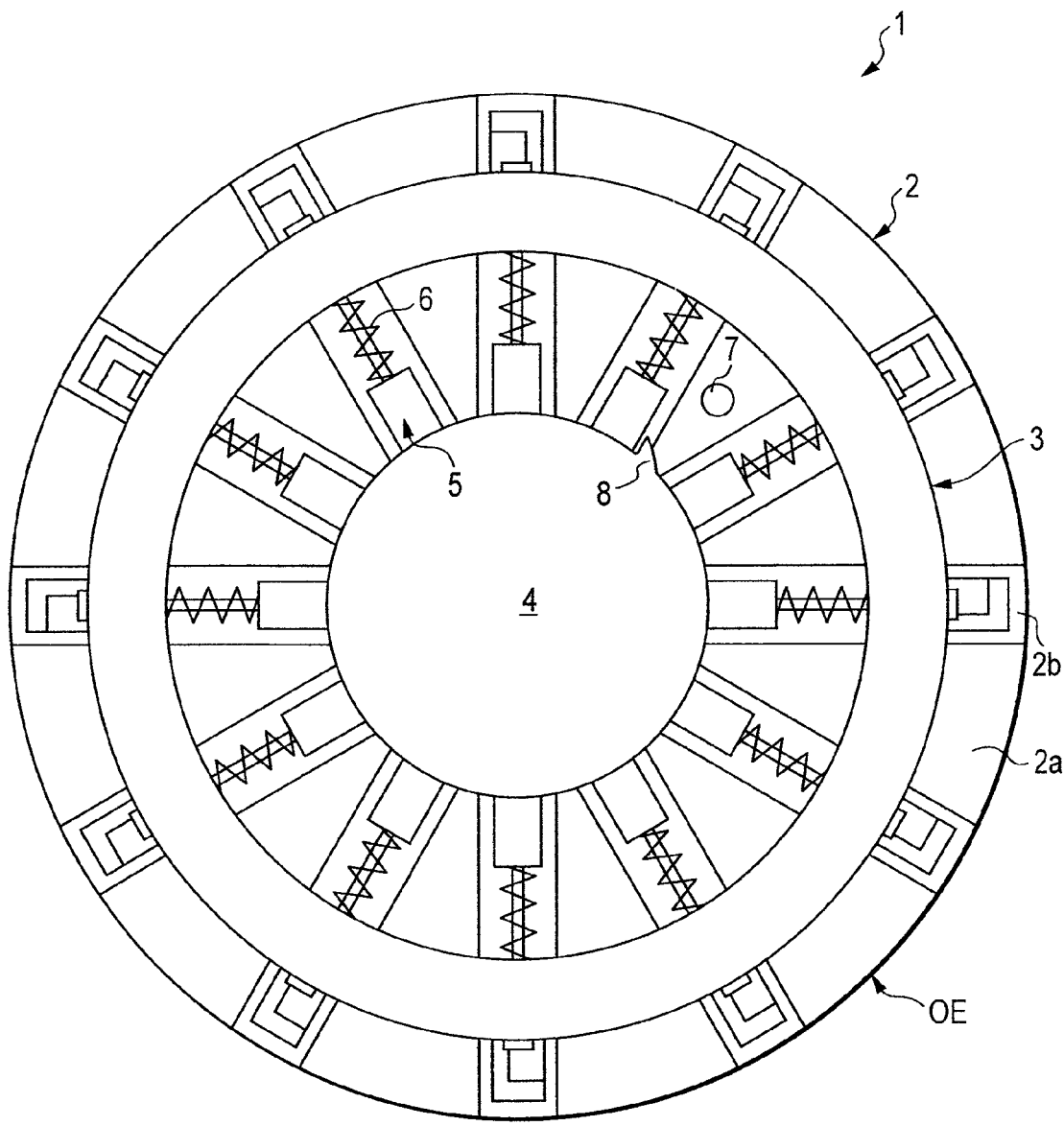
FIG. 1 shows a top view of one embodiment of the cartridge. The contact strips of the test strips extending inwardly from the lancet needle support ring are not shown.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-8 show a first non-limiting embodiment of a cartridge 1. The cartridge 1 includes a disk-shaped planar body 2 and a lancet needle retaining ring 3. A plurality of lancet needles 5 are mounted to the ring 3 radially. Each lancet needle 5 has a cylindrical needle portion 5b and an enlarged head portion 5a which can be engaged or contacted by a mechanism which causes the lancet needle 5 to extend beyond the ring 3 (see e.g., FIG. 18). Each lancet needle 5 is movably mounted within a radially oriented opening 3c formed in the ring 3. A spring 6 is mounted to each lancet needle 5 in order to ensure that the lancet needle 5 automatically retracts once the lancet needle 5 is caused to move to an extended puncturing position. A plurality of test strips 2b are also radially arranged and are generally aligned with the lancet needles 5. By way of non-limiting example, the disk-shaped body 2 can have an outer diameter of between approximately 1.5" and 3" and is preferably approximately 2" in diameter. The cylindrical portion 5b of the lancet needles 5 can be made of metal such as stainless steel and can also be of the same material and diameter as conventional lancet needles. The cylindrical head portion 5a can have a diameter of approximately 0.15" and can be made of a synthetic resin material which is injection molded onto the cylindrical portion 5b. The springs 6 can be of any desired type and can preferably be a wire compression spring. The test strips 2b can be in the range of between approximately 0.15" and approximately 0.25" in width, approximately 0.025" and approximately 0.1" in thickness and between approximately 0.5" and approximately 1.25" long.

As can be seen in FIG. 1, the cartridge 1 can utilize a centrally disposed opening 4 which allows the cartridge 1 to be mounted to a mounting arrangement MA (see FIGS. 9-18). Of course, the cartridge 1 can have a variety of designs in order to allow it to be mounted to any number of testing devices. One important aspect of the cartridge 1 relates to the use of a plurality of test strips 2b and a plurality of lancet needles 5. In order to ensure that the cartridge 1 is installed in a desired predetermined position of a mounting arrangement MA, the cartridge 1 can include an alignment mechanism 8. This alignment mechanism 8 can have the form of a notch which slides over a projection of the mounting arrangement MA thereby ensuring that the cartridge 1 can only be installed when oriented in a single angular position. In order to ensure that the cartridge 1 will rotate or index in only a single time, i.e., only 360 degrees, the cartridge 1 can include a locking mechanism 7. This locking mechanism 7 can have the form of an opening within which a pin 101 of the mounting arrangement MA extends when the cartridge 1 rotates a full 360 degrees from an originally installed position. Once the pin 101 engages the opening 7, the user will know that the cartridge 1 has been fully used, i.e., the user will be able to discern that all of the test strips 2*b* and lancet needles 5 have been used once and that it is time to remove the cartridge 1, discard it, and replace it with a fresh cartridge 1. In order to remove the cartridge 1, the user can simply lift the cartridge 1 out of the mounting arrangement MA slightly, rotate it counter-clockwise one indexing position until the notch 8 is aligned with the projection 108, and then lift it completely out of the mounting arrangement MA. This removal process can also be facilitated by the user pressing down, using either a tool or a finger, on the pin 101 which is biased upwards by a spring.

Figure 2:
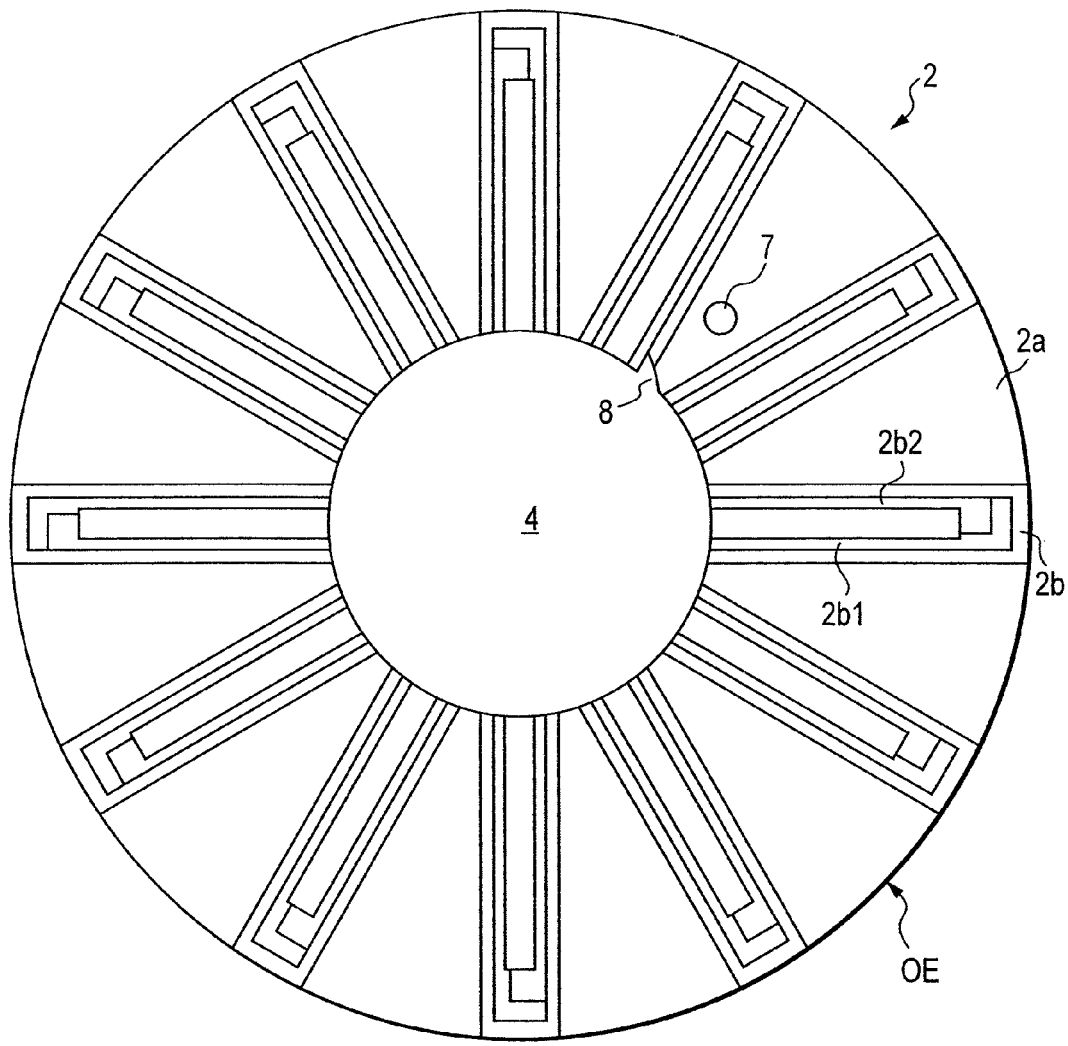
FIG. 2 shows a top view of the cartridge of FIG. 1 with the lancet needle support ring and the lancet needles removed therefrom.
Figure 3:
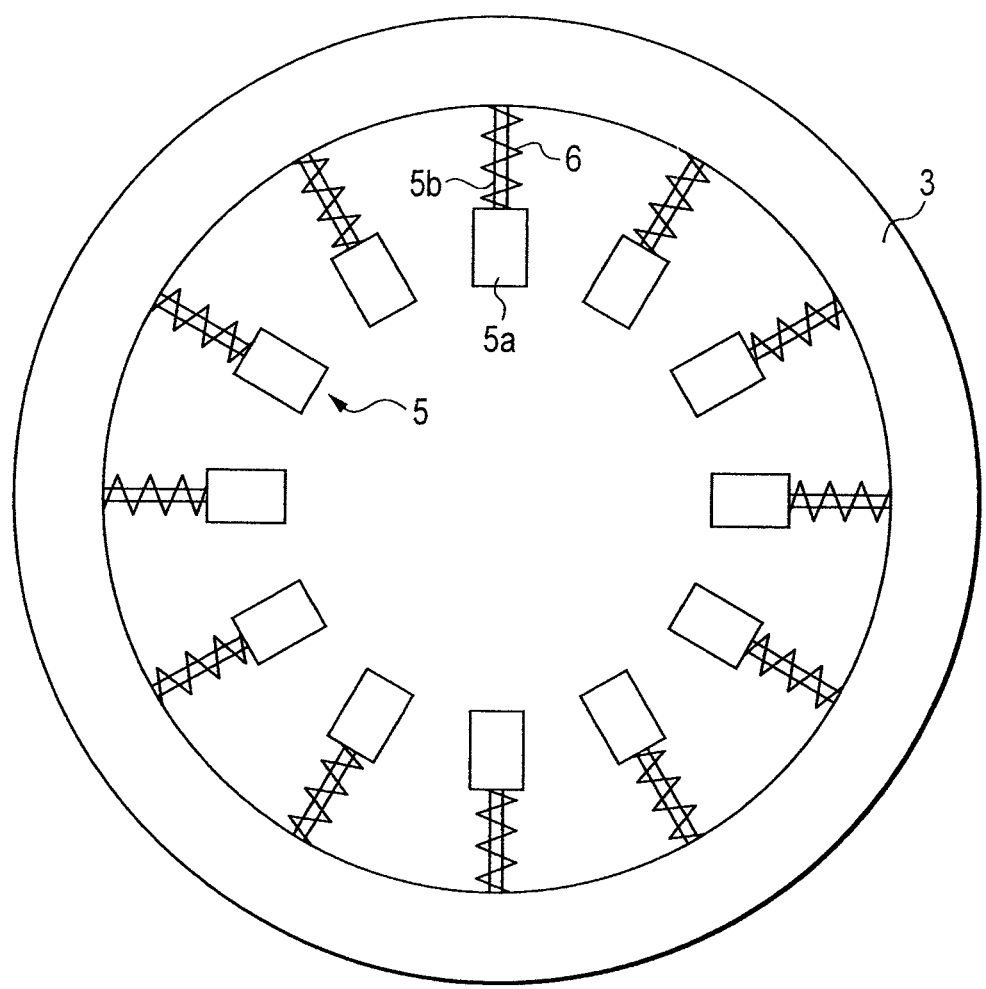
FIG. 3 shows a top view of the lancet needle support ring and the lancet needles used in the embodiment of FIG. 1.
Figure 4:
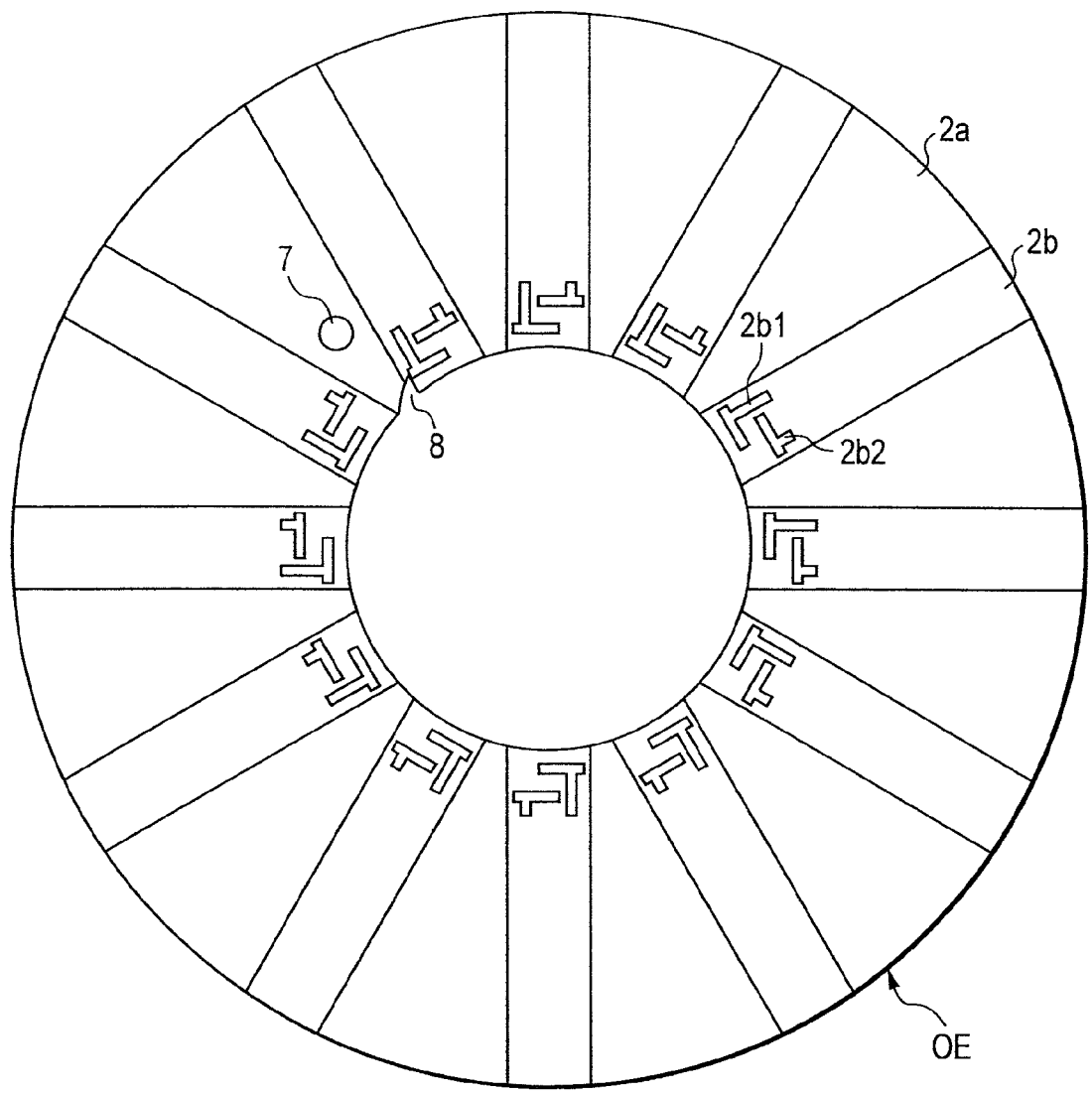
FIG. 4 shows a bottom view of the cartridge of FIG. 1.
Figure 9:
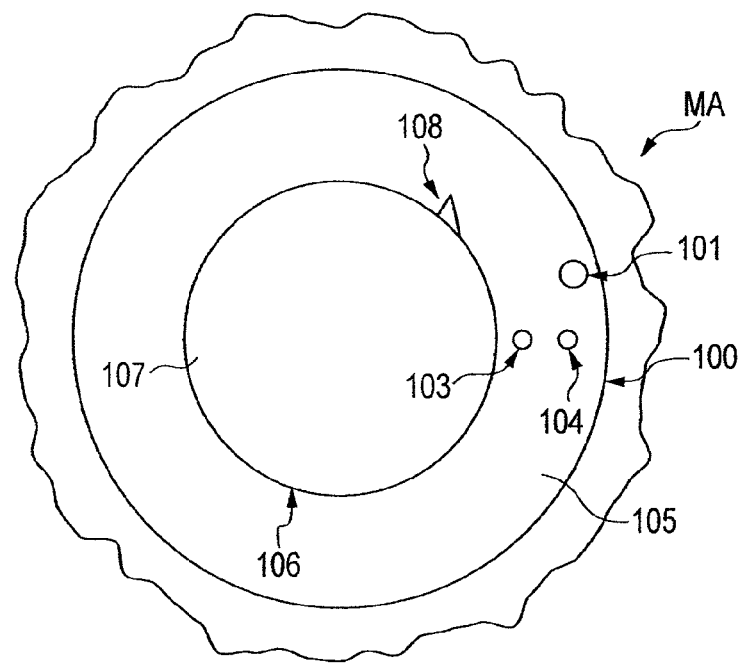
FIG. 9 shows a top view of one embodiment of a mounting arrangement which can be used to mount the cartridge of FIG. 1 in a testing device.
Figure 10:
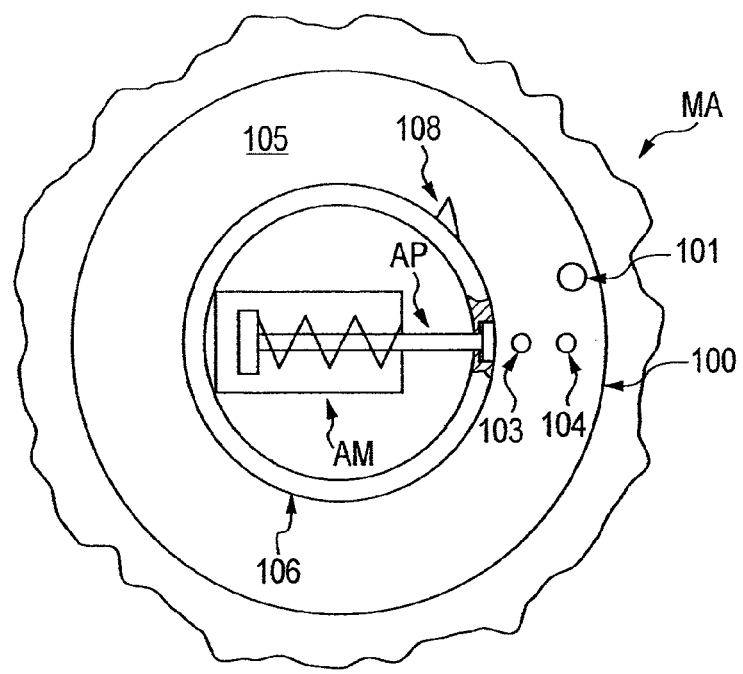
FIG. 10 shows a top view of the mounting arrangement of FIG. 9 with a hub cover removed to expose an electrical actuating mechanism which is used to move each lancet needle to an extended puncturing position.
Figure 11:
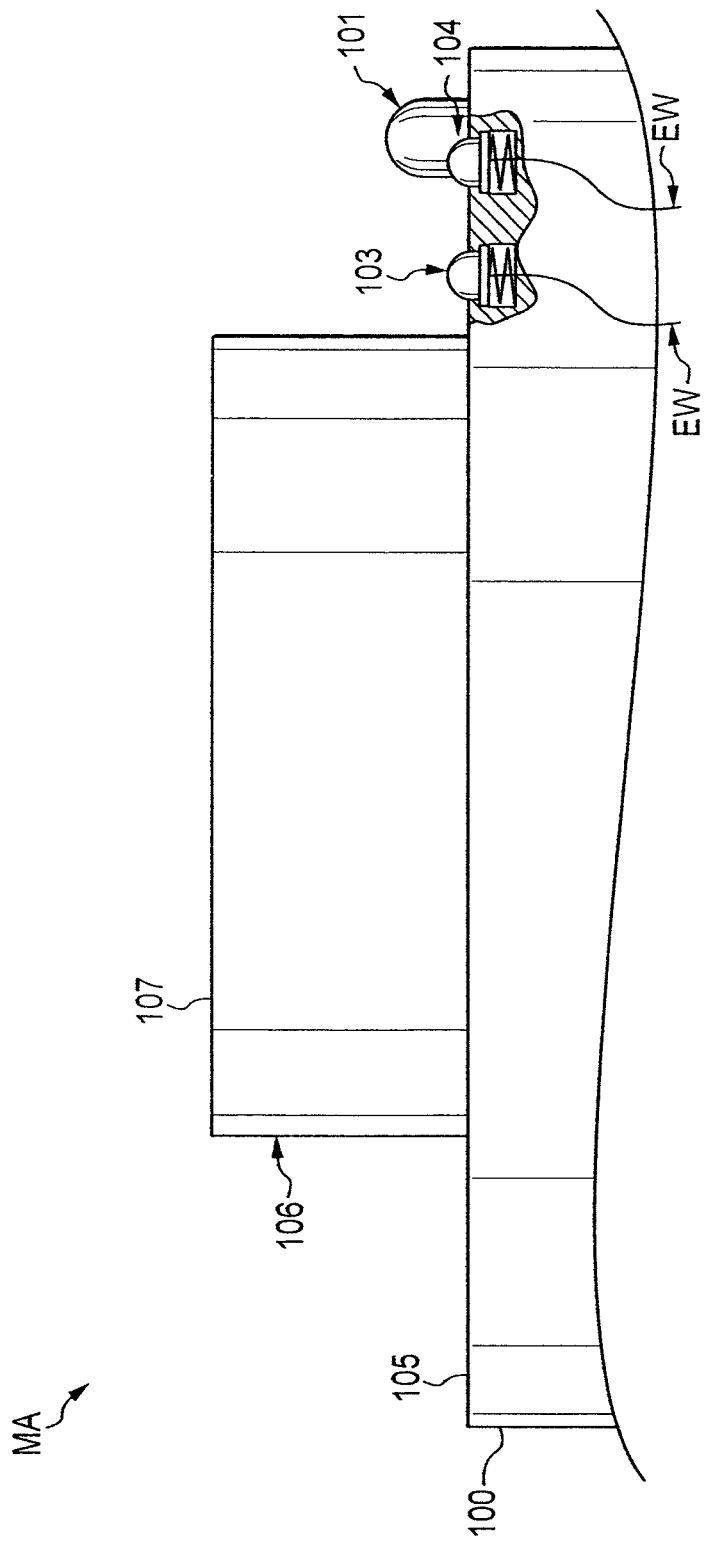
FIG. 11 shows a side view of the mounting arrangement of FIG. 9.
Figure 12:
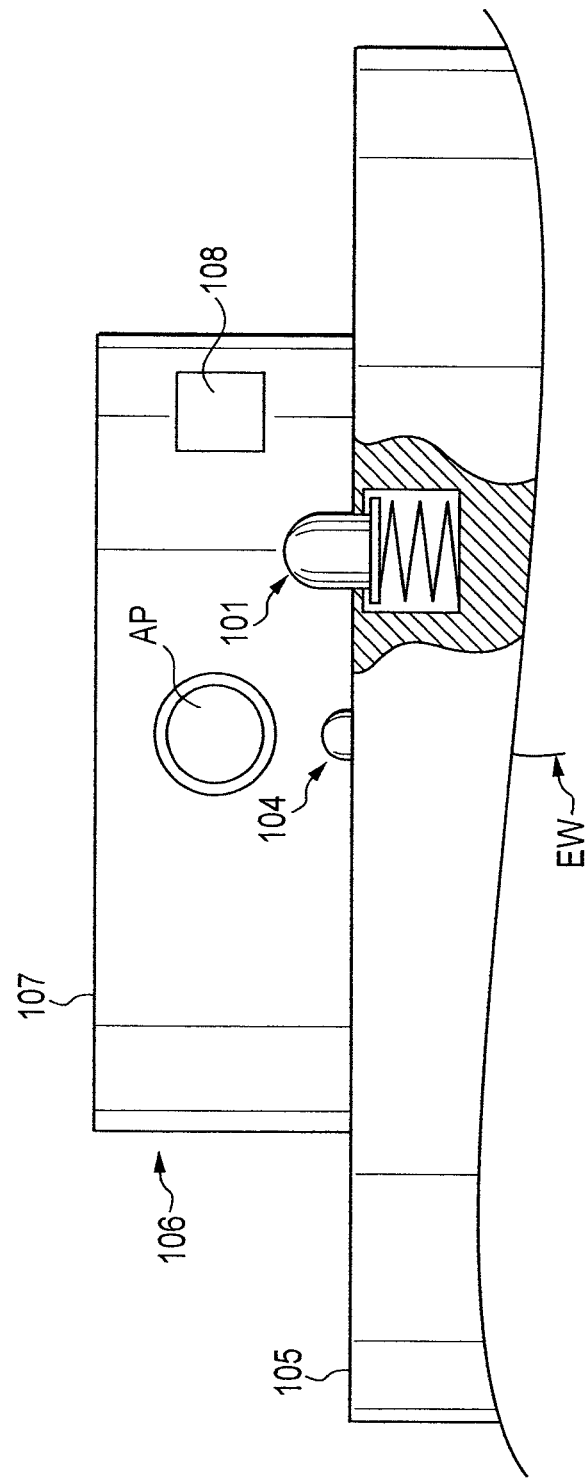
FIG. 12 shows a side view of the mounting arrangement of FIG. 11. The side view is of the mounting arrangement rotated from the three o'clock position of FIG. 11 to the six o'clock position shown in FIG. 12.
Figure 13:
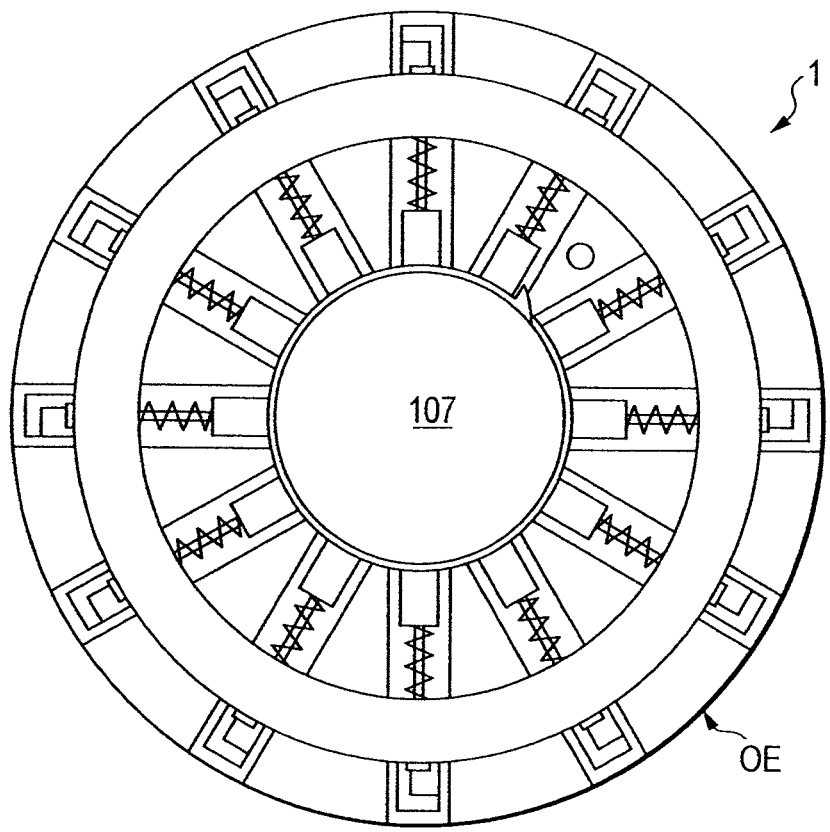
FIG. 13 shows a top view of the cartridge of FIG. 1 installed on the mounting arrangement of FIGS. 9-12.
Figure 14:
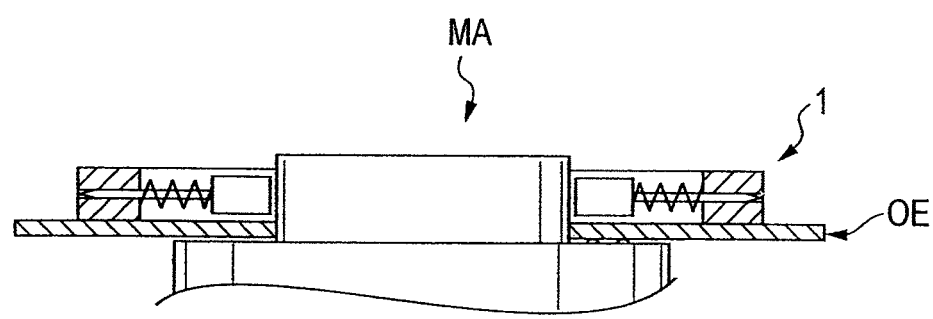
FIG. 14 shows a side cross-section view of FIG. 18. The cartridge of FIG. 8 is shown installed on the mounting arrangement of FIG. 11.
Figure 15:
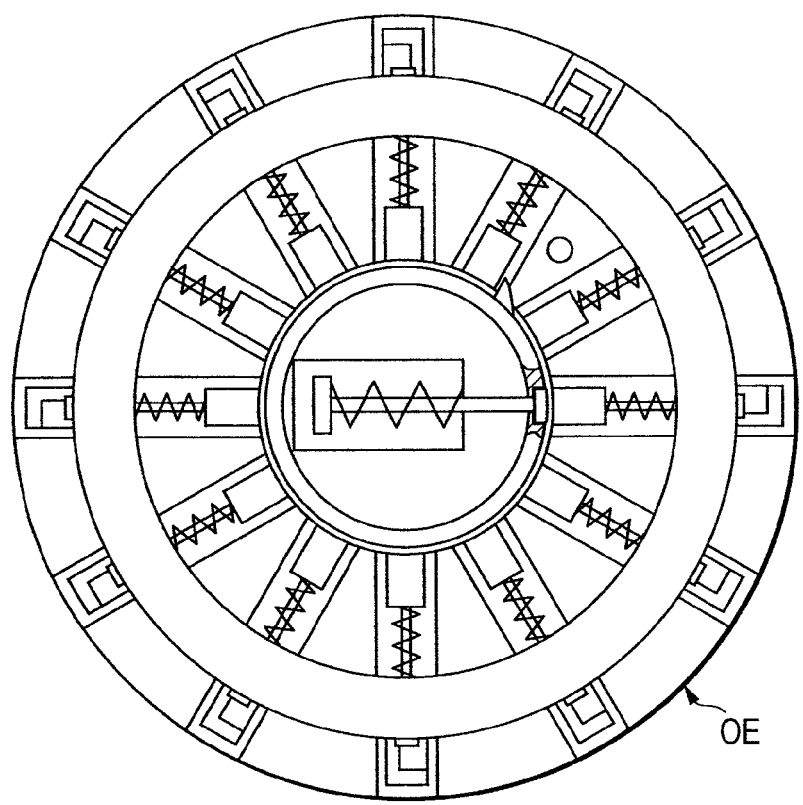
FIG. 15 shows a top view of the cartridge of FIG. 1 installed on the mounting arrangement of FIG. 10. The actuating plunger is shown in a retracted position prior to the testing device being triggered.
Figure 16:
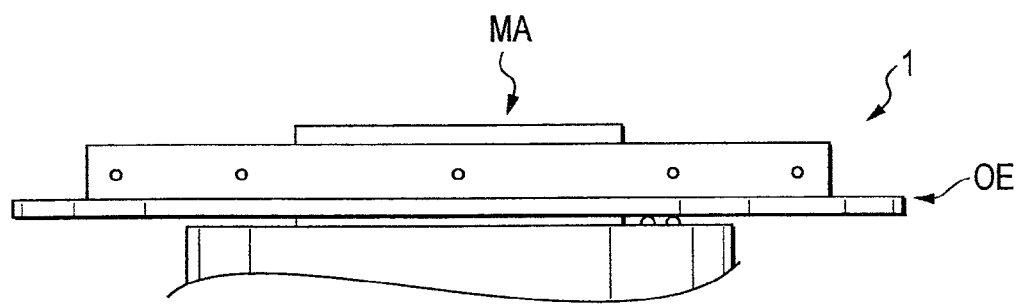
FIG. 16 shows a side view of FIG. 15.

As can be seen in FIGS. 2 and 4, the test strips 2*b* include electrical contacts 2*b*1 and 2*b*2. In the upper surface of the body 2, the contacts are exposed to a blood drop of the user in an area adjacent the outer circumferential edge OE of the body 2. The arrangement of contacts on a test strip which will receive a blood drop is, of course, conventional. The contacts 2*b*1 and 2*b*2 extend along the test strip 2*b* and are electrically connected to contact pads or surfaces arranged on a lower surface of the body 2. These contact pads are positioned to ensure that they provide electrical contact with contacts 103 and 104 of the mounting arrangement MA. As the contacts 103 and 104 are positioned in only a single location, i.e., at 3 o'clock (see FIGS. 9-11) on the mounting arrangement MA, an electrical connection is established between a testing device and each test strip 2*b* only when the test strip 2*b* is located in a predetermined position and/or triggering position.

As can be seen in FIGS. 5*a*-8, the cartridge 1 is simple in design and construction and includes only four main parts, i.e., the body 2, the ring 3, the needles 5 and the springs 6. The ring 3 has an inside surface 3*a*, an outside surface 3*b*, and openings 3*c* which receive therein lancet needles 5*b*. The ring 3 can be a synthetic resin material and can be made by injection molding and thereafter provided with the openings 3*c* by, e.g., drilling. Alternatively, the ring 3 can be made by securing together two pieces each having half-openings formed therein. The ring 3 can be secured to the body 2 by any number of techniques such as bonding, ultrasonic welding, fasteners, snap connections, etc. Although the ring 3 is shown having a generally rectangular cross-section, the invention also contemplates a ring 3 having a square cross-section as well as other shapes. The equally spaced openings 3*c* are, of course, made to be slightly larger in diameter than the cylindrical portions 5*b* so that the lancet needles 5 are capable of sliding freely within the openings 3*c*.

FIGS. 9-12 illustrate one non-limiting mounting arrangement MA by which one can mount the cartridge 1 to a testing device such as a glucose meter. The mounting arrangement MA can utilize a cartridge support surface 105 which is coupled to and/or formed integrally with a wall 100 of the testing device or the housing thereof. A hub member 106 extends from the support surface 105. A cover 107 covers the hub 106. The hub 106 can be generally circular and can have an outer diameter which is slightly smaller than the central opening 4 of the cartridge 1. An actuating mechanism AM is arranged within the hub 106. The actuating mechanism AM is designed to engage one of the lancet needles 5 when the cartridge 1 is located in one of a number of predetermined positions. In this regard, the actuating mechanism AM can have the form of a solenoid wherein an electrically actuated plunger AP is caused to extend out from the hub 106 rapidly when the solenoid is electrically energized. The solenoid includes a spring for automatically retracting the plunger AP. The solenoid is designed so that the plunger AP is expanded and retracted quickly, i.e., in a fraction of a second, so that the lancet needle 5 can also expand and retract quickly. Although not shown, the solenoid can be electrically connected to the processor circuit of the testing device via wires and/or other types of electrical connections. Of course, the invention contemplates non-electrical and/or mechanical devices for causing the lancet needles 5 to move to the extended position.

As explained above, the mounting arrangement MA includes an alignment projection 108 which extends from the outer cylindrical surface of the hub 106. The projection 108 has a triangular shape which corresponds to the shape of the notch 8 of the cartridge 1. Two spring biased electrical contact pins 103 and 104 extend from the support surface 105. As explained above, these pins 103 and 104 provide electrical contact with the contacts 2*b*1 and 2*b*2 of each test strip 2*b* when the test strip 2*b* is located above the contacts 103 and 104. Although not shown, the contact pins 103 and 104 are connected to the processor of the testing device via wires EW or other electrical connections. A spring biased locking pin 101 also extends from the support surface 105. As explained above, this pin 101 engages the lower surface of the cartridge 1 until the opening 7 moves directly over the pin 101 wherein the pin 101 then protrudes into the opening 7 so as to prevent further rotational movement of the cartridge 1.

FIGS. 13-16 show the cartridge 1 mounted to the mounting arrangement MA. In this position, the notch 8 is aligned with the projection 108 and the lancet needles 5 are all in the retracted position.

Figure 17:
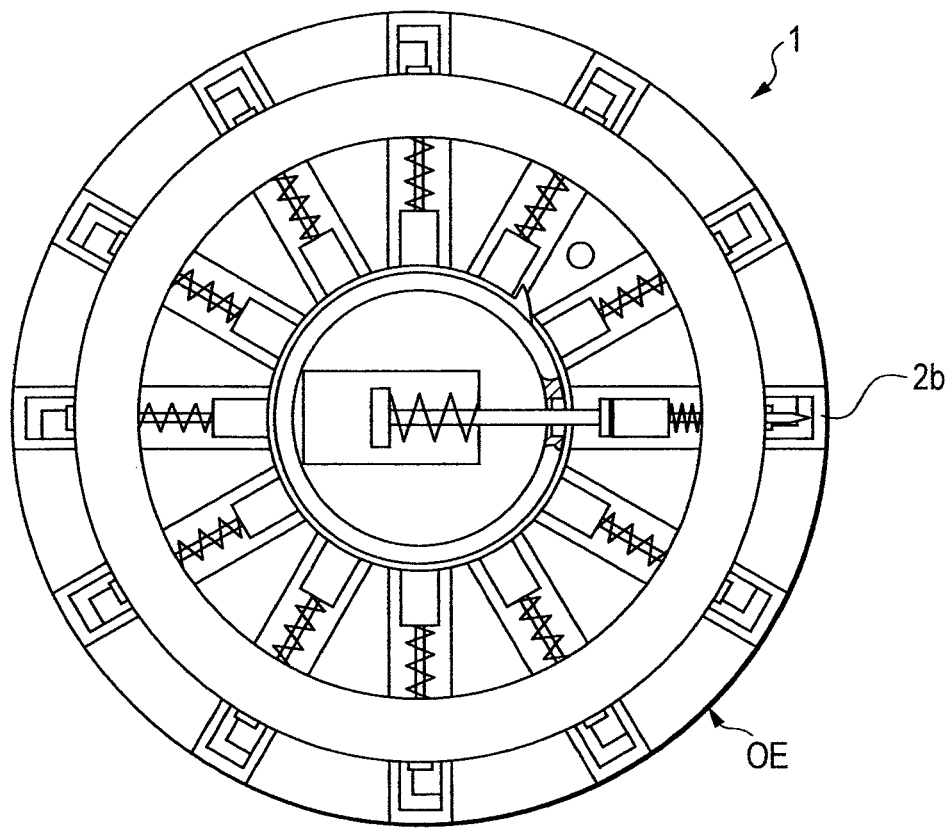
FIG. 17 shows a top view similar to that of FIG. 15 with the actuating plunger being shown in an extended position after the testing device is triggered.
Figure 18:
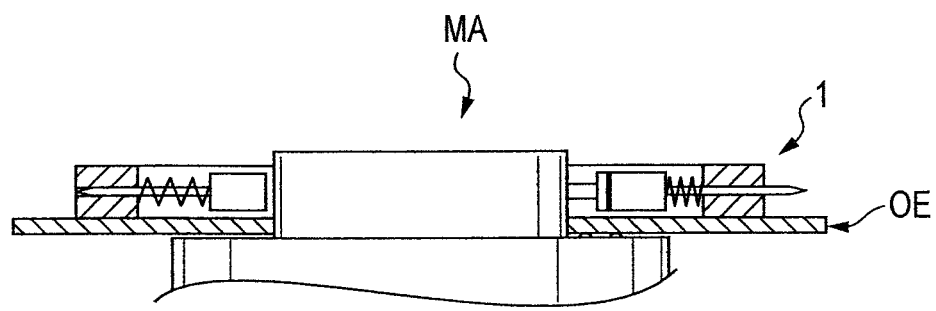
FIG. 18 shows a side cross-section view of FIG. 17.
Figure 19:
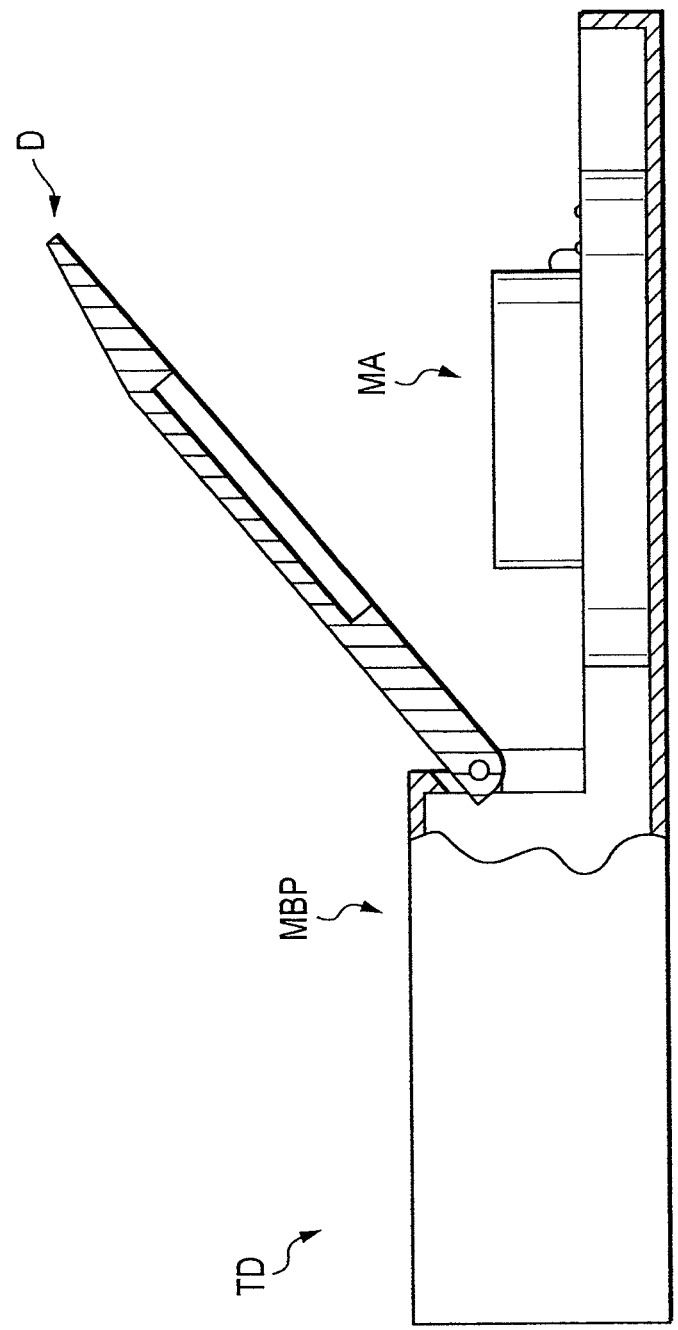
FIG. 19 shows a side view of a testing device which includes the mounting arrangement of FIGS. 9-12. The testing device is shown with a door in an open position and ready to receive the cartridge.
Figure 20:
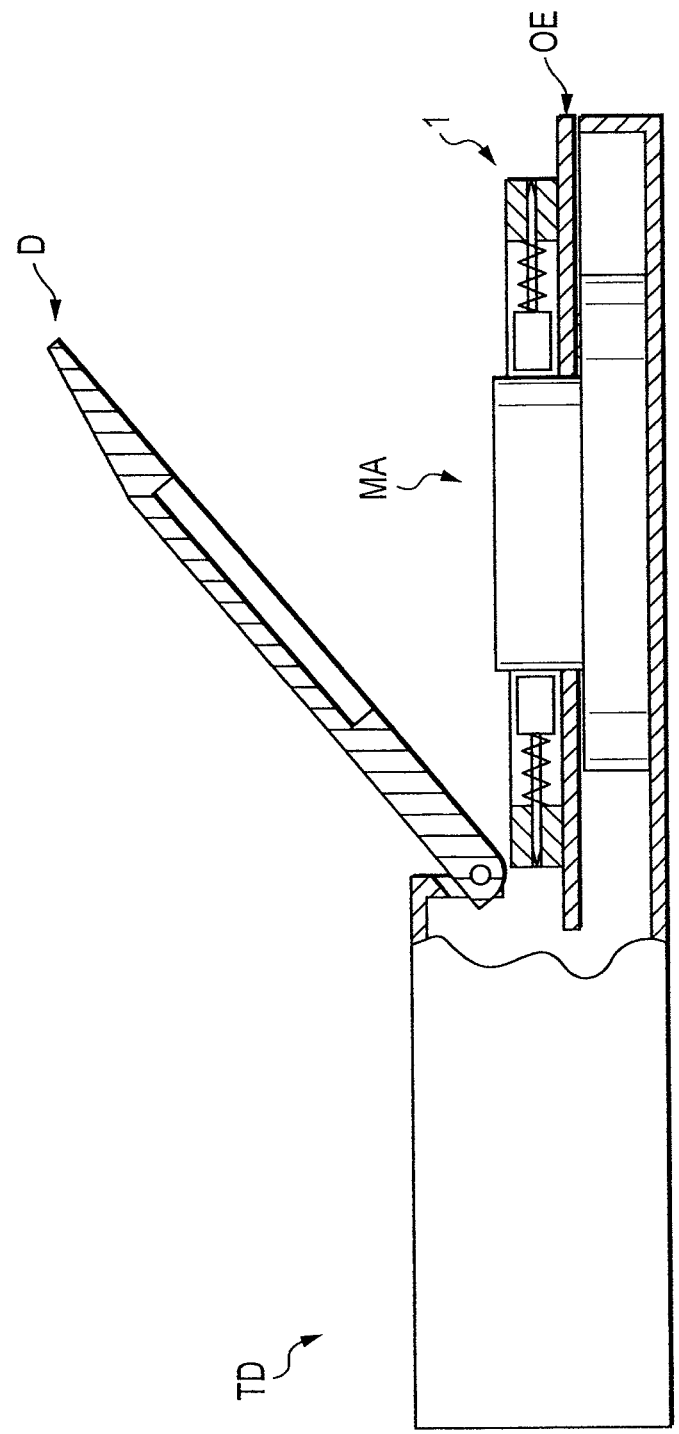
FIG. 20 shows a side view of the testing device of FIG. 19 with the cartridge of FIG. 1 installed therein.
Figure 21:
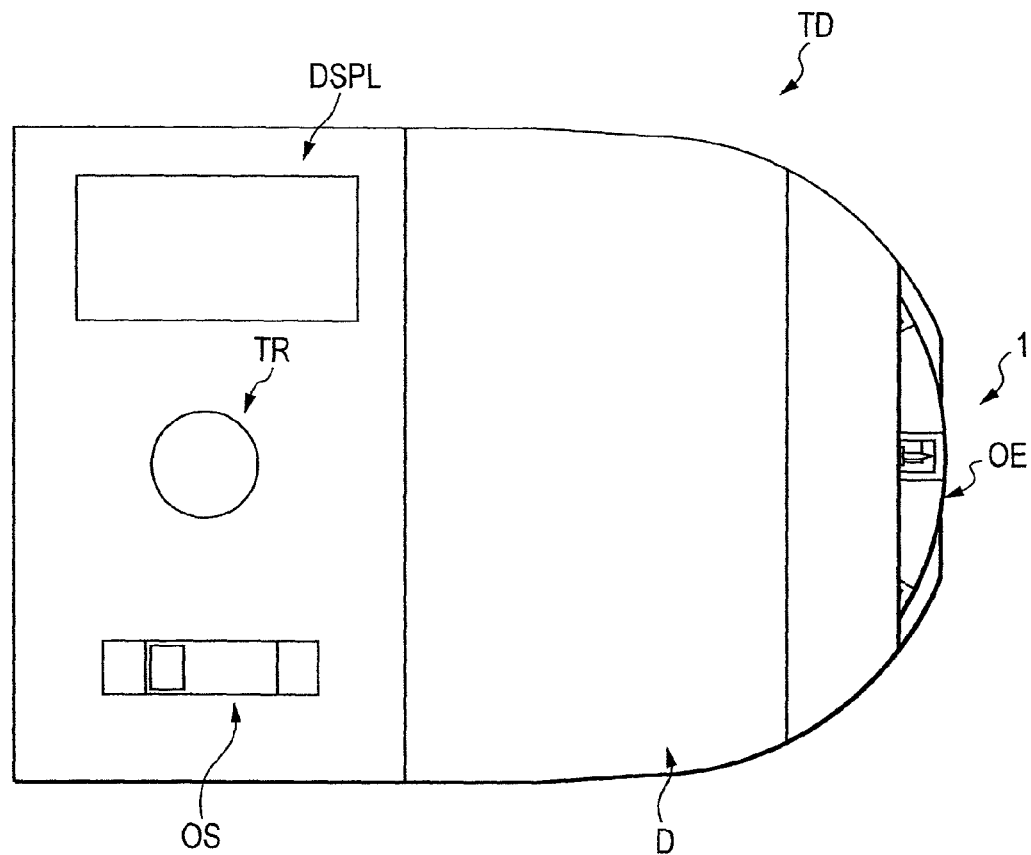
FIG. 21 shows a top view of the testing device of FIG. 22. The test device includes, among other things typically utilized on a test device or glucose meter, a display, a trigger and an on-off switch.

FIGS. 17 and 18 show what happens to the lancet needle 5 at the 3 o'clock position when the solenoid or actuating member AM is activated. As can be seen, the lancet needle 5 extends beyond an outer circumferential surface of the ring 3. This occurs forcing the lancet needle 5 radially outwardly against the biasing force of the spring 6. In this position, the needle would puncture a user's finger (see e.g., FIG. 22). Once retracted, the user can simply rotate the finger so that a drop of blood is placed onto the contacts of the test strip 2*b* which is positioned directly beneath the needle 5. Moreover, because the test strip 2*b* is positioned over the contacts 103 and 104, the user will be able to determine a blood testing result from the testing device by placing a drop of blood onto the test strip 2*b*. The particular way in which the testing device or glucose meter determines the blood testing result from a blood sample placed on a test strip is conventional and is not discussed in detail herein.

Figure 22:
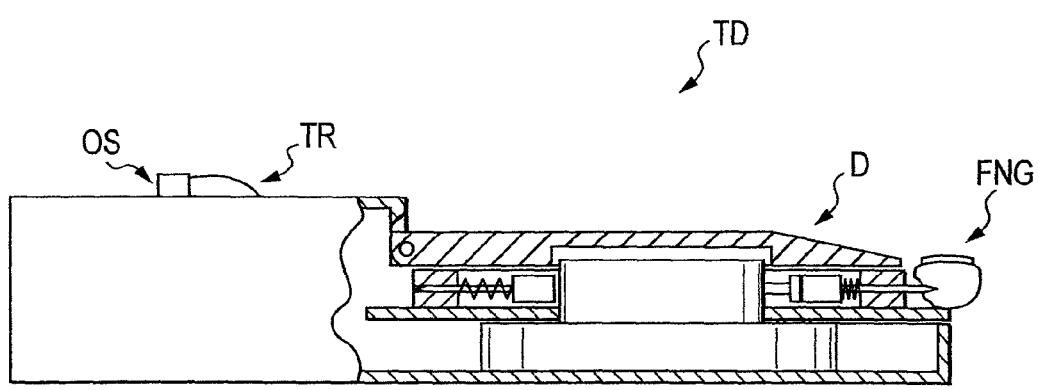
FIG. 22 shows a side view of the testing device of FIG. 20 with the door shown in a closed position. A finger is shown being punctured by one of the lancet needles after the test device has been triggered.

FIGS. 19-22 shows one non-limiting testing device TD and/or a housing thereof which can utilize the mounting arrangement MA. In this embodiment, the testing device TD utilizes a main body portion MBP and a cartridge receiving portion which includes the mounting arrangement and a door D which can be opened and closed to allow a user to remove the cartridge 1. In this embodiment, the door D is hinged or pivotally mounted to the main body portion MBP. Of course, the invention contemplates other ways of mounting the door D. Although not shown, the main body portion MBP can include all of the features conventionally used on glucose meters such as a processor, battery, display DSPL, input keys, a trigger TR, an on/off switch OS, as well as other electronic components. FIG. 22 illustrates one way in which the testing device can be used to puncture a user's finger FNG. Once punctured, the user can rotate and/or manipulate the finger FNG to place a blood drop onto the contacts of the test strip 2*b* to enable the testing device to provide a result. The way in which the result is produced in a testing device, such as a glucose meter, by placing a drop of blood on a test strip is, of course, conventionally known and will not be described in detail herein. By way of non-limiting example, the user can rotate the cartridge 1 between the various counter-clockwise positions by manually engaging the outer edge OE with a finger. In this regard, the outer edge OE can be provided with a high-friction surface. This high friction edge can take the form of e.g., a silicone rubber layer or a knurled or grooved edge.

Figure 23:
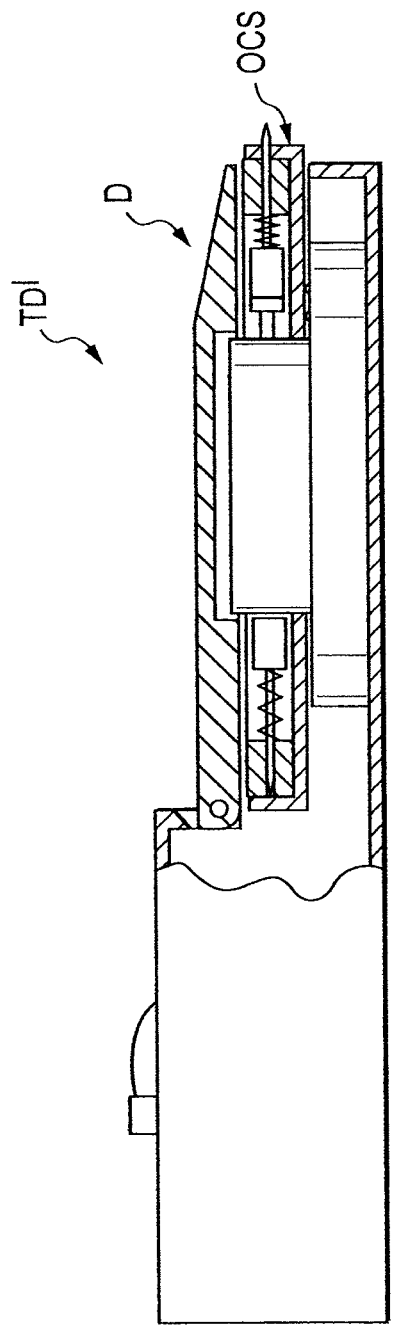
FIG. 23 shows a side view of another embodiment of a testing device. The testing device is shown with the door in a closed position and includes the mounting arrangement and a second embodiment of a cartridge shown in FIG. 24. One of the lancet needles is shown in the extended position after the test device has been triggered.
Figure 25:
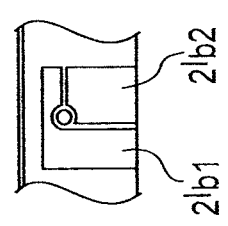
FIG. 25 shows a partial side view of the outer surface of the annular rim showing the test strip contacts and the opening through which passes one of the lancet needles.
Figure 24:
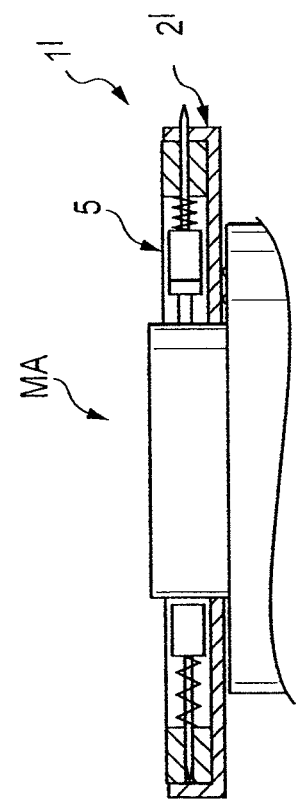
FIG. 24 shows a side view of the mounting arrangement of FIGS. 9-12 with a second embodiment of a cartridge. The cartridge is similar to that shown in FIG. 1 except that an outer circular edge has been bent or oriented upwards at a right angle forming an annular and/or cylindrical rim. Moreover, in this cartridge, unlike the cartridge of FIG. 1, the electrical contacts which receive the blood drop for testing are arranged on an outer surface of the test strip body, and include openings which allow the lancet needles to pass through the annular rim. One of the lancet needles is shown in the extended position after being triggered.

FIGS. 23-25 shows a side view of another embodiment of a testing device TD'. The testing device TD' is similar to that of FIGS. 19-22 and utilizes a door D. However, this embodiment of the testing device TD' is designed to function with a second embodiment of a cartridge 1'. The cartridge 1' is shown in FIG. 24 mounted to the mounting arrangement MA. As is shown in FIG. 24, the cartridge 1' is designed so that the lancet needles 5 extend through the test strips. In this regard, FIG. 24 shows one of the lancet needles 5 in the extended position after the test device has been triggered. The cartridge 1' is similar to the first embodiment shown in FIG. 1 except that an outer circular edge has been bent or oriented upwards at a right angle thereby forming an annular and/or cylindrical rim. Moreover, in this cartridge 1', unlike the cartridge of FIG. 1, the portion of electrical contacts which receive the blood drop for testing are arranged on an outer cylindrical surface OCS of the test strip body. As a result, the outer ends of the test strips include an opening (see FIG. 25) which allows the lancet needle 5 to pass through the annular rim. As can be seen in FIG. 25, the contact portions 2'*b*1 and 2'*b*2 are spaced slightly from the opening to ensure that the needle does not form an electrical connection between the contact portions 2'*b*1 and 2'*b*2 when it moves to the extended position shown in FIG. 24. Although the cartridge 1' embodiment shown in FIGS. 23 and 24 utilizes a lancet retaining ring 3 of the type used in the cartridge 1 shown in FIG. 1, the invention contemplates a cartridge body 2' which does not utilize the ring 3. Instead, at least the cylindrical end portion of the body is made sufficiently thick to perform the needle retaining function of the ring 3. Alternatively, as is contemplated with any of the cartridge embodiments disclosed herein, the ring 3 and body 2 (and more specifically the ring 3 and portions 2*a*) can be formed as a one-piece member. With reference to FIG. 23, it can be seen that the testing device TD' would function as follows: once a user places a skin surface against the outer cylindrical surface OCS, the device can be triggered to cause the lancet needle 5 to move quickly to the extended position (see FIG. 23) and back to a rest or initial position. If the user then allows the skin surface to remain positioned against the surface OCS, the contacts 2'*b*1 and 2'*b*2 will be able to receive the blood which exits from the puncture. The testing device TD' can thus provide a result more quickly since it does not require the user to significantly reposition the skin surface to obtain the blood sample.

Figure 26:
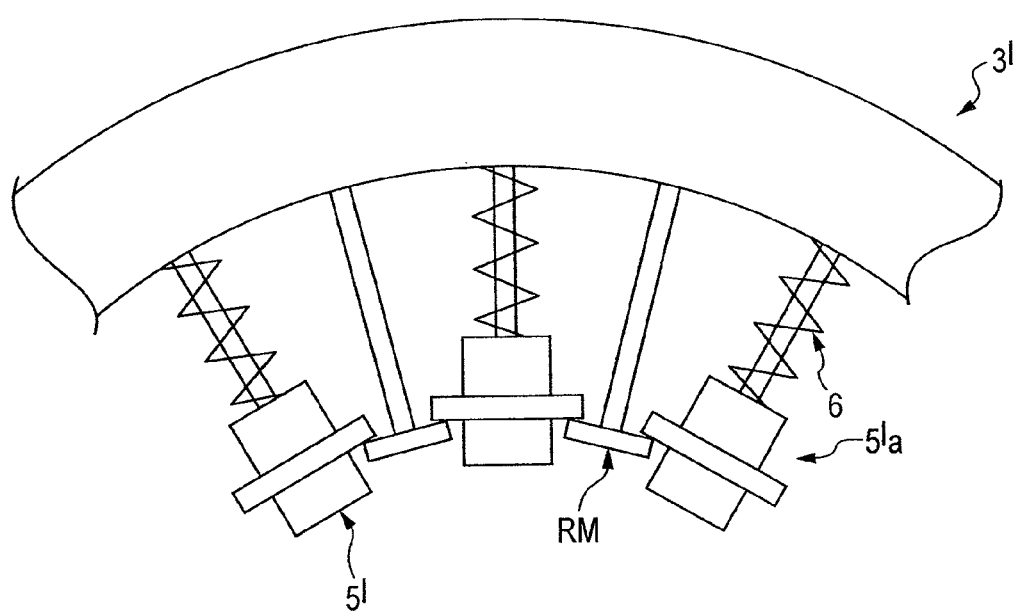
FIG. 26 shows a partial top view of another embodiment of an assembly including a lancet needle holding ring and lancet needles. This arrangement provides for a plurality of radially oriented retaining members which ensure that the lancet needles remain mounted to the lancet needle holding ring. The assembly can be used on the cartridge shown in FIG. 1 in place the assembly shown in FIG. 3.

FIG. 26 illustrates another embodiment of a lancet needle holding ring 3' and needles 5' which can be used on any of the cartridges disclosed herein. The ring 3' is similar to ring 3 shown in FIG. 3 except that it also includes a plurality of lancet needle retaining members RM. The retaining members RM are generally radially arranged and are equally angularly spaced. Each retaining member RM has one end coupled to an inner cylindrical surface of the ring 3' and a head portion which engages with portion of a flange of the head 5'*a* of the lancet needles 5'. This arrangement thus provides for a plurality of radially oriented retaining members RM which ensure that the lancet needles 5' remain mounted to the lancet needle holding ring 3' when the cartridge is removed from the testing device. The retaining members RM can be integrally formed with the ring 3' and can be deflectable so that the lancet needles 5' can be installed on the ring 3' more easily. Of course, this ring 3' and needle 5' arrangement can be used on any of the cartridge embodiments disclosed herein.

Figure 27:
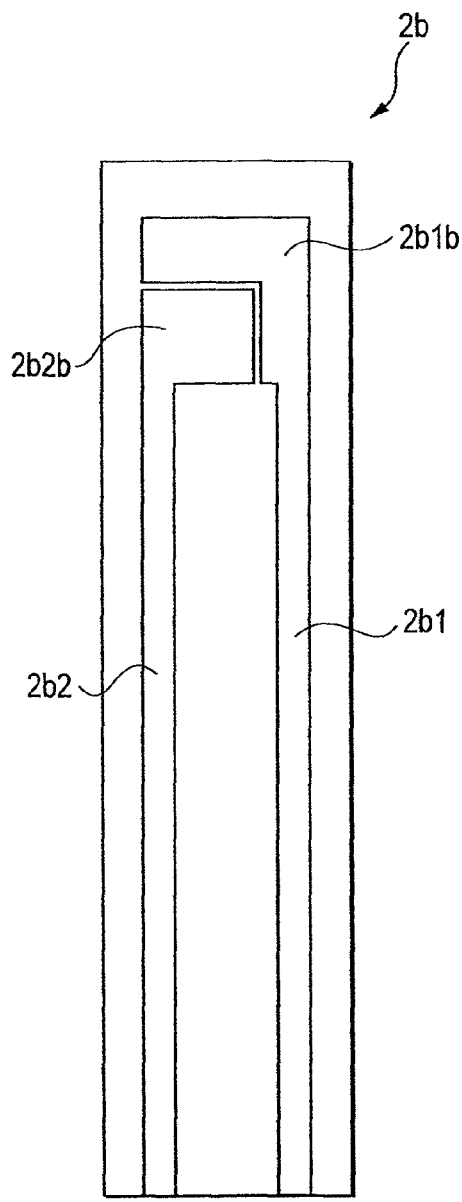
FIG. 27 shows a front or top view of one of the test strips used on the cartridge of FIG. 1.
Figure 28:
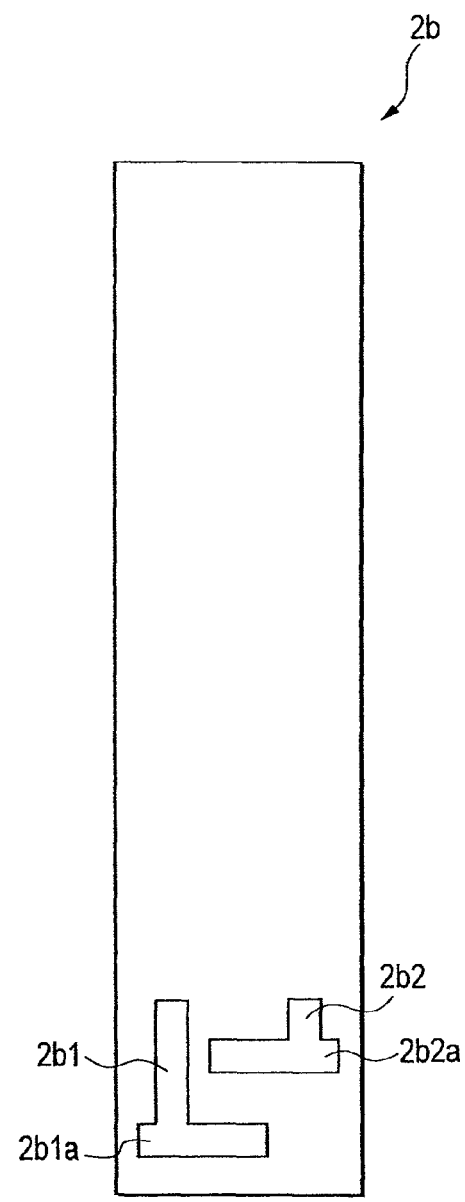
FIG. 28 shows a rear or bottom view the test strip shown in FIG. 27.

FIGS. 27 and 28 shows a front and rear views of one non-limiting embodiment of the test strip 2*b* which can be used on any of the cartridges disclosed herein. Of course, the invention contemplates utilizing conventional test strips provided they are configured for use on a cartridge of the type disclosed herein. The test strip 2*b* utilizes contacts and/or electrodes of the type which are known in the art. However, in the instant embodiment, the test strip 2*b* should utilize contact sections 2*b*2*b* and 2*b*1*b* which are configured to receive thereon a sample of blood or other body fluid. These sections 2*b*2*b* and 2*b*1*b* are electrically connected to rear facing contact pads 2*b*2*a* and 2*b*1*a* via electrode sections 2*b*2 and 2*b*1. The contact pads 2*b*2*a* and 2*b*1*a* are located in a position on the test strips 2*b* so that each contact pad makes electrical contact with the pin contacts 103 and 104 when a particular test strip 2*b* is moved to a needle triggering position, e.g., the 3 o'clock position shown in FIGS. 17 and 18.

Figure 29:
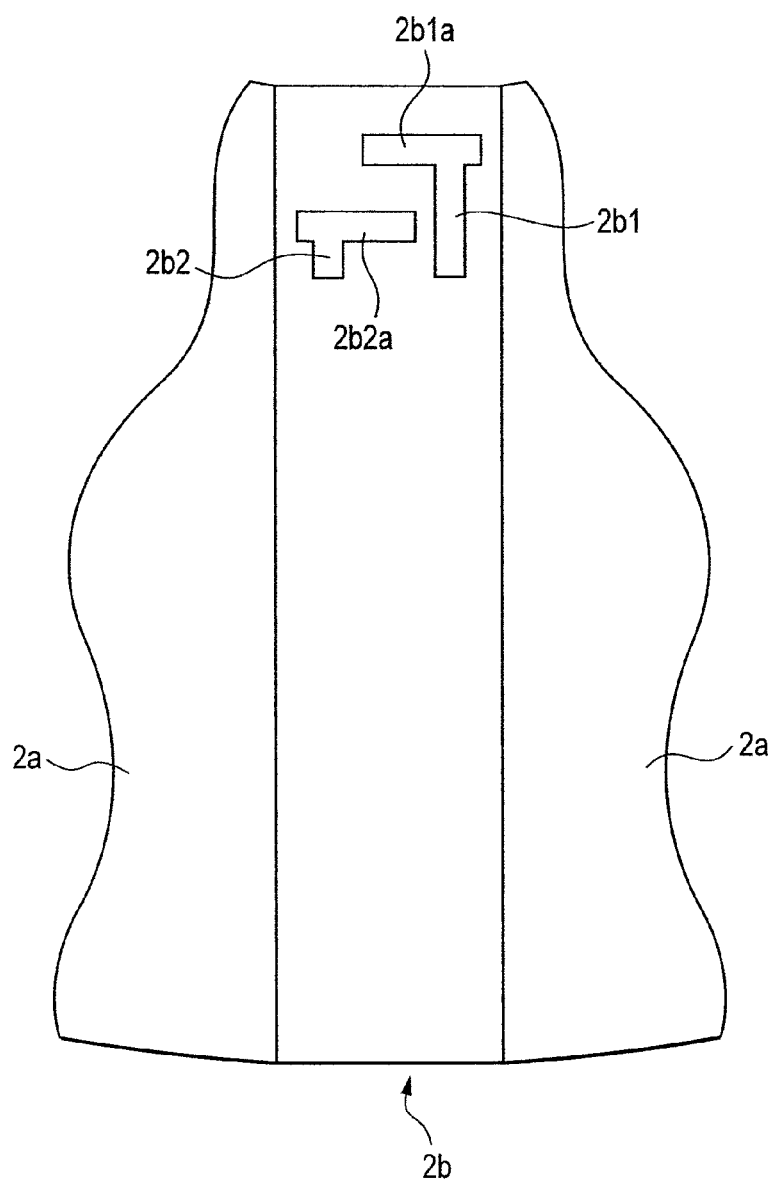
FIG. 29 shows a partial enlarged view of FIG. 4.
Figure 30:
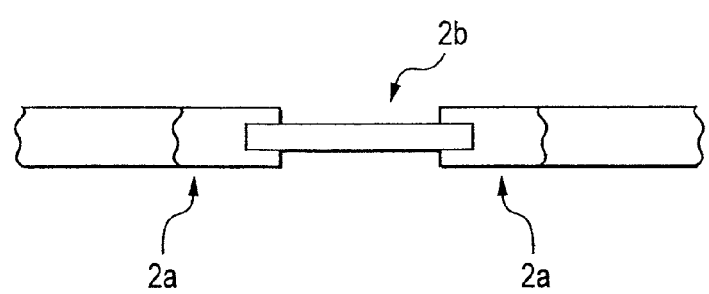
FIG. 30 shows an end view of FIG. 29.

FIGS. 29 and 30 illustrate one non-limiting way in which each of the test strips 2*b* can be connected to and/or arranged on the planar disk body 2. According to this embodiment, each test strip 2*b* is fitted into oppositely arranged grooves formed in the sections 2*a* which make up the disk body 2. In this regard, the side edges of the test strips can be secured to the grooves via a press fit, snap connection, by ultrasonic welding, and even using an adhesive and/or bonded connection. Of course, the invention also contemplates arranging the test strips 2*b* on the disk body 2 in other ways. The test strips 2*b* can also be integrally formed with the body 2 and/or the sections 2*a* which make up the body 2.

Figure 31:
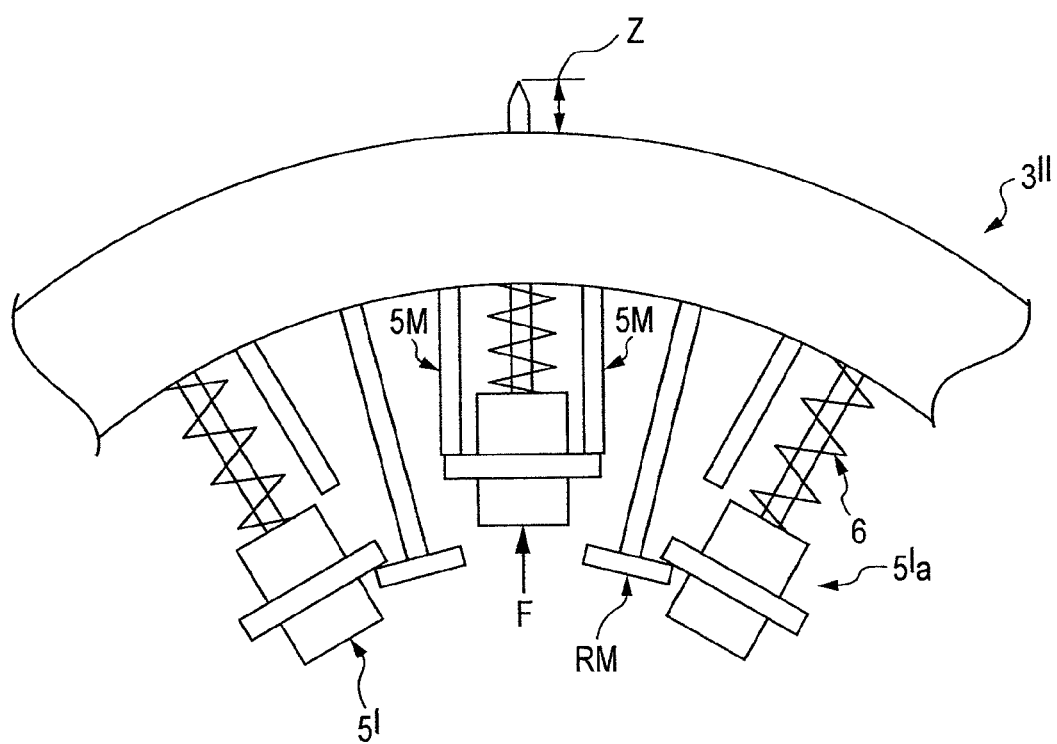
FIG. 31 shows a partial top view of another embodiment of an assembly including a lancet needle holding ring and lancet needles. This arrangement is similar to that of FIG. 26 but additionally includes a plurality of radially oriented stop members which ensure that the lancet needles do not penetrate beyond a predetermined amount.

FIG. 31 illustrates another embodiment of a lancet needle holding ring 3" and needles 5' which can be used on any of the cartridges disclosed herein. The ring 3" is similar to ring 3' shown in FIG. 26 except that it also includes a plurality of lancet needle stop members SM. The stop members SM can be cylindrical wall sections and/or parallel wall members and can be generally radially arranged and equally angularly spaced. Each stop member SM has one end coupled to an inner cylindrical surface of the ring 3" and a free end which engages with portion of a flange of the head 5'*a* of the lancet needles 5'. This arrangement thus provides for the combination of a plurality of radially oriented retaining members RM which ensure that the lancet needles 5' remain mounted to the lancet needle holding ring 3' when the cartridge is removed from the testing device and the stop members SM which ensure that the lancet needles 5' penetrate a predetermined amount or depth setting "z". The depth setting "z" is reached when a force "F" is applied to portion 5'*a* as shown in FIG. 31. By manufacturing different cartridges based on their different length stop members SM, a user can select a cartridge based on a desired depth setting "z" from a number of cartridges. It is envisioned that between 2 and 6 cartridge types can be made having different depth settings based on the length of the stop members SM and the user can select one for use on a testing device based on the desired depth setting "z". The retaining members RM and stop member SM can be integrally formed with the ring 3". Of course, this ring 3" and needle 5' arrangement can be used on any of the cartridge embodiments disclosed herein.

Figure 32:
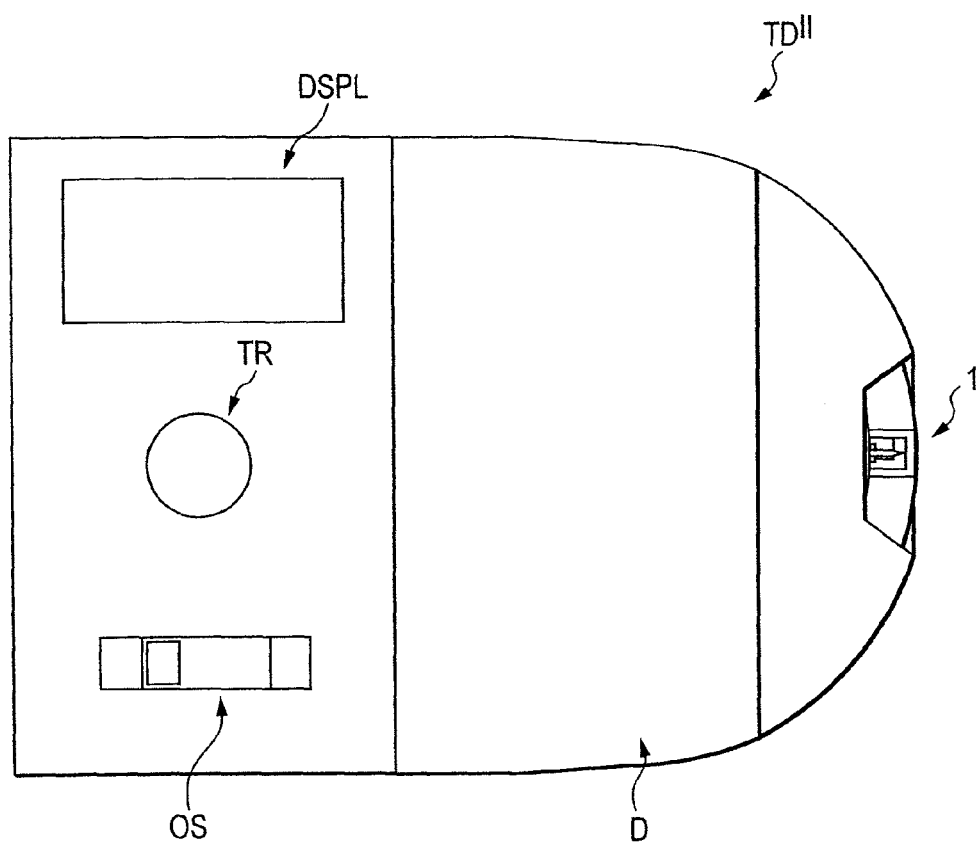
FIG. 32 shows a top view of another embodiment of a testing device. The device is similar to the one shown in FIG. 21, except that the door had been modified to expose less of the cartridge. The test device includes, among other things typically utilized on a test device or glucose meter, a display, a trigger and an on-off switch.

FIG. 32 shows a top view of another embodiment of a testing device TD". The testing device TD" is similar to the one shown in FIG. 21, except that the door D had been modified to expose less of the cartridge 1. The test device TD" includes, among other things typically utilized on a test device or glucose meter, a display DSPL, a trigger TR and an on-off switch OS.

Figure 33:
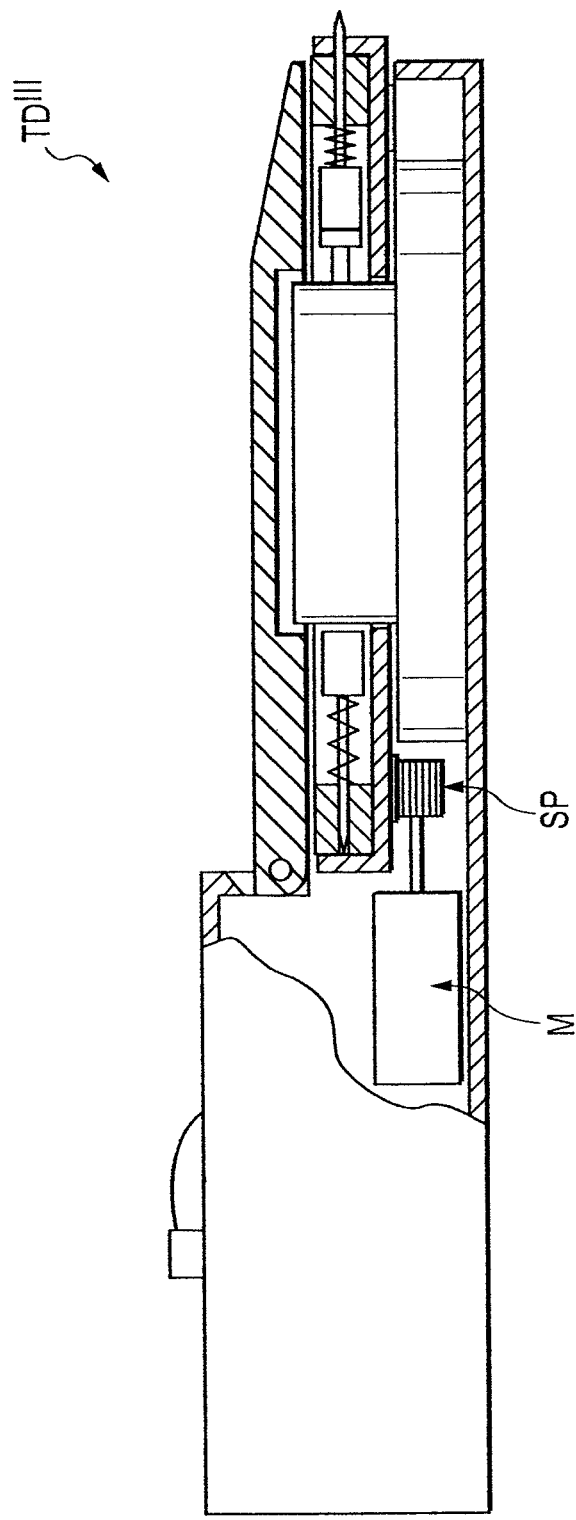
FIG. 33 shows a side view of another embodiment of a testing device. The testing device is similar to the one shown in FIG. 23, except that it utilizes a system for electronically indexing the cartridge between each of the various angular positions, i.e., the cartridge is automatically caused to rotate to the next position once a user receives a testing result. The system uses an electric motor which can be operated by the processor of the testing device and/or switched on by a manual switch. One of the lancet needles is shown in the extended position after the test device has been triggered.

FIG. 33 shows a side view of another embodiment of a testing device $TD^{111}$. The testing device $TD^{111}$ is similar to the one shown in FIG. 23, except that it utilizes a system for electronically indexing the cartridge 1' between each of the various angular positions, i.e., the cartridge 1' is automatically caused to rotate to the next position once a user receives a testing result. The system uses an electric motor M which can be operated by the processor of the testing device $TD^{111}$ and/or switched on by a manual switch. Of course, any type of electric motor can be utilized such as a motor operated electronically. The motor can also be replaced by an actuator such as a linear actuator, a piezoelectric actuator, a linear shape memory alloy (SMA) actuator, or even a magnetic shape memory (MSM) actuator. By way of non-limiting example, once a lancet needle is moved to the extended position after the test device has been triggered and once the testing result is produced, the testing device $TD^{111}$ can execute a time delay of a few second before causing the motor M to index the cartridge 1' to the next position. In order to cause the indexing movement, the motor M uses a sprocket SP which engages with a circular section of radially arranged grooves and teeth arranged on the lower surface of the cartridge 1'. Of course, this sprocket/tooth engagement can be replaced with any desired high-friction engagement provided that a reliable engagement is provided. Moreover, although the motor M indexing system is shown being utilized with regard to the second cartridge embodiment, such an arrangement can also be utilized with the first cartridge embodiment as well as on any of the testing devices disclosed herein. The benefit of such an indexing system is, of course, that it eliminates the need for the user to manually index the cartridge in the testing device.

Figure 34:
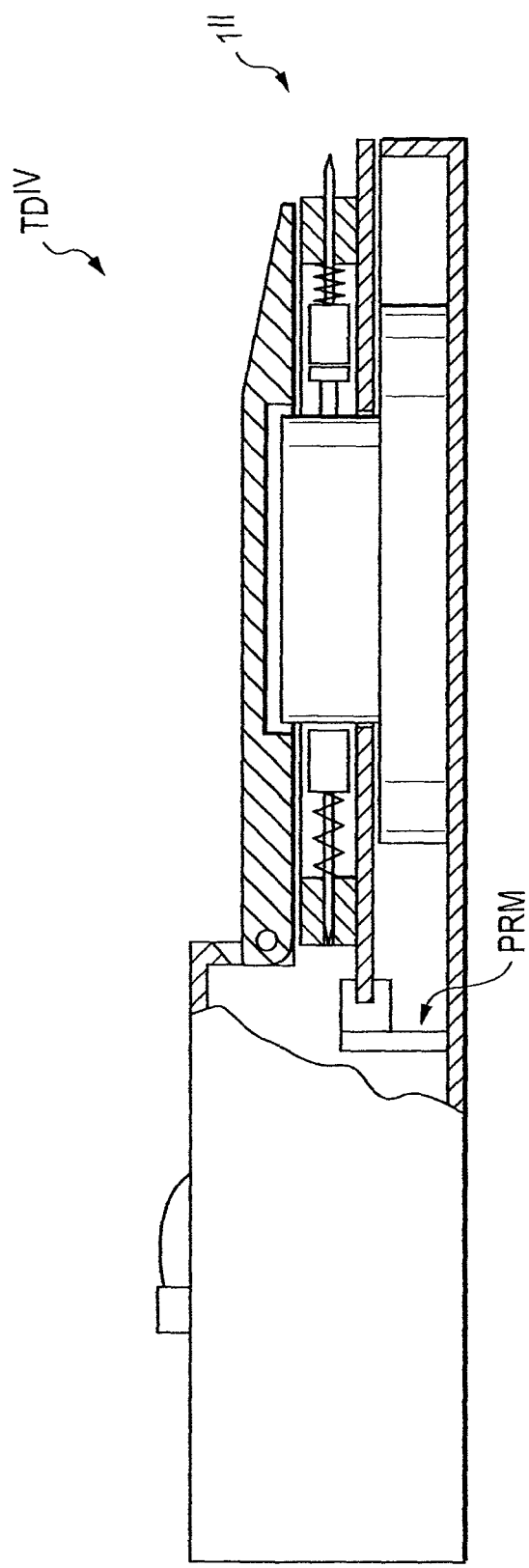
FIG. 34 shows a side view of another embodiment of a testing device. The testing device is similar to the one shown in FIG. 22, except that it utilizes a system for securing the cartridge in each of the various angular positions, i.e., the cartridge is temporarily locked in each of the various positions. The system uses a deflecting position retaining member which engages with each of a plurality of circumferential notches in the cartridge. One of the lancet needles is shown in the extended position after the test device has been triggered.
Figure 35:
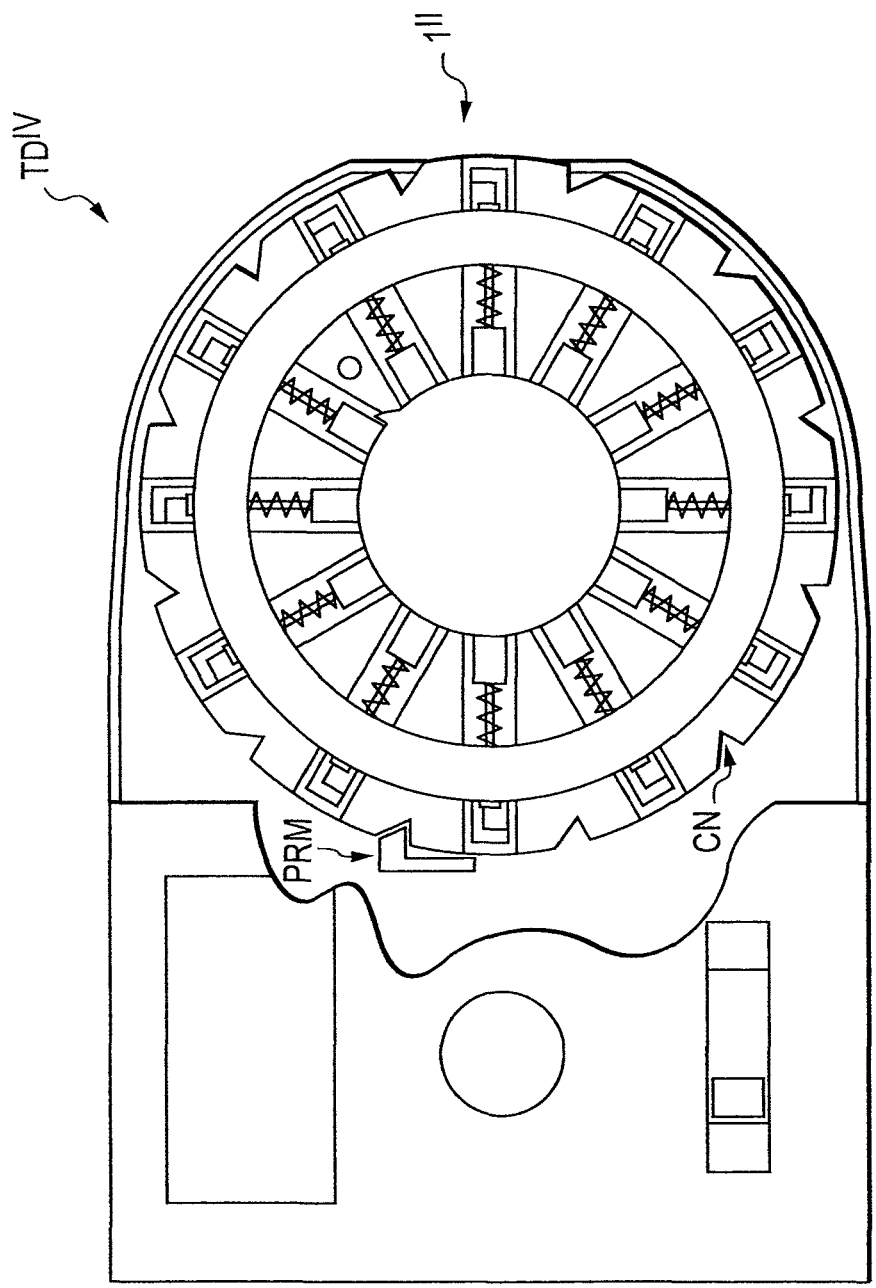
FIG. 35 shows a top view of the testing device of FIG. 34. The Figure shows the position retaining member engaging with one of the plurality of circumferential notches of the cartridge.
Figure 36:
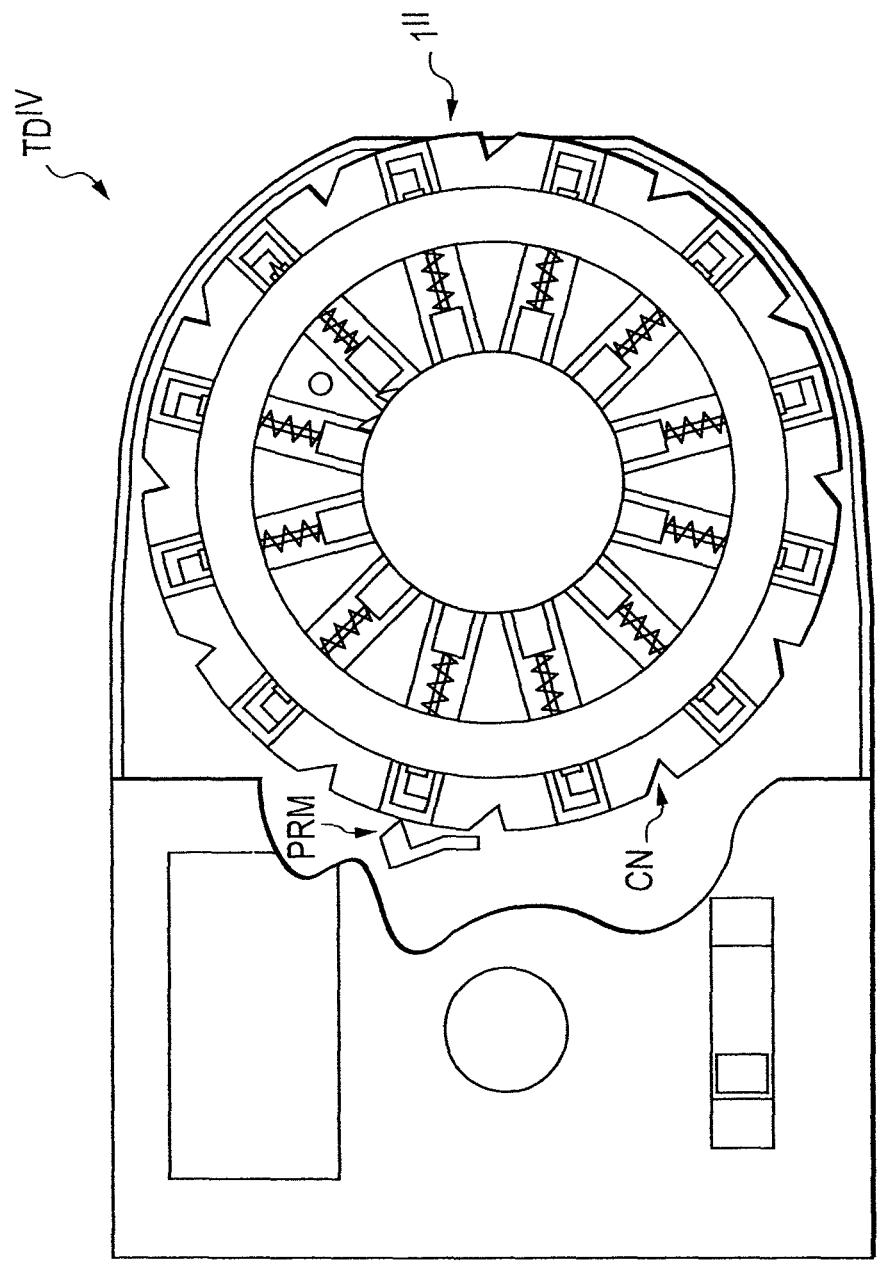
FIG. 36 shows another top view of the testing device of FIG. 34. The Figure shows the position retaining member being deflected as the cartridge is moved to another position wherein it will engage with one of the plurality of circumferential notches of the cartridge. The Figure also shows how the alignment projection of the mounting arrangement engages with the lancet needles as the cartridge is rotated.

FIGS. 34-36 show another embodiment of a testing device $TD^{IV}$ and a third embodiment of the cartridge 1". The testing device $TD^{IV}$ is similar to the one shown in FIG. 22, except that it utilizes a system for securing the cartridge 1" in each of the various angular positions, i.e., the cartridge 1" is temporarily locked in each of the various positions. The system uses a deflecting position retaining member PRM which engages with each of a plurality of circumferential notches CN in the cartridge 1". The member PRM has one end which is coupled to a wall of the testing device housing and a free end which releasably engages with each of the notches CN. The arrangement is such that when the member PRM engages with one of the notches CN, the lancet needle and test strip are properly aligned and ready to be used (see FIG. 35). FIG. 36 shows the position retaining member PRM being deflected as the cartridge 1" is moved to another position wherein it will engage with one of the plurality of circumferential notches CN of the cartridge 1". The design of the notches CN is such that they prevent the cartridge 1" from being rotated clockwise, i.e., they also serve as a one-way rotation mechanism. Of course, this indexing arrangement can be used on any of the cartridges and testing devices disclosed herein including one which also utilizes the indexing motor M of FIG. 33.

Figure 37:
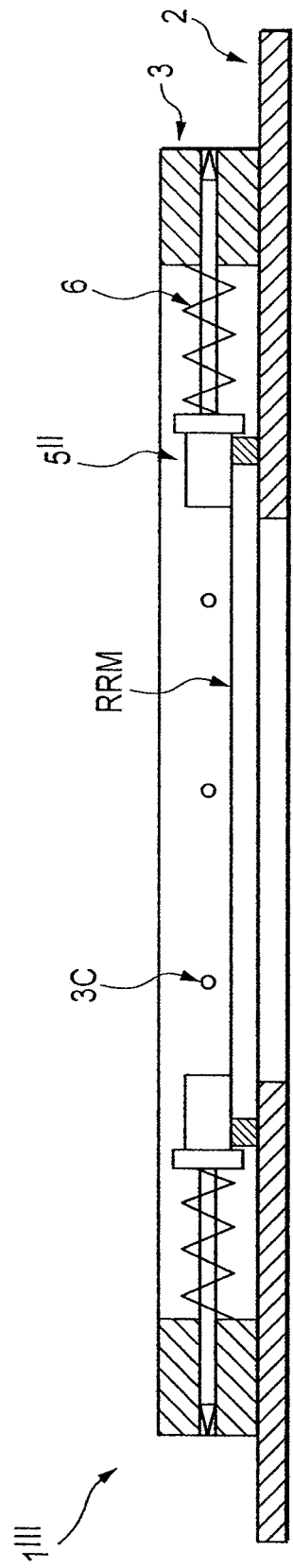
FIG. 37 shows a cross-section view of another embodiment of an assembly including a lancet needle holding ring and lancet needles. This arrangement provides for a retaining ring member which ensures that the lancet needles remain mounted to the lancet needle holding ring. The cartridge can be used on any of the testing devices shown in FIGS. 9-22, 32 and 34-36. The retaining ring member and lancet needles can also be used on the cartridges shown in FIGS. 23-25 and 33.

FIG. 37 shows a cross-section view of another embodiment of an assembly, i.e., a cartridge $1^{111}$ which includes a lancet needle holding ring 3 and lancet needles 5". This arrangement provides for a generally circular retaining ring member RRM which ensures that the lancet needles 5" remain mounted to the lancet needle holding ring 3. The lancet needles 5" are similar to those of FIGS. 5a-c except that they include a circular flange which engages with the member RRM. The ring RRM can, in particular, be used in place of the retaining members RM shown in FIGS. 26 and 31. The cartridge $1^{111}$ can be used on any of the testing devices shown in FIGS. 9-22, 32 and 34-36. The retaining ring member RRM and lancet needles 5" can also be used on the cartridges shown in FIGS. 23-25 and 33.

Figure 38:
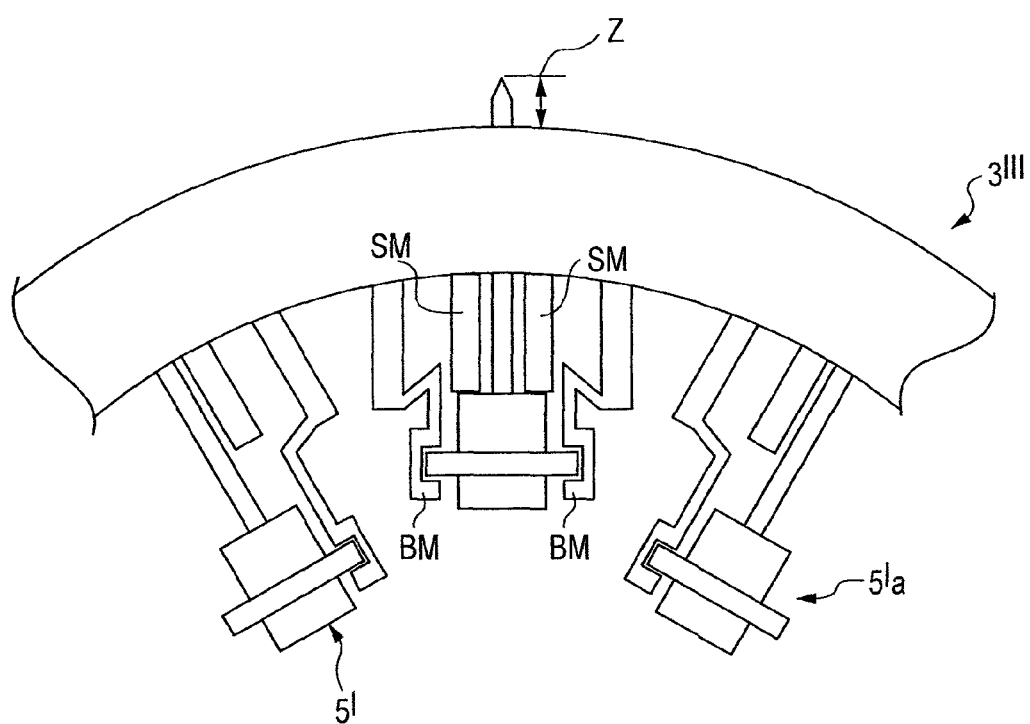
FIG. 38 shows a partial top view of another embodiment of an assembly including a lancet needle holding ring and lancet needles. This arrangement is similar to that of FIG. 26 but additionally includes a plurality of radially oriented stop members which ensure that the lancet needles do not penetrate beyond a predetermined amount and biasing members in place of the lancet needle springs.

FIG. 38 illustrates another embodiment of a lancet needle holding ring $3^{111}$ and needles 5' which can be used on any of the cartridges disclosed herein. The ring $3^{111}$ is similar to ring 3' shown in FIG. 26 except that it also includes a plurality of lancet needle stop members SM and, in place of the springs 6, biasing members BM are used to bias the lancet needles towards a resting and/or initial position. The stop members SM can be cylindrical wall sections and/or parallel wall members and can be generally radially arranged and equally angularly spaced. Each stop member SM has one end coupled to an inner cylindrical surface of the ring $3^{111}$ and a free end which engages with portion of a flange of the head 5'a of the lancet needles 5'. This arrangement thus provides for the combination of a plurality of radially oriented biasing members BM which ensure that the lancet needles 5' remain mounted to the lancet needle holding ring $3^{111}$ when the cartridge is removed from the testing device and the stop members SM which ensure that the lancet needles 5' penetrate a predetermined amount or depth setting "z". By manufacturing different cartridges based on their different length stop members SM, a user can select a cartridge based on a desired depth setting "z" from a number of cartridges. It is envisioned that between 2 and 6 cartridge types can be made having different depth settings based on the length of the stop members SM and the user can select one for use on a testing device based on the desired depth setting "z". The biasing members BM and stop member SM can be integrally formed with the ring $3^{111}$. Of course, this ring $3^{111}$ and needle 5' arrangement can be used on any of the cartridge embodiments disclosed herein.

The operation of a testing device using a cartridge of the type described herein will now be explained with reference to the embodiment shown in FIGS. 19-22. As an initial step, the user will open the door D and install the cartridge 1 onto the mounting arrangement MA. This is accomplished by aligning the notch 8 with the projection 108. The user can then force the cartridge 1 downwards until the bottom surface of the disk 2 contacts the surface 105. The user can then close the door D and begin using the device by switching on the testing device TD, placing a finger FNG in the position shown in FIG. 22, and triggering the testing device TD to cause one of the lancet needles to puncture the finger FNG. The user will then rotate the finger to place a blood drop on the exposed end of the test strip. At this point, the device can function to automatically provide a test result after triggering and sensing the blood drop on the test strip, or upon the user manually inputting a request for testing by, e.g., pushing the trigger TR a second time to activate the testing procedure. Once the user has received a result, the user can then manually rotate the cartridge 1 by, e.g., applying a rubbing force on the edge OE, or as is preferred, by activating the indexing motor M. This activation can occur automatically (i.e., after a time delay) or by, e.g., the user pressing the trigger button TR a third time. The device will then be ready for use again at a later time and/or by a different user.

FIGS. 39-46b show still another non-limiting embodiment of a cartridge 10. The cartridge 10 includes a disk-shaped planar body 20 and a lancet needle retaining ring 30. A plurality of lancet needles 50 are mounted to the ring 30 radially.

Figure 52:
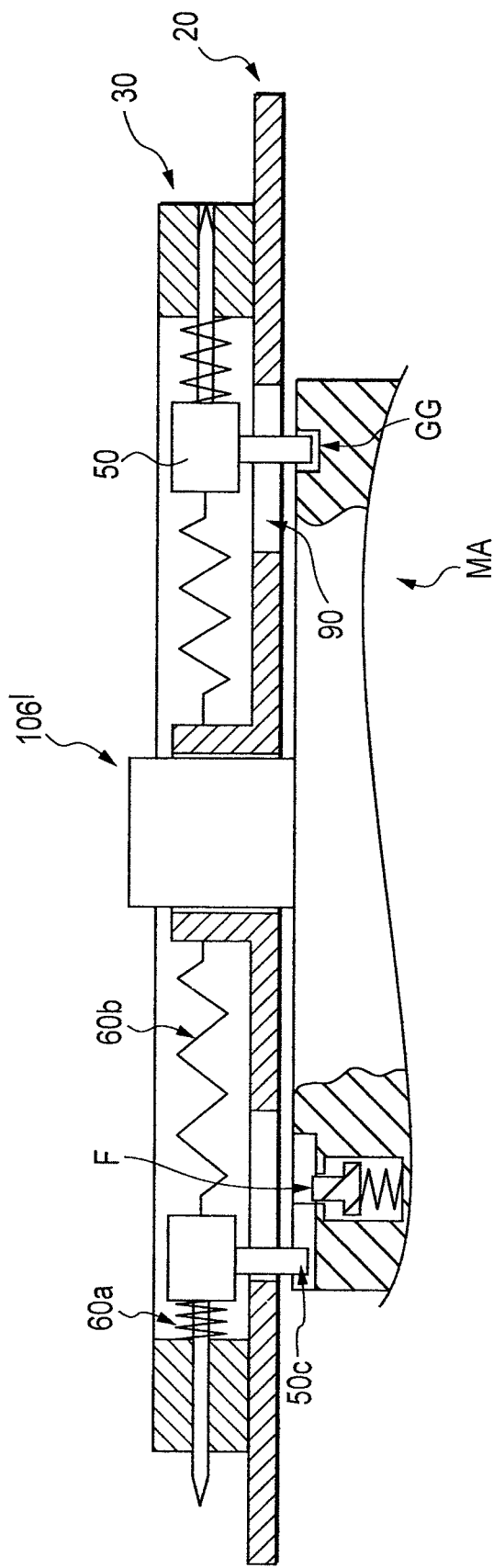
FIG. 52 shows a side cross-section view showing the cartridge of FIG. 39 installed on the mounting arrangement of FIG. 48. The lancet needle located at the position of the trigger release mechanism is shown having moved to the fully extended position after the trigger release mechanism has moved to the trigger release or triggered position.

Each lancet needle 50 has a cylindrical needle portion 50b, an enlarged head portion 50a, and a projecting portion 50c, which projects through and slides within a slot 90, and which can be engaged, contacted and/or movably guided by a mechanism (e.g., having the form of a guiding groove or recess) which causes the lancet needle 50 to extend beyond the ring 30 (see e.g., FIG. 52). Each lancet needle 50 is movably mounted within a radially oriented opening 30c formed in the ring 30. An inner spring 60b and an outer spring 60a is mounted to each lancet needle 50 in order to ensure that the lancet needle 50 automatically expands and retracts once the lancet needle 50 is triggered. Thus, spring 60b causes the lancet needle 50 to move to an extended puncturing position and spring 60a, which is substantially weaker than spring 60b, causes the lancet needle to move to a retracted or resting position after the lancet needle 50 reaches the fully extended position. Each lancet needle 50 is linearly guided by a slot 90 formed in the disk-shaped member 20. The internal stop surfaces of the slot 90 define the maximum extended position of the lancet needles 50 as well as the maximum retracted position of the lancet needles 50.

A plurality of test strips 20b are also radially arranged and are generally aligned with the lancet needles 50. By way of non-limiting example, the disk-shaped body 20 can have an outer diameter of between approximately 1.0" and 3" and is preferably between approximately 1.5" and approximately 2" in diameter. The cylindrical needle portion 50b of the lancet needles 50 can be made of metal such as stainless steel and can also be of the same material and diameter as conventional lancet needles. The cylindrical head portion 50a can have a diameter of between approximately 0.05" and approximately 0.15" and can be made of a synthetic resin material which is injected molded onto the cylindrical portion 50b. The springs 60a and 60b can be of any desired type and can preferably be a wire compression springs. The test strips 20b can be in the range of between approximately 0.10" and approximately 0.25" in width, approximately 0.025" and approximately 0.1" in thickness and between approximately 0.5" and approximately 1.25" long.

Figure 39:
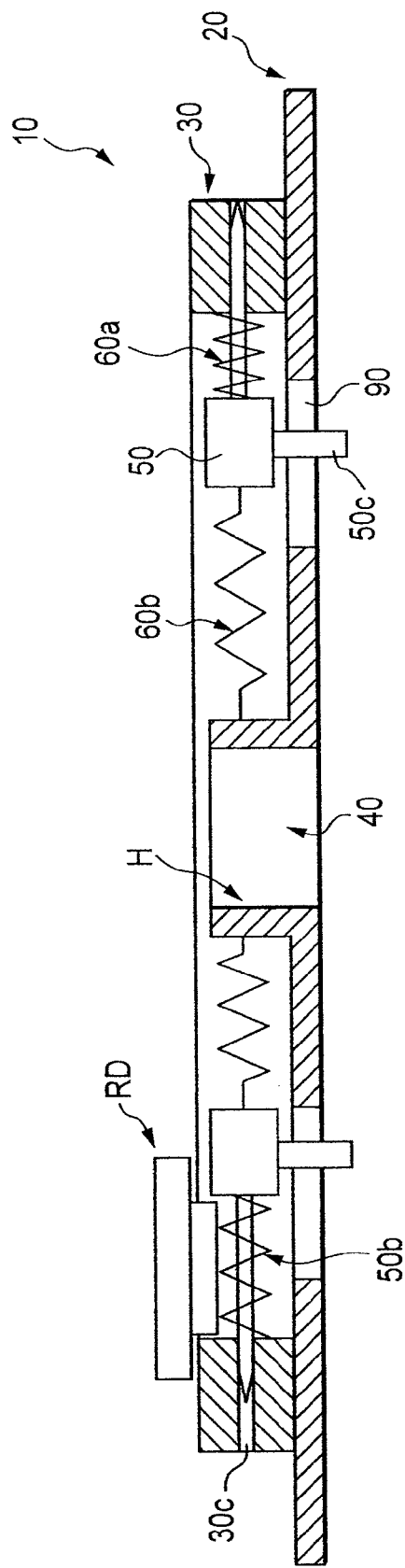
FIG. 39 shows a cross-section view of another embodiment of a cartridge. For the sake of clarity, only the lancet needles positioned at three o'clock and nine o'clock are shown installed on the cartridge. The lancet needles, the springs and the retaining device are not shown in cross-section.
Figure 40:
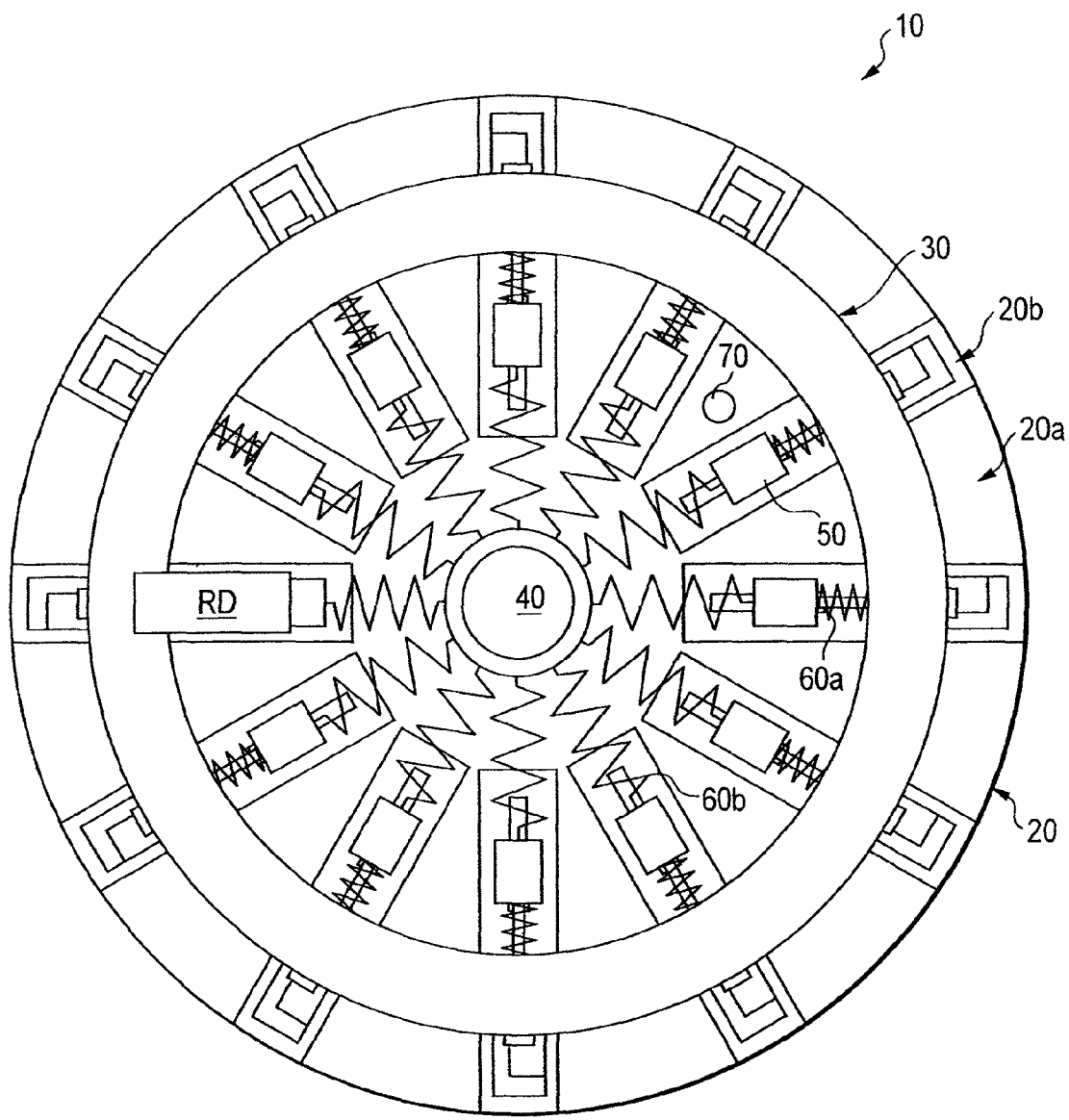
FIG. 40 shows a top view of the cartridge shown in FIG. 39. The contact strips of the test strips extending inwardly from the lancet needle support ring are not shown.
Figure 41:
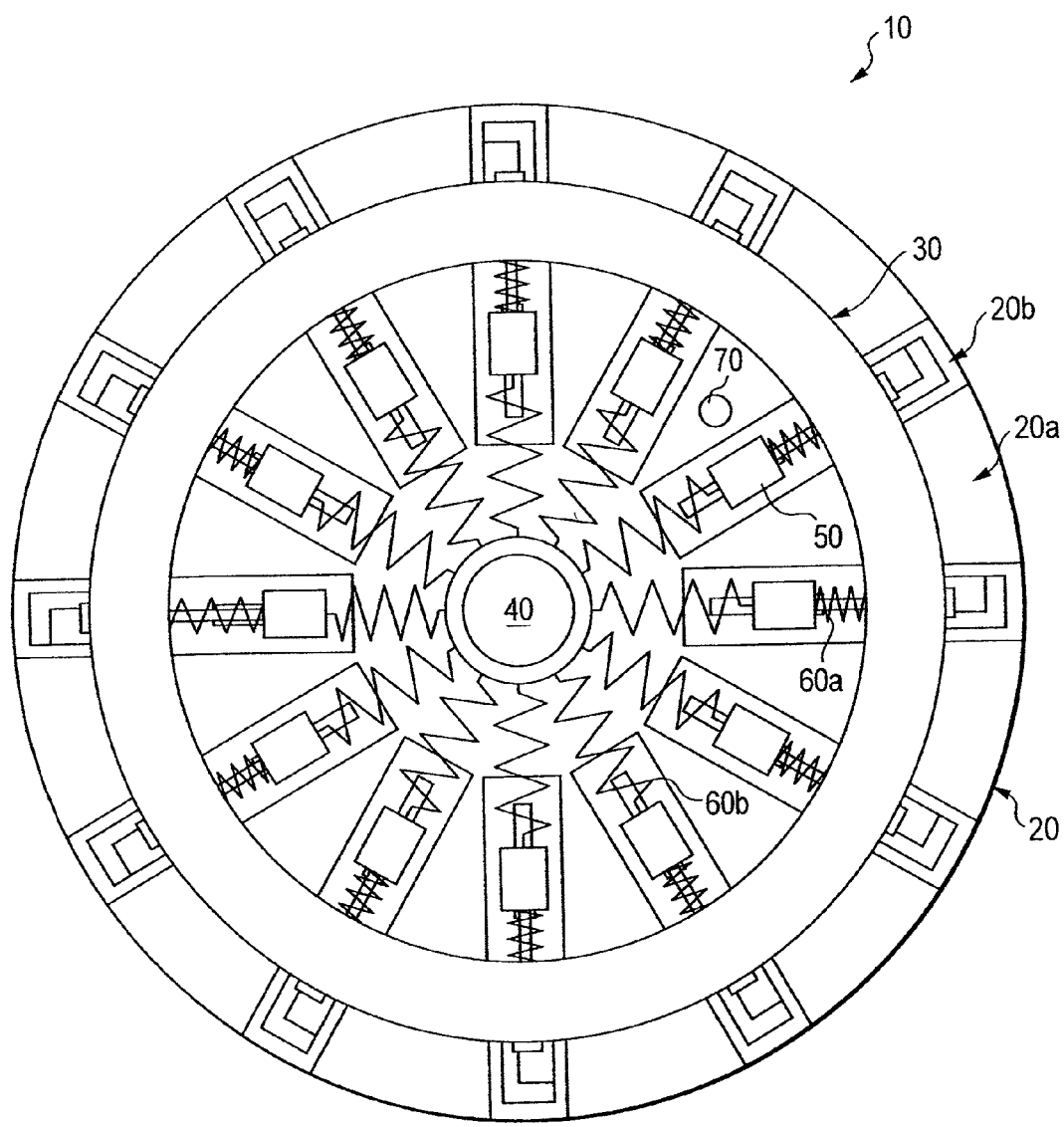
FIG. 41 shows a top view of the cartridge shown in FIG. 40 with the retaining device being removed. The lancet needle at the nine o'clock position has not yet moved to rest position of the other lancet needles.
Figure 42:
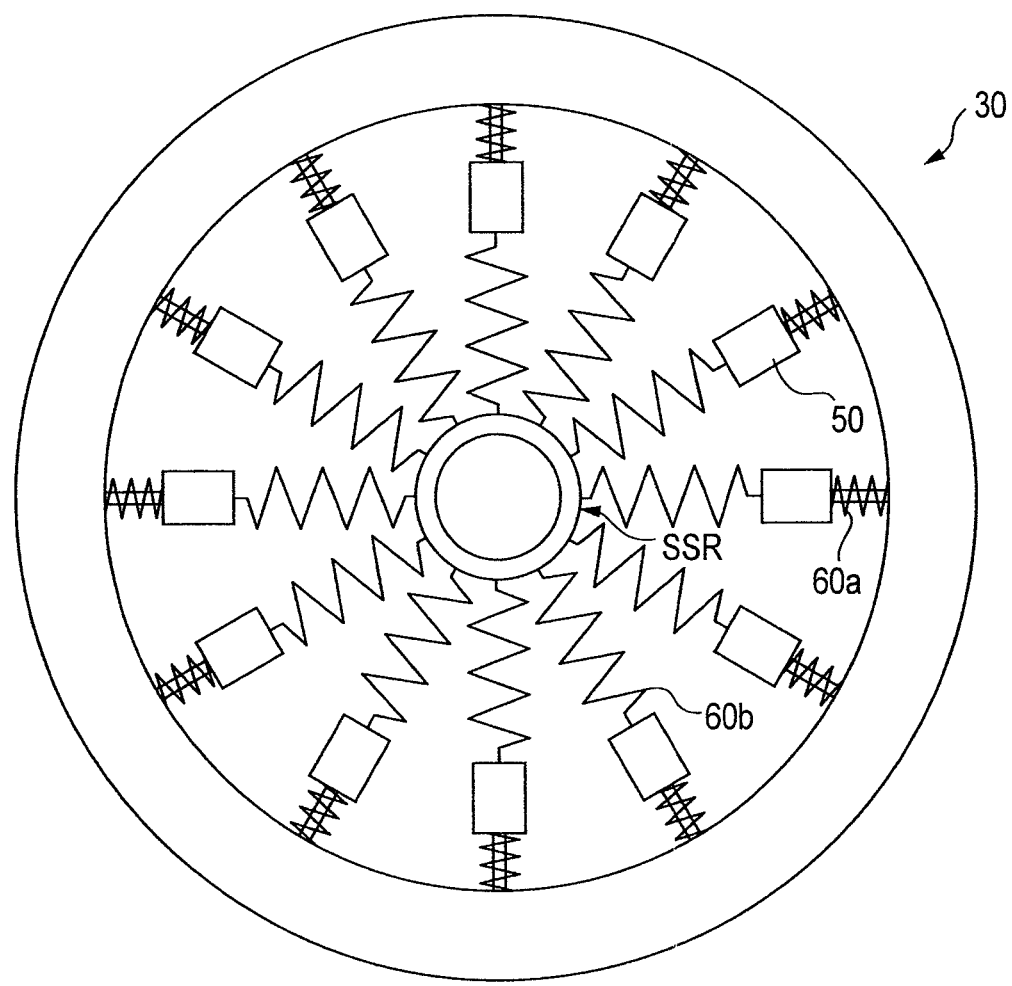
FIG. 42 shows a top view of the lancet needle support ring and the lancet needles used in the embodiment of FIG. 39.
Figure 43:
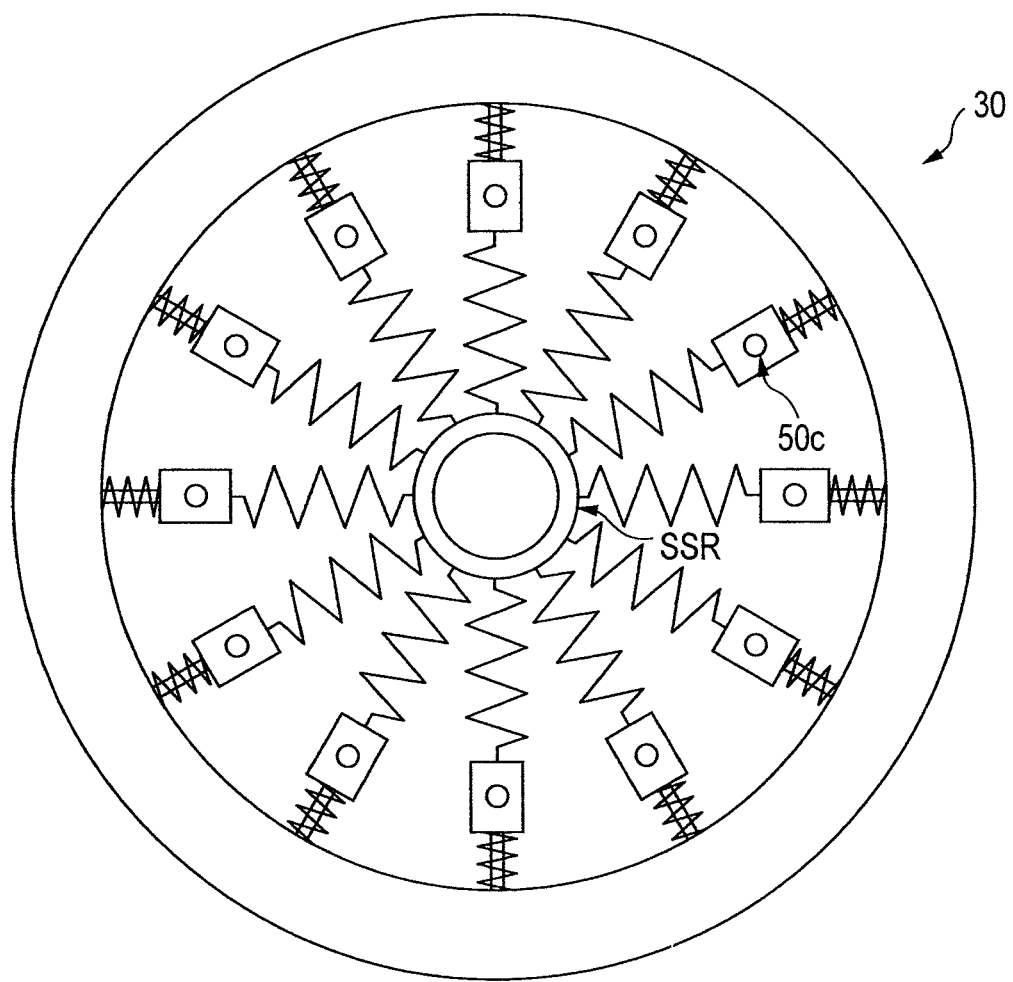
FIG. 43 shows a bottom view of the lancet needle support ring and the lancet needles used in the embodiment of FIG. 39.

As can be seen in FIG. 39, the cartridge 10 utilizes a centrally disposed cylindrical opening 40 which is defined by a hub portion H of the disk-shaped member 20 and which allows the cartridge 10 to be mounted to a mounting arrangement MA (see FIGS. 48-52) of a testing device. Of course, the cartridge 10 can have a variety of designs in order to allow it to be mounted to any number of testing devices. In order to ensure that the cartridge 10 is installed in a desired predetermined position of a mounting arrangement MA, the cartridge 10 can include an alignment mechanism (not shown but similar to the mechanism 8 shown in FIG. 1). This alignment mechanism can have the form of a notch which slides over a projection of the mounting arrangement MA thereby ensuring that the cartridge 10 can only be installed when oriented in a single angular position. In order to ensure that the cartridge 10 will rotate or index in only a single time, i.e., only 360 degrees, the cartridge 10 includes a locking mechanism 70. This locking mechanism 70 can have the form of an opening within which a pin (not shown but similar to pin 101 of the mounting arrangement MA shown in FIG. 9) extends when the cartridge 10 rotates a full 360 degrees from an originally installed position. Once the pin engages the opening 70, the user will know that the cartridge 10 has been fully used, i.e., the user will be able to discern that all of the test strips 20b and lancet needles 50 have been used once and that it is time to remove the cartridge 10, discard it, and replace it with a fresh cartridge 10. In order to remove the cartridge 10, the user can simply lift the cartridge 10 out of the mounting arrangement MA slightly, rotate it counter-clockwise one indexing position until the notch is aligned with the projection, and then lifting it completely out of the mounting arrangement MA. This removal process can also be facilitated by the user pressing down, using either a tool or a finger, on the pin which is biased upwards by a spring.

In order to ensure that the cartridge 10 is properly installed onto the mounting arrangement MA, the cartridge 10 can include a removable retaining device RD which ensures that the lancet needle 50 at the, e.g., 3 o'clock position, is partially retracted. This ensures that all of the projecting portions 50c are in the correct position for insertion with the guiding groove GG of the mounting arrangement MA. The retaining device RD can be removed and discarded once the cartridge 10 is installed onto the mounting arrangement MA and is preferably made of an inexpensive synthetic resin material. Of course, the retaining device RD can have any desired configuration and can even have the form of a ring which maintains a desired position of all of the lancet needles 50 in order to ensure that the projecting portions 50c correctly and easily mate with the guiding groove GG of the mounting arrangement MA.

Figure 44:
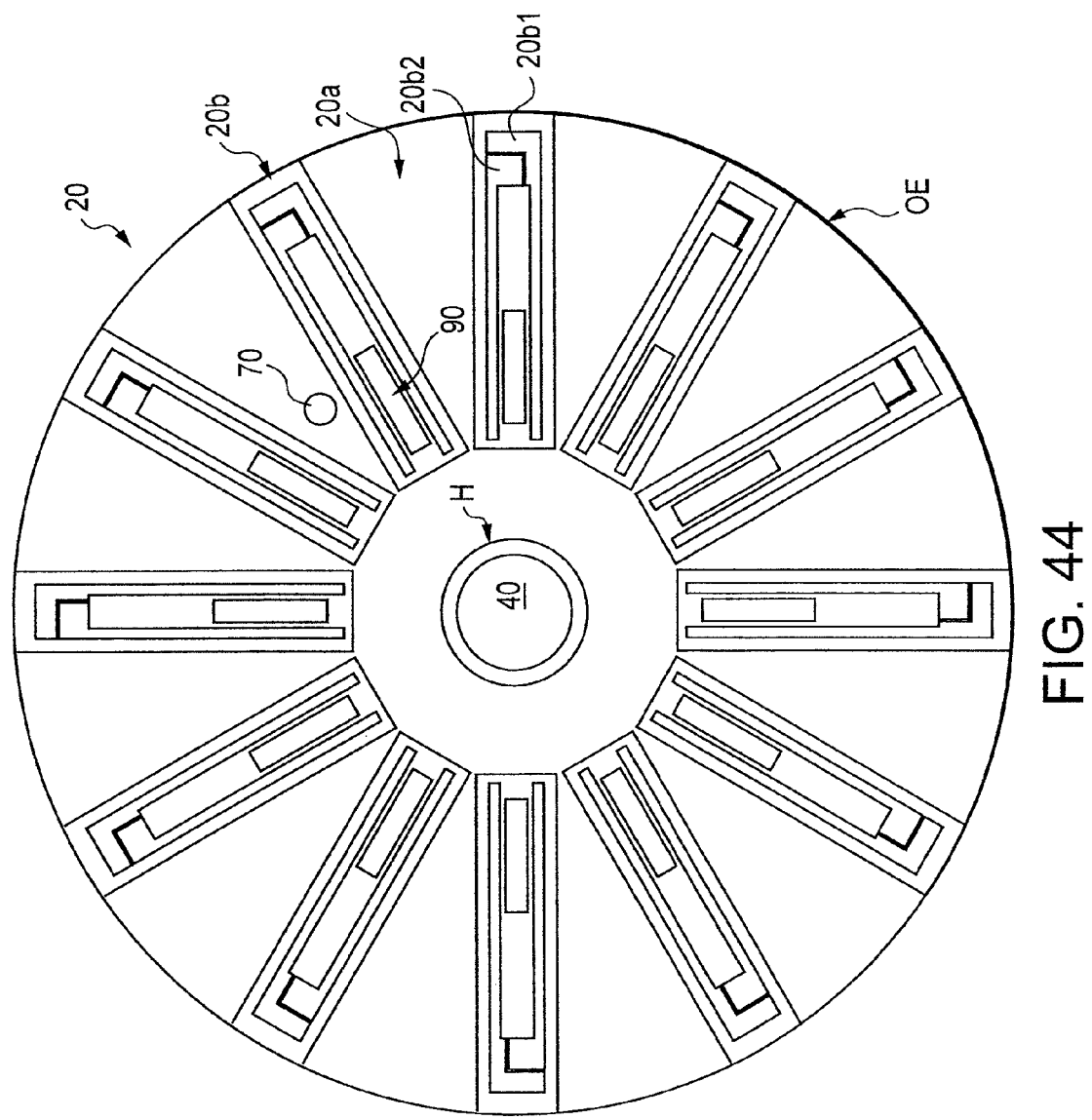
FIG. 44 shows a top view of the cartridge of FIG. 39 with the lancet needle support ring and the lancet needles removed therefrom.

As can be seen in FIG. 44, the test strips 20b include electrical contacts 20b1 and 20b2. In the upper surface of the body 20, the contacts 20b1 and 20b2 are exposed to a blood drop of the user in an area adjacent the outer circumferential edge OE of the body 20. The arrangement of contacts on a test strip which will receive a blood drop is, of course, conventional. The contacts 20b1 and 20b2 extend along the test strip 20b and are electrically connected to contact pads or surfaces arranged on a lower or opposite surface of the body 20 (not shown by similar to the contact pads shown in FIG. 4). These contact pads are positioned to ensure that they provide electrical contact with pin contacts (not shown but similar to the pin contacts 103 and 104 shown in FIG. 9) of the mounting arrangement MA. As the contacts are positioned in only a single location, i.e., at 3 o'clock (see e.g., FIGS. 9-11) on the mounting arrangement MA, an electrical connection is established between a testing device and each test strip 20b only when the test strip 20b is located in a predetermined position and/or triggering position.

Figure 45:
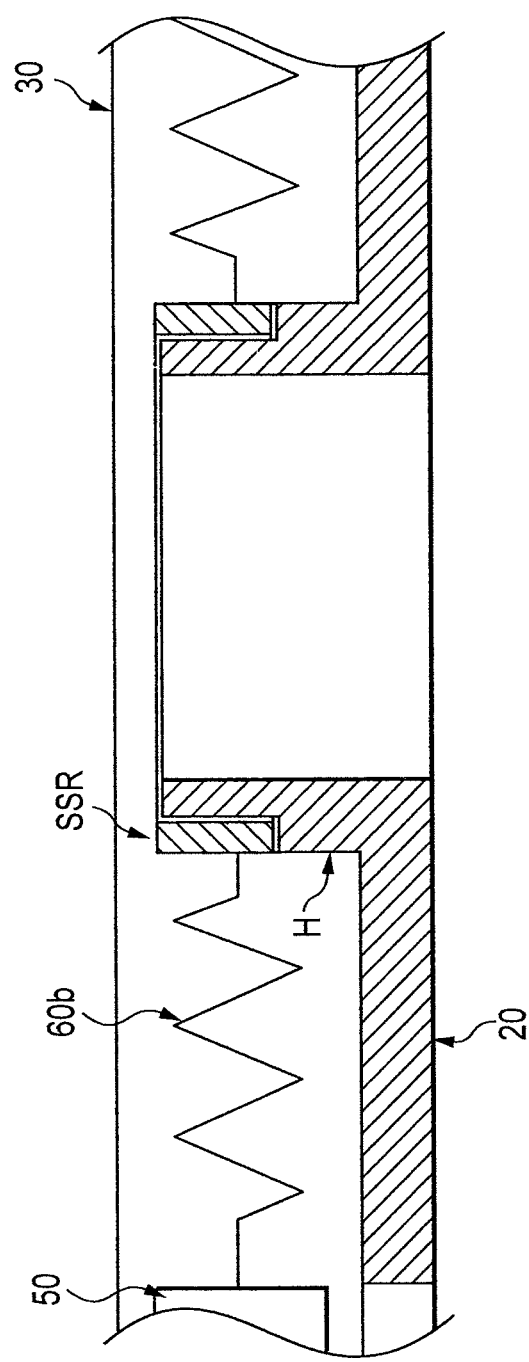
FIG. 45 shows a partial cross-section view of the cartridge of FIG. 39 and shows in detail how the inner springs are coupled to the hub of the disk-shaped member.

As can be seen in FIGS. 45-46b, the larger springs 60b have one end coupled to a respective lancet needle 50 and another end coupled to a spring support ring SSR. The ring SSR is sized to slide over a shoulder portion SP of the hub H. According to the embodiment shown in FIGS. 45-46b, the ends of the springs 60b are non-removably fixed to the lancet needles 50 and the ring SSR.

As can be seen in FIGS. 39-46b, the cartridge 10 is simple is design and construction and includes only seven main parts, i.e., the body 20, the ring 30, the needles 50, the springs 60a and 60b, the support ring SSR, and a retaining device RD. The ring 30 can be a synthetic resin material and can made by injection molding and thereafter provided with the openings 30c by, e.g., drilling. Alternatively, the ring 30 can be made by securing together two pieces each having half-openings formed therein. The ring 30 can be secured to the body 20 by any number of techniques such as bonding, ultrasonic welding, fasteners, snap connections, etc. Although the ring 30 is shown having a generally rectangular cross-section, the invention also contemplates a ring 30 having a square cross-section as well as other shapes. The equally spaced openings 30c are, of course, made to be slightly larger in diameter than the cylindrical portions 50b so that the lancet needles 50 are capable of sliding freely within the openings 30c.

The operation of a testing device using a cartridge of the type shown in FIGS. 39-46b will now be explained. As an initial step, the user will open a door of the testing device and install the cartridge 10 onto the mounting arrangement, e.g., of the type shown in FIGS. 48 and 49. This is accomplished by aligning a notch of the disk-shaped member 20 with a projection of the hub 106'. The user can then force the cartridge 10 downwards until the bottom surface of the disk 20 contacts the surface 105'. The user can then close the door and begin using the device by switching on the testing device, placing a finger (see e.g., FNG shown in FIG. 22) and triggering the testing device to cause one of the lancet needles to puncture the finger. The user will then rotate the finger to place a blood drop on the exposed end of the test strip. At this point, the device can function to automatically provide a test result after triggering and sensing the blood drop on the test strip, or upon the user manually inputting a request for testing by, e.g., pushing the trigger a second time to activate the testing procedure. Once the user has received a result, the user can then manually rotate the cartridge 10 by, e.g., applying a rubbing force on the edge OE, or as is preferred, by activating the indexing motor. This activation can occur automatically (i.e., after a time delay) or by, e.g., the user pressing the trigger button a third time. The device will then be ready for use again at a later time and/or by a different user.

Figure 47A:
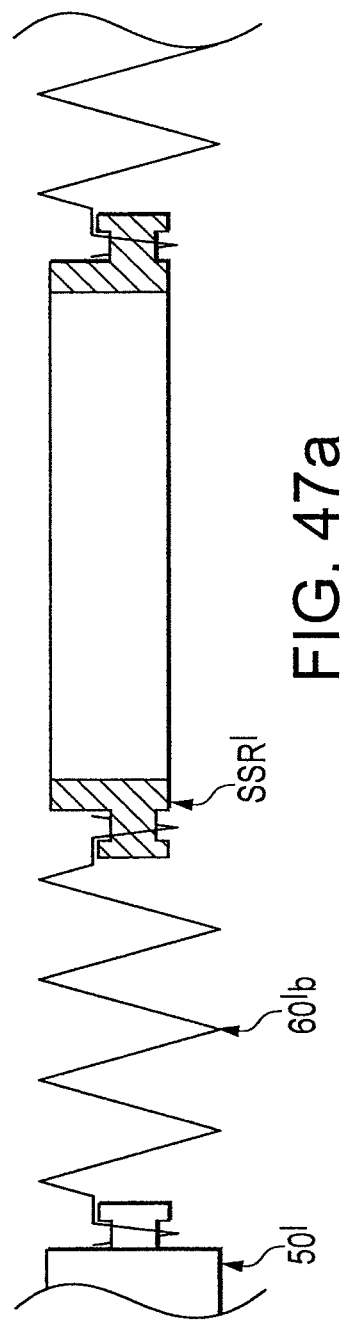
FIGS. 47a and 47b show a partial cross-section view, in a dis-assembled state, of another way in which the spring hub can be connected to the hub of the disk-shaped member.
Figure 47B:
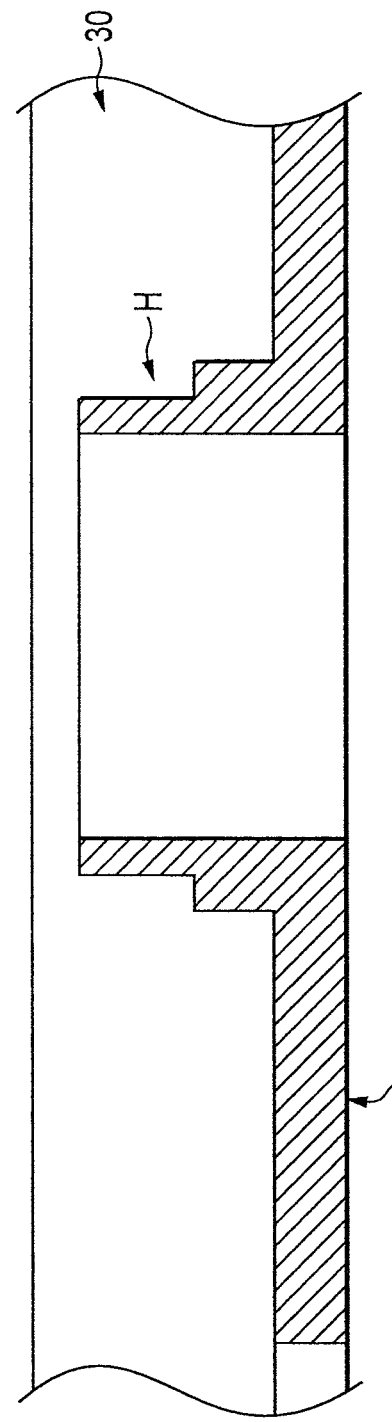

As can be seen in FIGS. 47a and 47b, the larger springs 60'b can also have one end removably coupled to a respective lancet needle 50' and another end coupled to a projecting portion of spring support ring SSR'. As was the case with the previously embodied ring SSR, the ring SSR' is sized to slide over a shoulder portion SP of the hub H.

Figure 48:
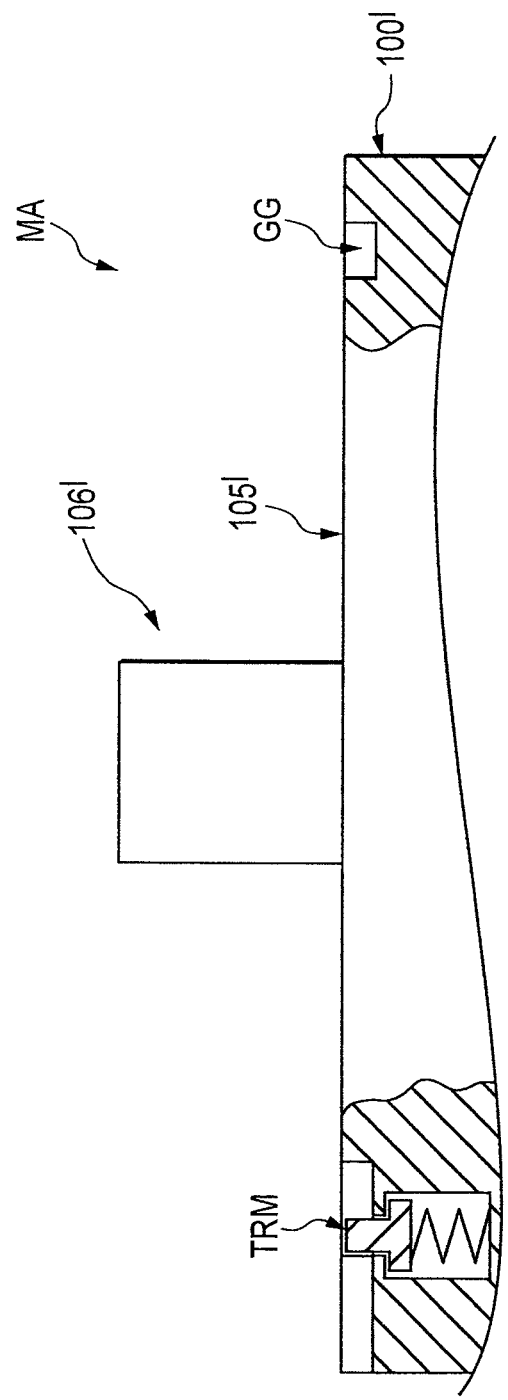
FIG. 48 shows a side view of one embodiment of a mounting arrangement which can be used to mount the cartridge of FIG. 39 in a testing device.
Figure 49:
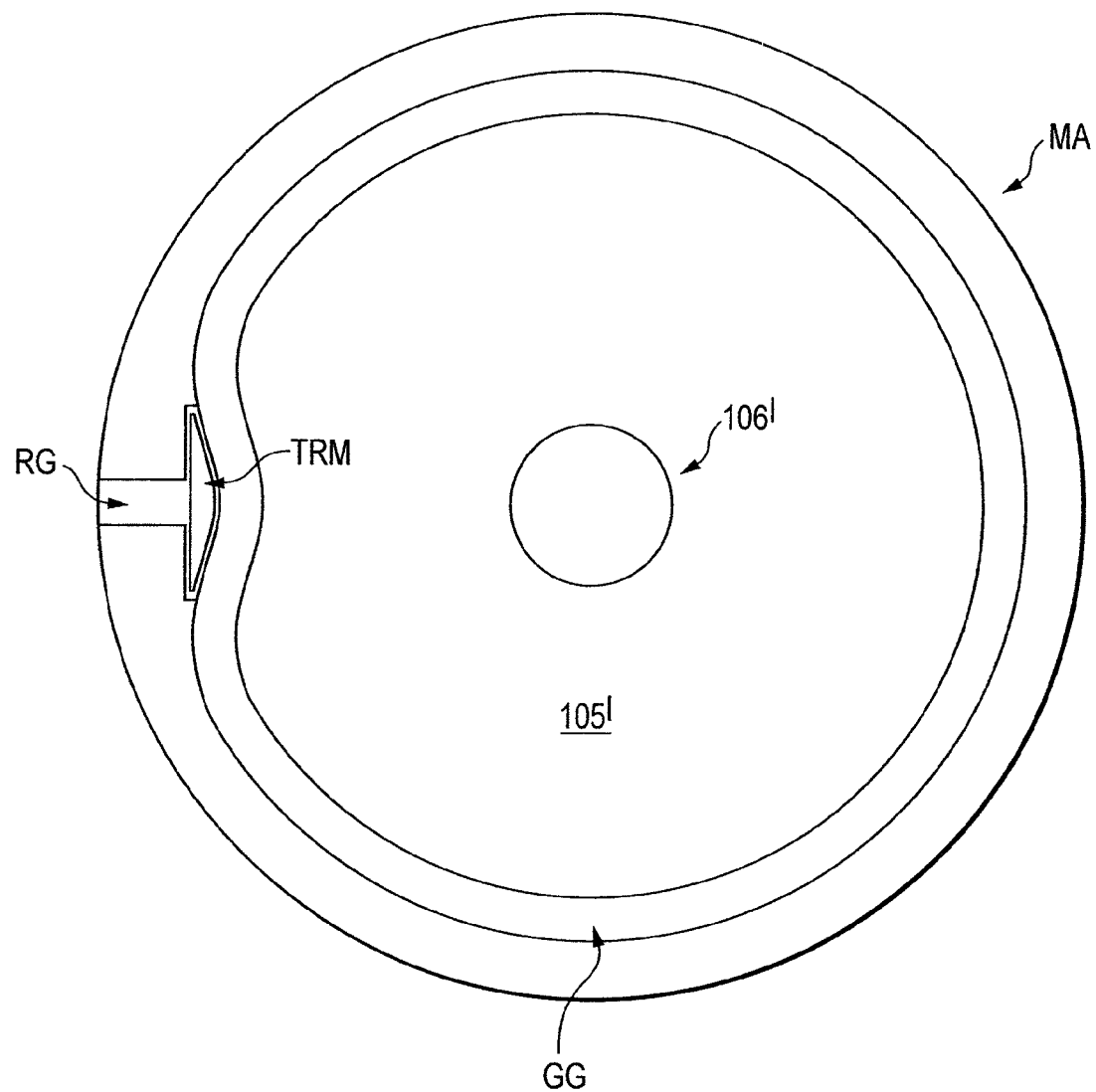
FIG. 49 shows a top view of the embodiment of the mounting arrangement of FIG. 48.

FIGS. 48 and 49 illustrate one non-limiting mounting arrangement MA by which one can mount the cartridge 10 to a testing device such as a glucose meter. The mounting arrangement MA can utilize a cartridge support surface 105' which is coupled to and/or formed integrally with a wall 100' of the testing device or the housing thereof. A hub member 106' extends from the support surface 105'. The hub 106' can be generally circular and can have an outer diameter which is slightly smaller than the central opening 40 of the cartridge 10. A guiding groove GG is formed in the surface 105'. The groove GG is designed to receive therein each of the projecting portions 50c of the lancet needles 50 when the cartridge 10 is located on the mounting arrangement MA. The projecting portions 50c move within the groove GG as the cartridge 10 rotates on the hub 106'. The mounting arrangement also includes trigger release mechanism TRM which is biased upwards by a spring. When the user desires to trigger one of the lancet needles 50 that is located in a pre-determined position, a trigger mechanism TM (see e.g., FIG. 56) can be activated so as to cause the trigger release mechanism TRM to move downwards against the biasing force of the spring. When the trigger release mechanism TRM reaches a lowered position (see FIG. 52), the lancet needle 50 will be free to move within the release groove RG under the biasing action/force of the spring 60b. Although not shown, the trigger release mechanism TRM can also be under the control of an actuating device such as a solenoid which can be electrically connected to the processor circuit of the testing device via wires and/or other types of electrical connections. Of course, the invention contemplates other non-electrical and/or mechanical devices for causing the release of the lancet needles 50 when a user desires to trigger one of them.

As explained above, the mounting arrangement MA can include an alignment projection (similar to mechanism 108 of FIG. 9) which extends from the outer cylindrical surface of the hub 106'. The projection has can have a triangular shape which corresponds to the shape of a notch (similar to notch 8 shown in FIG. 1) of the cartridge 10. Two spring biased electrical contact pins (similar to pins 103 and 104 of FIG. 9) can extend from the support surface 105'. As explained above, these pins provide electrical contact with the contacts 20b1 and 20b2 of each test strip 20b when the test strip 20b is located above the pin contacts. Although not shown, the contact pins can be connected to the processor of the testing device via wires or other electrical connections. A spring biased locking pin (similar to pin 101 in FIG. 9) can also extend from the support surface 105'. As explained above, this pin can engage the lower surface of the cartridge 10 until the opening 70 moves directly over the pin whereupon the pin will then protrude into the opening 70 so as to prevent further rotational movement of the cartridge 10. As can be seen in FIG. 49, the guiding groove GG is generally circular except for the region adjacent the trigger release mechanism. There, the groove GG has a concave or inwardly curved section so as to cause the spring 60b to become compressed and acquire potential energy. This way, when the trigger release mechanism TRM is lowered, the lancet needle 50 located that the position of the trigger release mechanism TRM, will be able to release its potential energy in the form of kinetic energy and will move to the extended puncturing position (see FIG. 52) under the action of the spring 60b.

Figure 50:
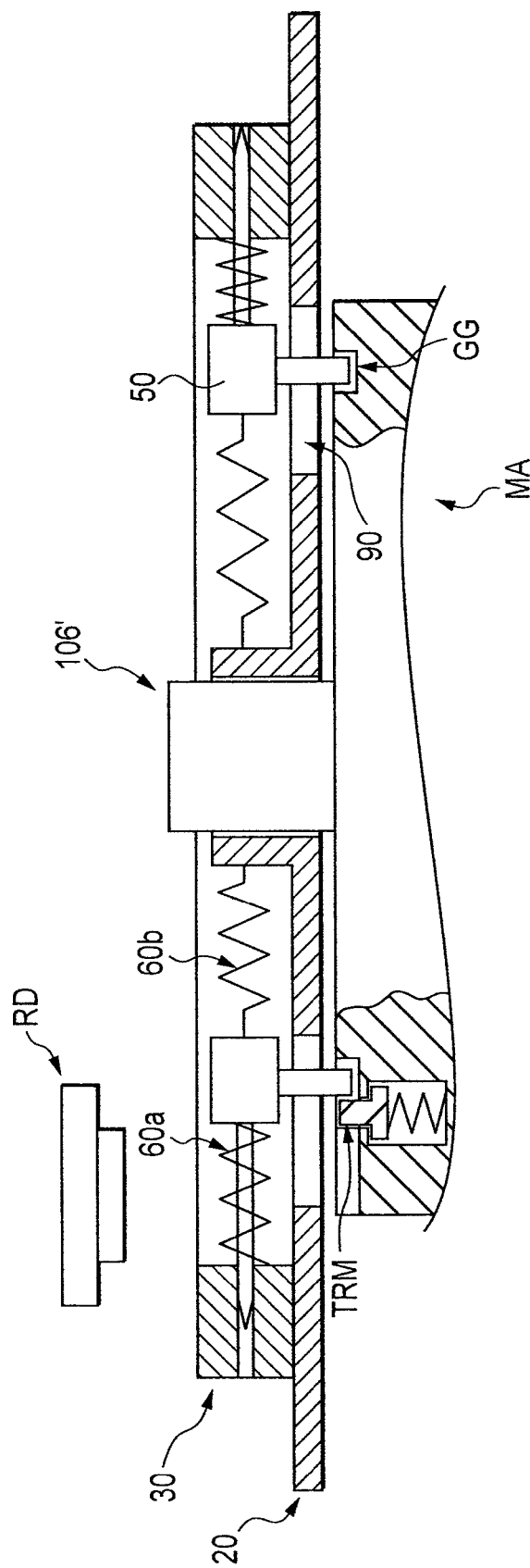
FIG. 50 shows a side cross-section view showing the cartridge of FIG. 39 installed on the mounting arrangement of FIG. 48. The figure shows the retaining device being lifted off of the cartridge after the cartridge has been installed on the mounting arrangement.
Figure 51:
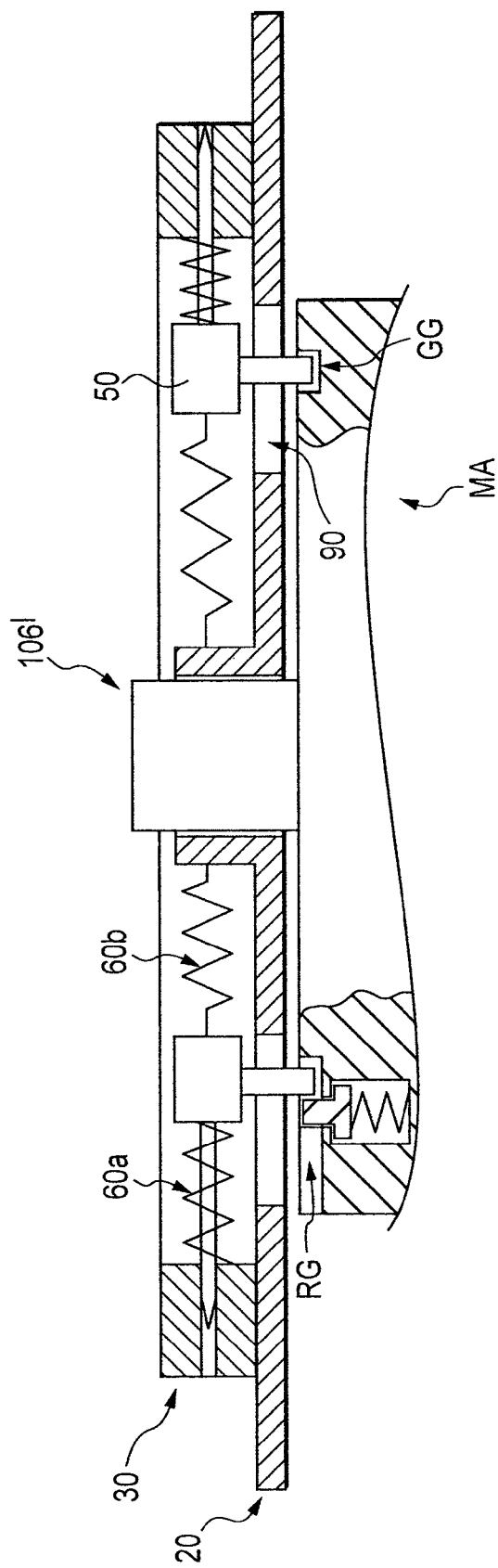
FIG. 51 shows a side cross-section view showing the cartridge of FIG. 39 installed on the mounting arrangement of FIG. 48. The retaining device has been completely removed from the cartridge after the cartridge has been installed on the mounting arrangement. The lancet needle located at the position of the trigger release mechanism is ready to move the extended position.

FIGS. 50-52 show the cartridge 10 mounted to the mounting arrangement MA shown in FIGS. 48-49. As can be seen in FIG. 50, the retaining device RD can be removed once the cartridge 10 is installed on the mounting arrangement MA. FIG. 51 shows the cartridge 10 installed on the mounting arrangement and illustrates that the lancet needle 50 located in the triggering position (left side) has been partially retracted so as to compress spring 60b. FIG. 52 shows how the lancet needle 50 has moved to the extended position after the trigger release mechanism TRM has experienced a downward force F. As can be seen in FIG. 52, the lancet needle 50 extends beyond an outer circumferential surface of the ring 30. This occurs by forcing the lancet needle 50 radially outwardly against the biasing force of the spring 60a. In this position, the needle would puncture a user's finger (see e.g., FIG. 22). Once retracted, the user can simple rotate the finger so that a drop of blood is placed onto the contacts of the test strip 20b which is positioned directly beneath the needle 50. Moreover, because the test strip 20b is positioned over the, contacts, the user will be able to determine a blood testing result from the testing device by placing a drop of blood onto the test strip 20b. The particular way in which the testing device or glucose meter determines the blood testing result from a blood sample placed on a test strip is conventional and is not discussed in detail herein.

Figure 64:
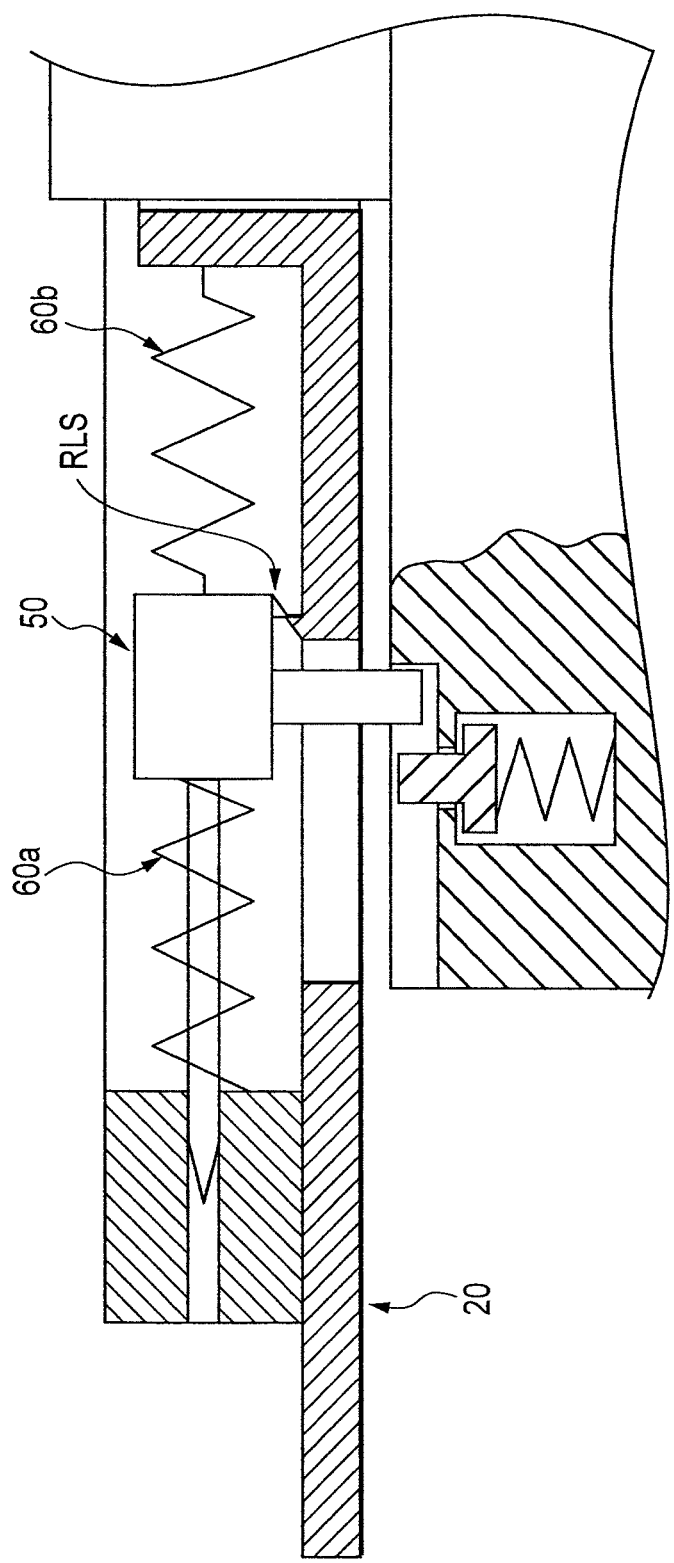
FIG. 64 shows a partial side cross-section view showing the cartridge of FIG. 39 installed on the mounting arrangement of FIG. 48 and illustrates one non-limiting retaining locking system which retains the lancet needles in a retracted position after the lancet needles have been triggered and used.

In order to ensure that the lancet needle 50 moves back to a position that allows the cartridge 10 to rotate on the mounting arrangement MA, each lancet needle 50 includes a projection which engages with a corresponding projection on the disk-shaped member 20 (see FIG. 64). The springs 60a and 60b are designed so that the lancet needle 50 is able to automatically move to the retracted position and locked position shown in FIG. 64 once they have reached the fully extended position. These cooperating projections constitute a retaining locking system RLS. Of course, the invention contemplates other ways which the lancet needles 50 can be secured in a retracted position once they are triggered in order to allow the cartridge 10 to rotate on the mounting arrangement MA while the projections 50c slide within the groove GG.

Figure 53:
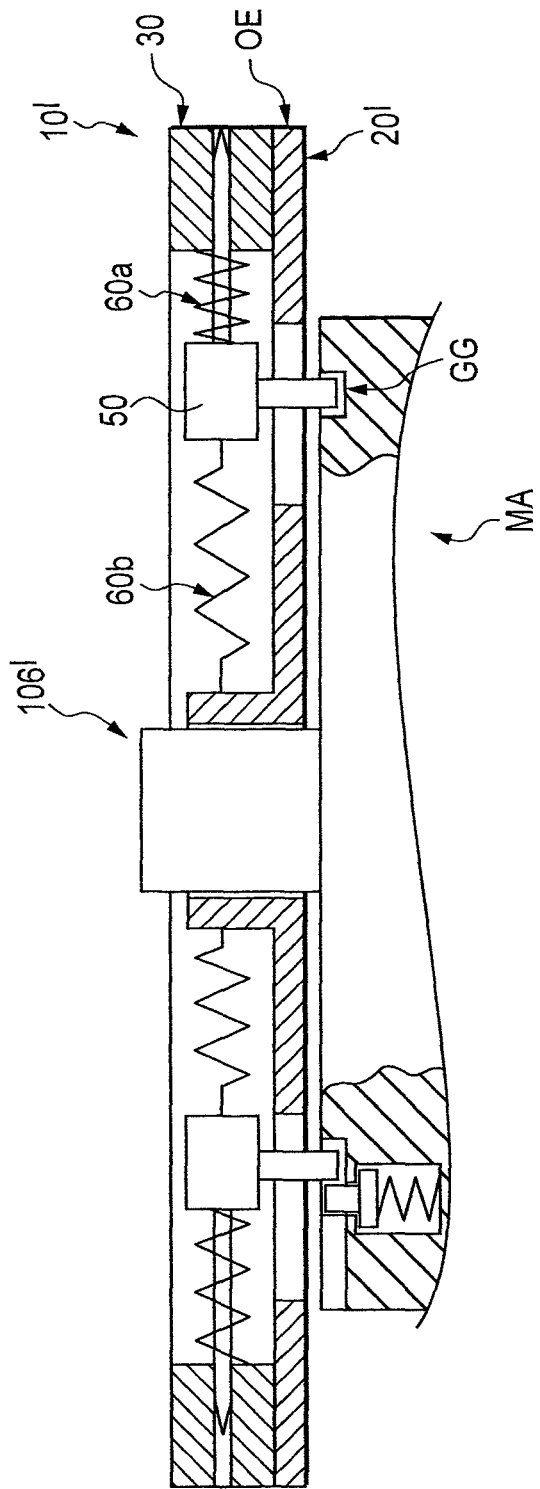
FIG. 53 shows a side cross-section view showing another embodiment of the cartridge installed on the mounting arrangement of FIG. 48. The retaining device has been completely removed from the cartridge after the cartridge has been installed on the mounting arrangement. The lancet needle located at the position of the trigger release mechanism is ready to move the extended position.
Figure 54:
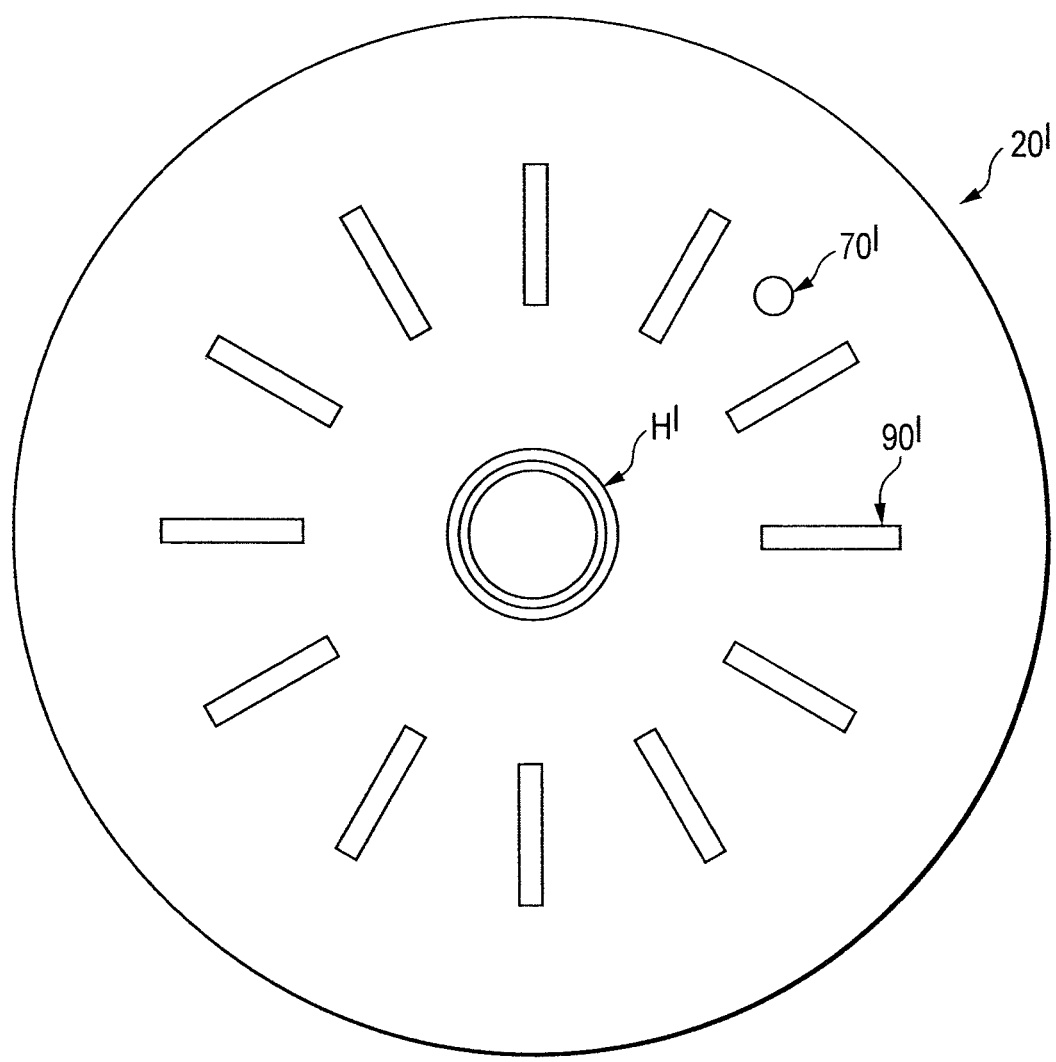
FIG. 54 shows a top view of the cartridge of FIG. 53 with the lancet needle support ring and the lancet needles removed therefrom.

FIGS. 53 and 54 show still another non-limiting embodiment of a cartridge 10'. The cartridge 10' includes a disk-shaped planar body 20' and a lancet needle retaining ring 30. Unlike the previous cartridge 10 embodiment, this cartridge 10' does not utilize test strips. Accordingly, the outer circumferential edge OE can be made with a smaller diameter which can correspond generally to the outer diameter of the ring 30. The cartridge 10' is otherwise similar to that of the cartridge 10 and includes the opening 70', the guide slots 90' and the hub H'. A plurality of lancet needles 50 are mounted to the ring 30 radially. Each lancet needle 50 has a cylindrical needle portion 50b, an enlarged head portion 50a, and a projecting portion 50c which can be engaged, contacted and/or movably guided by a mechanism (e.g., having the form of a guiding groove or recess) which causes the lancet needle 50 to extend beyond the ring 30 (see e.g., FIG. 52). Each lancet needle 50 is movably mounted within a radially oriented opening 30c formed in the ring 30. An inner spring 60b and an outer spring 60a is mounted to each lancet needle 50 in order to ensure that the lancet needle 50 automatically expands and retracts once the lancet needle 50 is triggered. Thus, spring 60b causes the lancet needle 50 to move to an extended puncturing position and spring 60a, which is substantially weaker than spring 60b, causes the lancet needle to move to a retracted or resting position after the lancet needle 50 reaches the fully extended position. Each lancet needle 50 is linearly guided by a slot 90 formed in the disk-shaped member 20. The internal stop surfaces of the slot 90 define the maximum extended position of the lancet needles 50 as well as the maximum retracted position of the lancet needles 50.

The operation of a testing device using a cartridge of the type shown in FIGS. 63 and 54 will now be explained. As an initial step, the user will open a door of the testing device and install the cartridge 10' onto the mounting arrangement, e.g., of the type shown in FIGS. 48 and 49. This is accomplished by aligning a notch of the disk-shaped member 20' with a projection of the hub 106'. The user can then force the cartridge 10' downwards until the bottom surface of the disk 20' contacts the surface 105'. The user can then close the door and begin using the device by switching on the testing device, placing a finger (see e.g., FNG shown in FIG. 22) and triggering the testing device to cause one of the lancet needles to puncture the finger. The user will then rotate the finger to place a blood drop on the exposed end of the test strip. The user will then place a drop of blood on a test strip (not shown) and place the test strip into the test device, as is conventionally known. Once the user has received a result, the user can then manually rotate the cartridge 10' by, e.g., applying a rubbing force on the edge OE, or as is preferred, by activating the indexing motor. This activation can occur automatically (i.e., after a time delay) or by, e.g., the user pressing the trigger button a third time. The device will then be ready for use again at a later time and/or by a different user.

Figure 55:
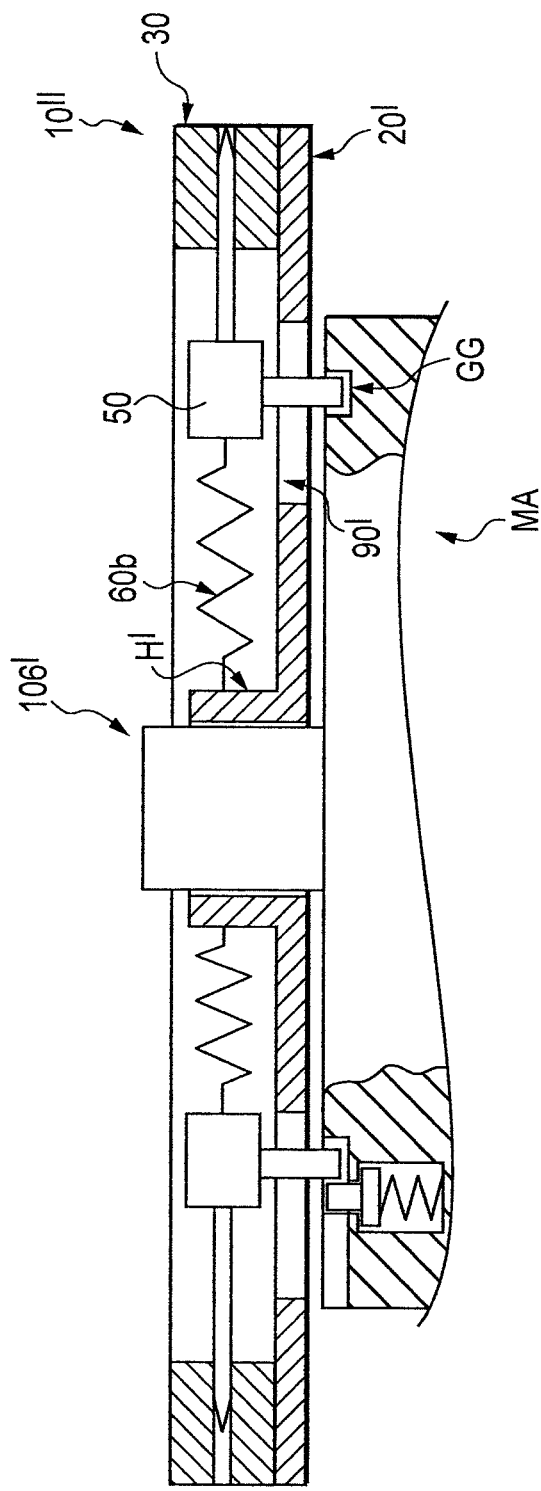
FIG. 55 shows a side cross-section view showing another embodiment of the cartridge installed on the mounting arrangement of FIG. 48. The cartridge is similar to that shown in FIG. 53 except that the retracting springs are not utilized on the lancet needles. The retaining device has been completely removed from the cartridge after the cartridge has been installed on the mounting arrangement. The lancet needle located at the position of the trigger release mechanism is ready to move the extended position.

FIG. 55 shows still another non-limiting embodiment of a cartridge 10". The cartridge 10" includes a disk-shaped planar body 20' and a lancet needle retaining ring 30 just like the cartridge shown in FIGS. 53 and 54. Unlike the previous cartridge 10' embodiment, this cartridge 10" does not utilize the outer retraction springs 60a and instead relies upon the inner springs 60b to provide for both the outward biasing force and the retracting force. The cartridge 10" is otherwise similar to that of the cartridge 10' and includes the opening 70', the guide slots 90' and the hub H'.

Figure 56:
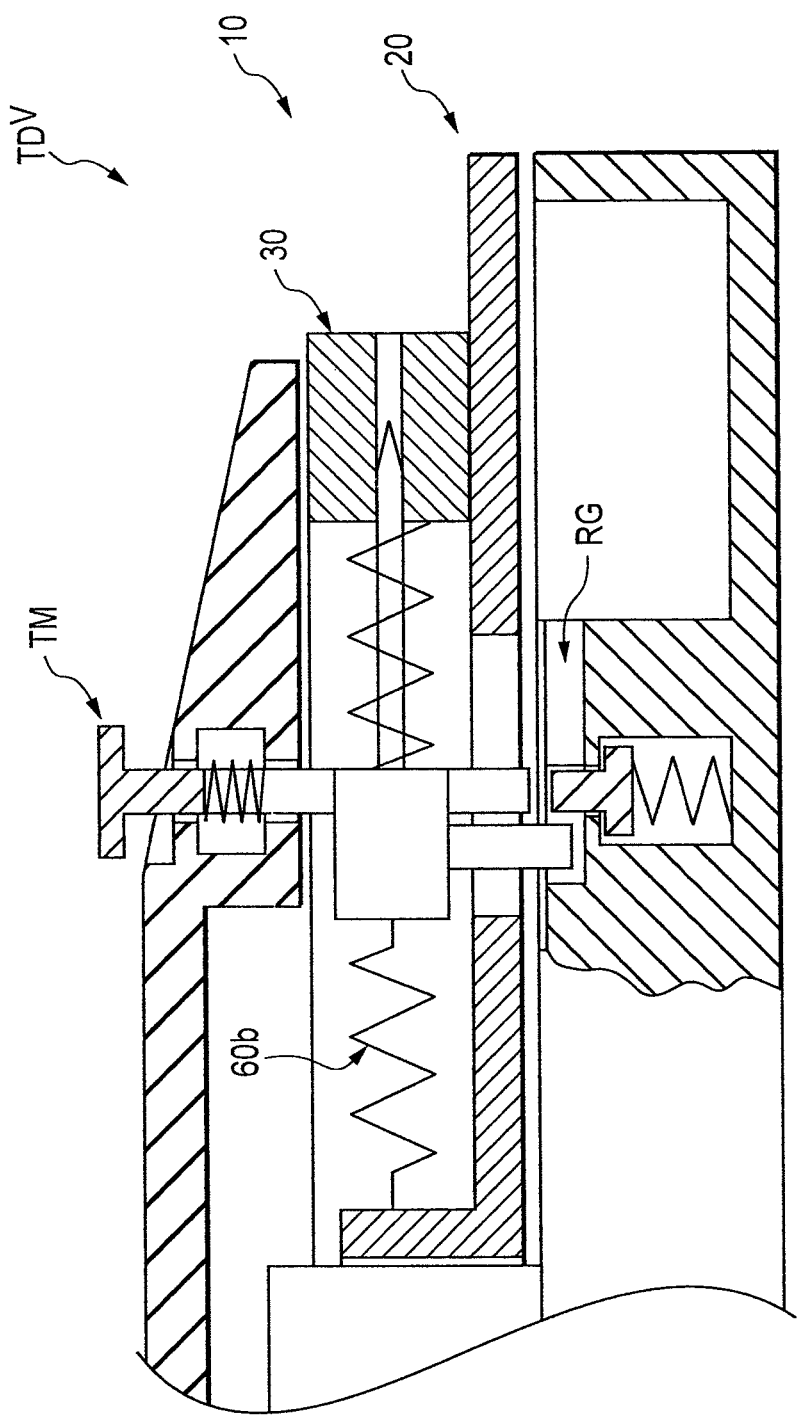
FIG. 56 shows a partial side cross-section view showing the cartridge of FIG. 39 installed on the mounting arrangement of FIG. 48, which is arranged on another embodiment of a testing device. The testing device is similar to that shown in FIG. 19 except for the mounting arrangement, which, in addition to including the contact pins and the location pin shown in FIG. 9, additionally utilizes a trigger release mechanism and a trigger mechanism arranged on the door.
Figure 57:
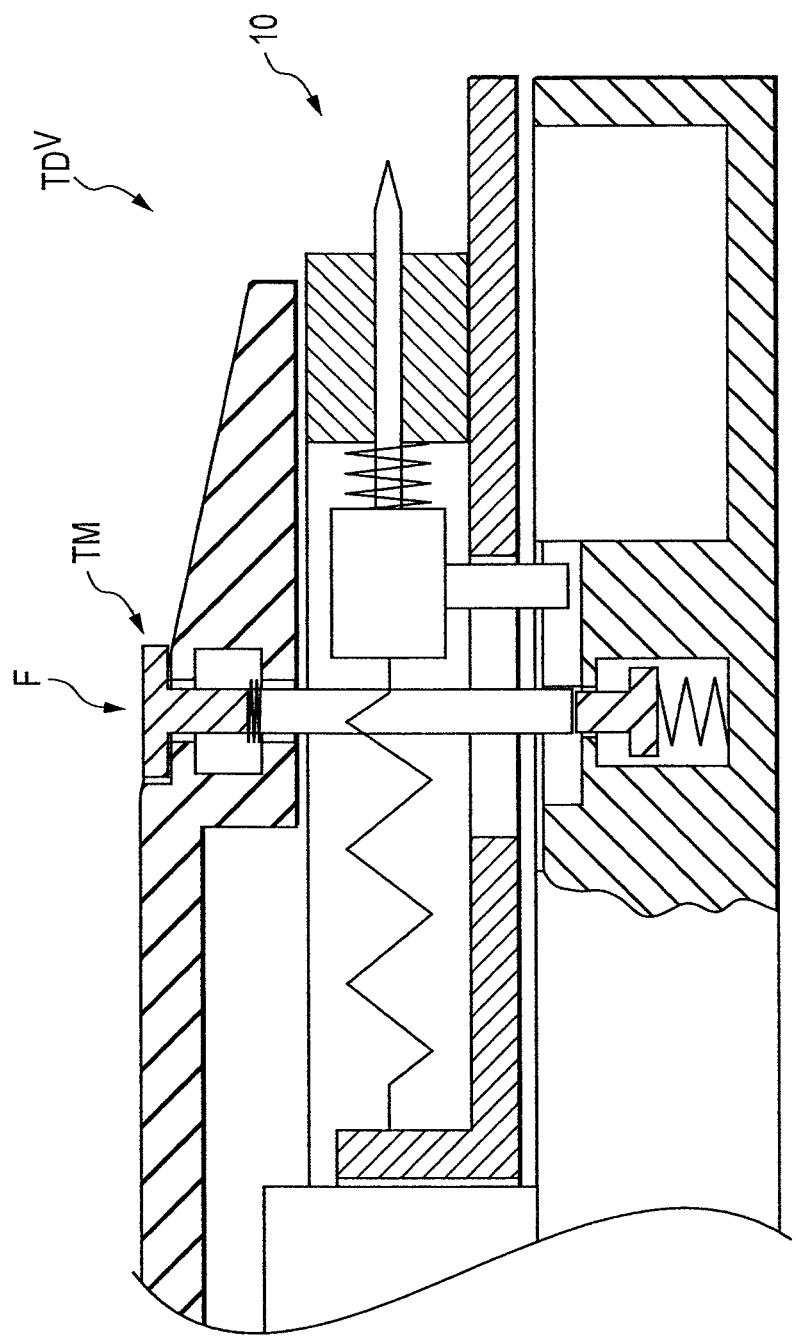
FIG. 57 shows the partial side cross-section view of FIG. 56 after the trigger mechanism has been triggered. The lancet needle is shown in the fully extended position.
Figure 58B:
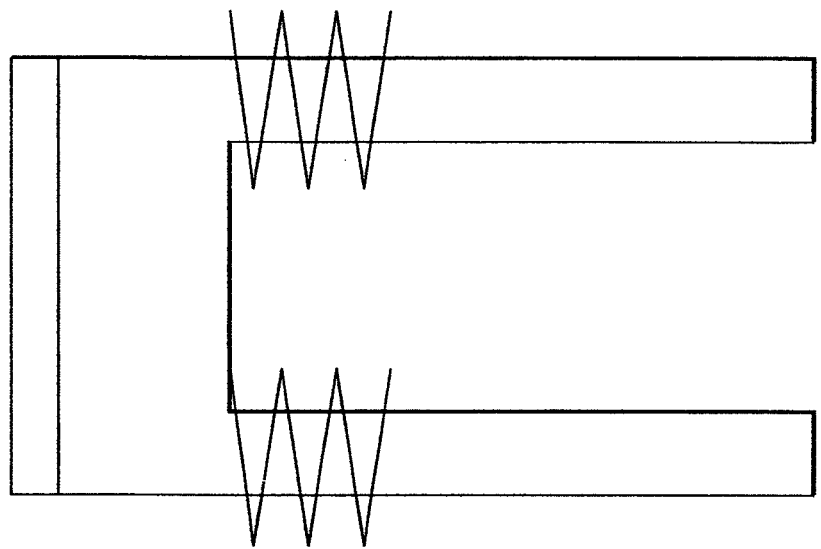
FIG. 58b shows a front view of the trigger mechanism shown in FIG. 58a with two springs installed on the two legs of the trigger mechanism.
Figure 58A:
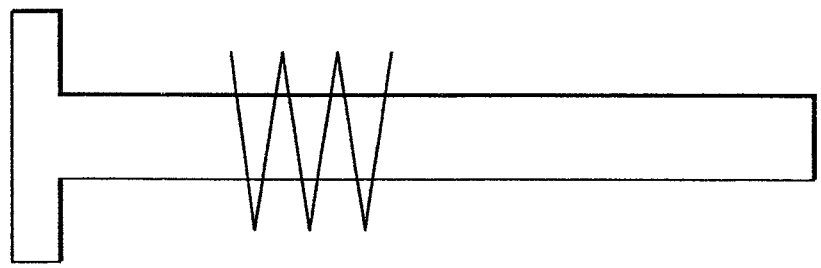
FIG. 58a shows a side view of the trigger mechanism shown in FIG. 56.

FIGS. 56-57 shows another non-limiting embodiment of a test device $TD^V$ which utilizes the cartridge 10 of FIGS. 39-46b. The test device $TD^V$ can be of the types shown in FIGS. 32-36 except that it includes the mounting arrangement shown in FIGS. 48-49 and a door which includes a movably mounted trigger mechanism TM. The trigger mechanism TM, which is shown in detail FIGS. 58a and 58b, includes two legs which contact an upper surface of the trigger release mechanism TRM when the trigger mechanism TM is pressed downwards or experiences a force F (see FIG. 57). As explained above, this allows the spring 60b to expand and cause movement of the lancet needled 50 towards the extended position, and allows for puncturing of a user's finger. To ensure that trigger mechanism TM is automatically moved back to the un-triggered position when it is not be depressed, springs mounted to the legs and are utilized to bias the trigger mechanism TM back upwards.

Figure 59:
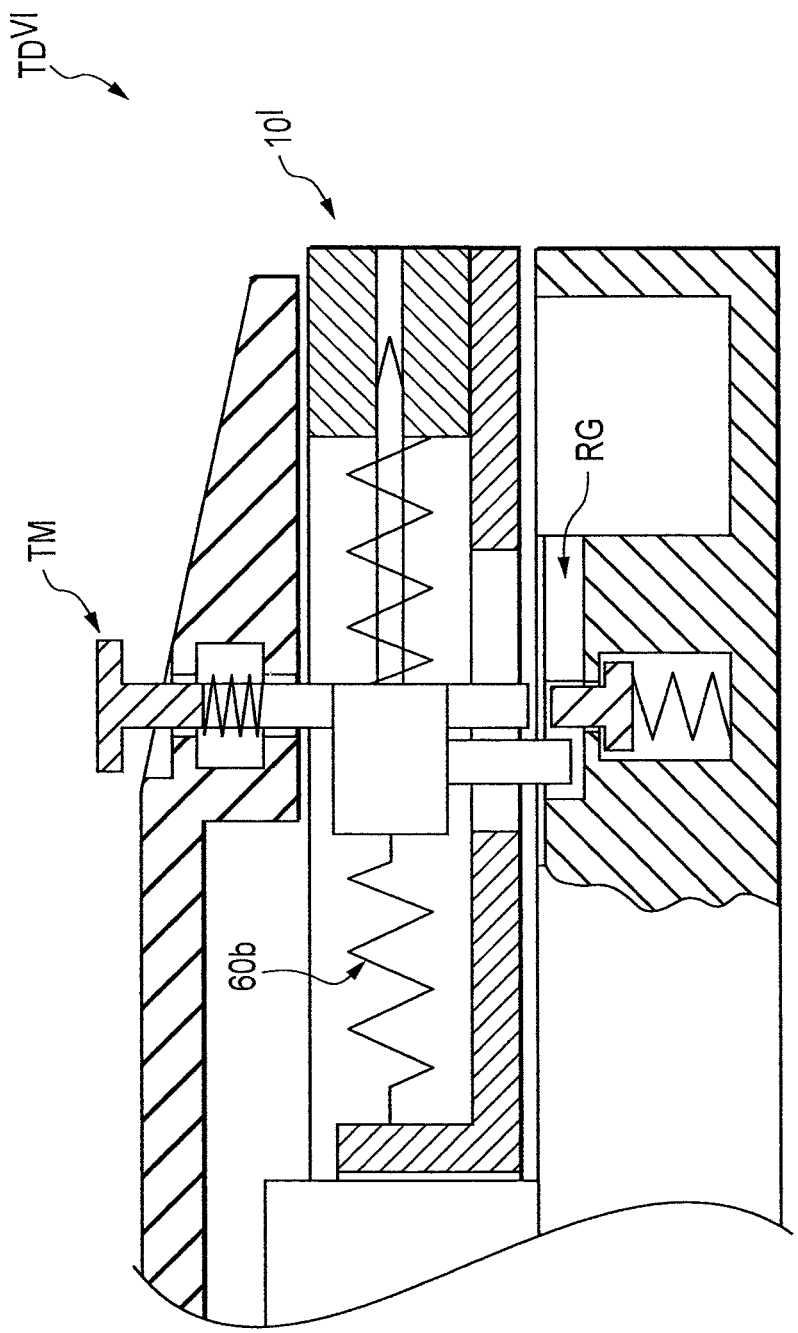
FIG. 59 shows a partial side cross-section view showing the cartridge of FIG. 53 installed on the mounting arrangement of FIG. 48, which is arranged on another embodiment of a testing device. The testing device is similar to that shown in FIG. 56 except that it has been modified to accommodate the cartridge which does not utilize test strips.

FIG. 59 shows another non-limiting embodiment of a test device $TD^{VI}$ which utilizes the cartridge 10' of FIGS. 53-54. The test device $TD^{VI}$ can also be of the types shown in FIGS. 32-36 except that it includes the mounting arrangement shown in FIGS. 48-49 and a door which includes a movably mounted trigger mechanism TM. The trigger mechanism TM, which is shown in detail FIGS. 58a and 58b, includes two legs which contact an upper surface of the trigger release mechanism TRM when the trigger mechanism TM is pressed downwards or experiences a force F (see e.g., FIG. 57). As explained above, this allows the spring 60b to expand and cause movement of the lancet needled 50 towards the extended position, and allows for puncturing of a user's finger. To ensure that trigger mechanism TM is automatically moved back to the un-triggered position when it is not be depressed, springs mounted to the legs and are utilized to bias the trigger mechanism TM back upwards.

Figure 60:
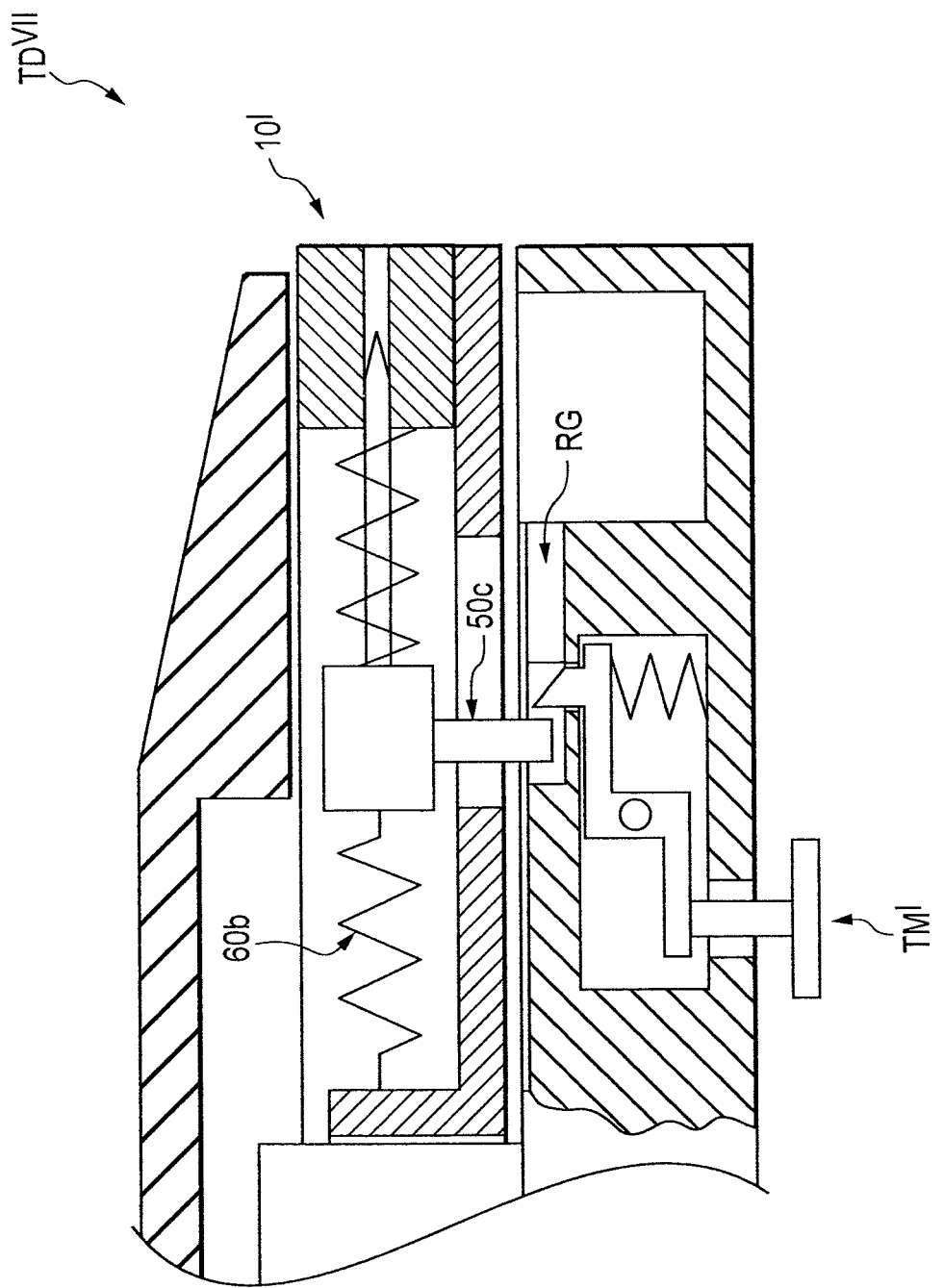
FIG. 60 shows a partial side cross-section view showing the cartridge of FIG. 53 installed on a mounting arrangement similar to that shown in FIG. 48, which is arranged on another embodiment of a testing device. The testing device is similar to that shown in FIG. 59 except that a trigger mechanism is arranged on the housing of the testing device rather than on the door.

FIG. 60 shows another non-limiting embodiment of a test device $TD^{VII}$ which utilizes the cartridge 10' of FIGS. 53-54. The test device $TD^{VII}$ can also be of the types shown in FIGS. 32-36 except that it includes a mounting arrangement similar to the one shown in FIGS. 48-49. The mounting arrangement and/or housing of the testing device $TD^{VII}$ of the instant embodiment is different in that it utilizes a trigger mechanism TM' to move a releasing projection instead of the trigger release mechanism TRM. This embodiment eliminates the need for a trigger mechanism that is mounted to the door of the test device as was the case in the embodiment shown in FIGS. 56-59. The trigger mechanism TM' functions as follows: when the trigger button is push towards the housing, the spring is compressed and the releasing projection pivots downwards. As a result, the releasing projection no longer prevents the projection 50c from moving. This allows the spring 60b to expand and cause movement of the lancet needled 50 towards the extended position, and allows for puncturing of a user's finger. To ensure that trigger mechanism TM' is automatically moved back to the un-triggered position when it is not be depressed, the spring biases the releasing projection of the trigger mechanism TM' upwards. The releasing projection also includes a tapered surface which can be engaged by the projection 50c so as to allow the lancet needle 50 to move back to a rest position after reaching the fully extended position.

Figure 61:
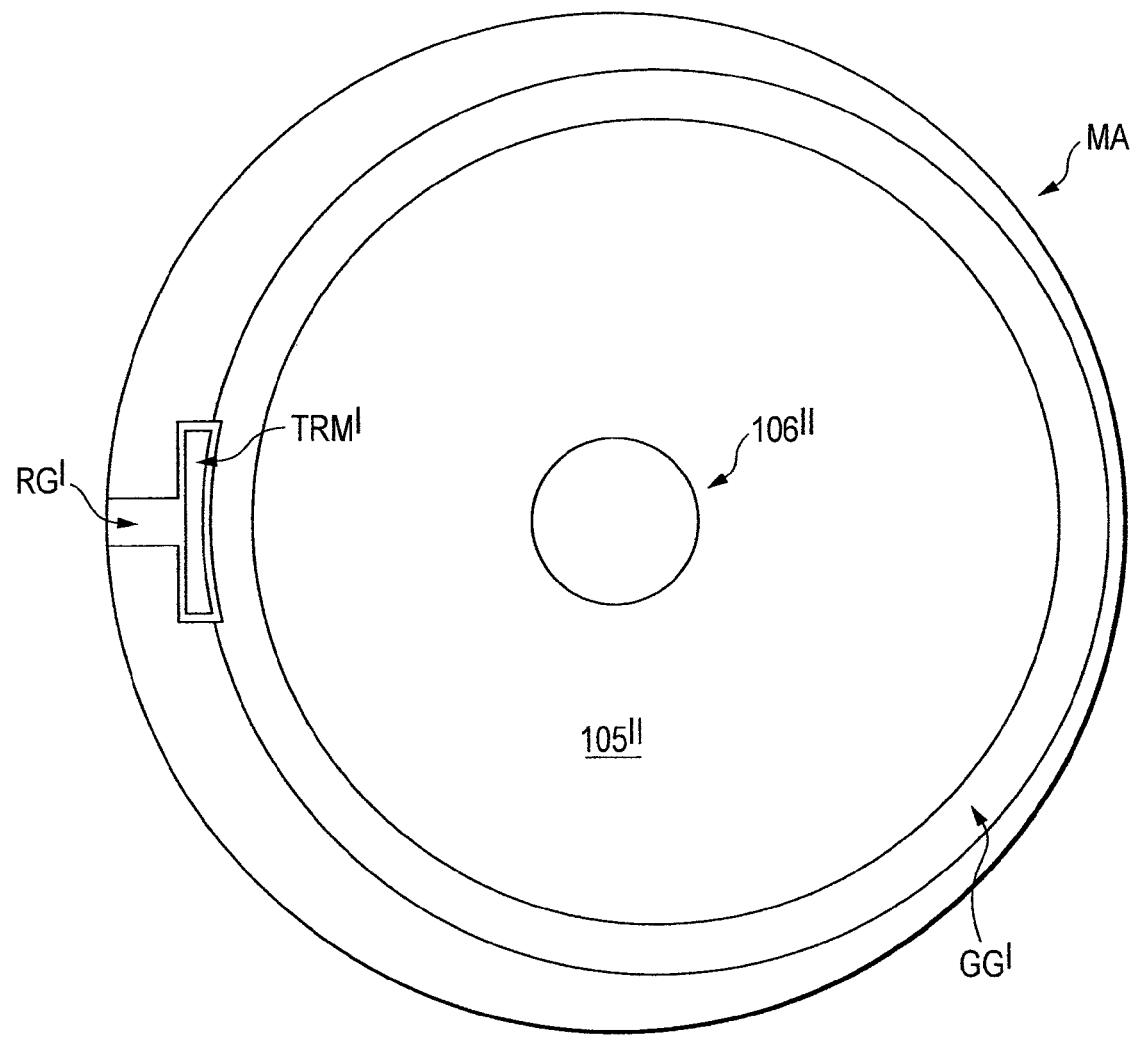
FIG. 61 shows a top view of another embodiment of the mounting arrangement. The mounting arrangement is similar to that shown in FIG. 49 except that an off-center circular guide groove is utilized and the trigger release mechanism has a different configuration.

FIG. 61 shows a top view of another embodiment of the mounting arrangement MA. The mounting arrangement MA utilizes a support surface 105" and is similar to that shown in FIGS. 48-49 except that an off-center circular guide groove GG' is utilized and the trigger release mechanism TRM' has a different configuration. As with the previous embodiment, a release groove RG' is utilized to ensure that the lancet needle 50 moves in a generally linear manner. As with the previous mounting arrangement, it can be used with the cartridges 10, 10' and 10" described above.

Figure 62:
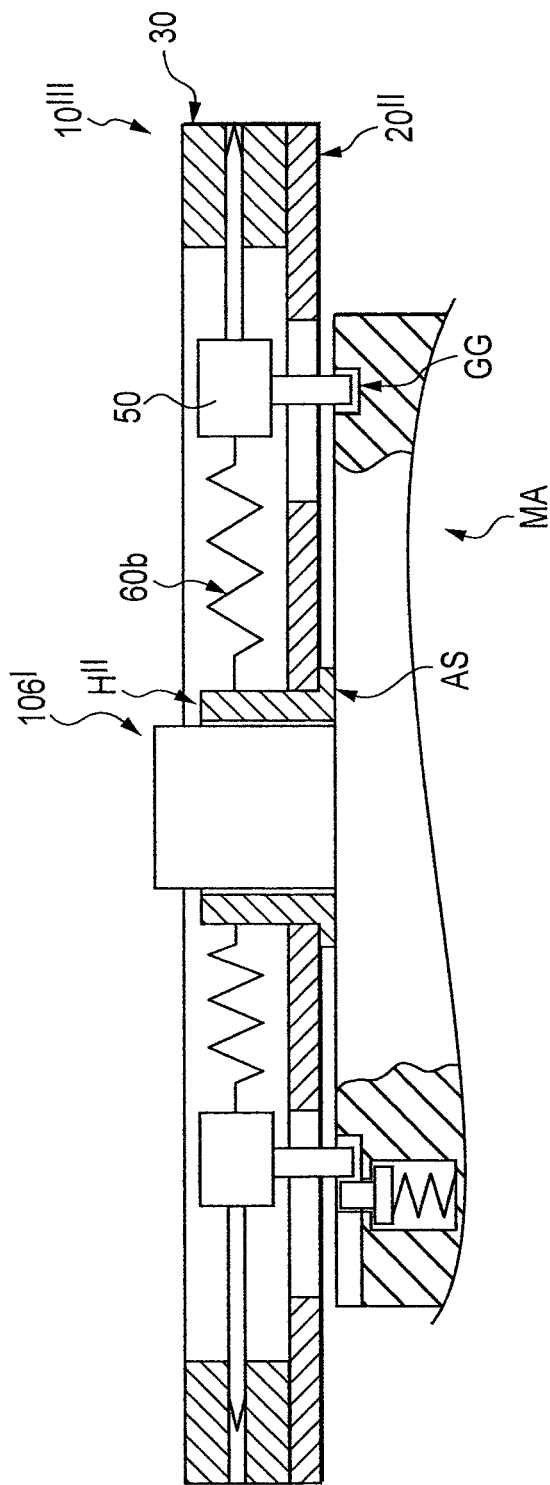
FIG. 62 shows a partial side cross-section view showing another embodiment of a cartridge. The cartridge is similar to the cartridge shown in FIG. 55 except that it utilizes a hub which is separate from the disk-shaped member. The cartridge is shown installed on the mounting arrangement of FIG. 48.

FIG. 62 shows a partial side cross-section view showing another embodiment of a cartridge 10'". The cartridge 10'" is similar to the cartridge shown in FIG. 55 except that it utilizes a hub H" which is separate from the disk-shaped member 20". By way of non-limiting example, the disk-shaped member 20" can be press fit onto the hub H" and the hub H" can formed without utilizing an annular support shoulder AS as shown in FIG. 62. The annular shoulder can alternatively be arranged on the opposite or upper surface of the disk-shaped member 20″. The cartridge 10′″ is shown installed on the mounting arrangement of FIG. 48.

Figure 63:
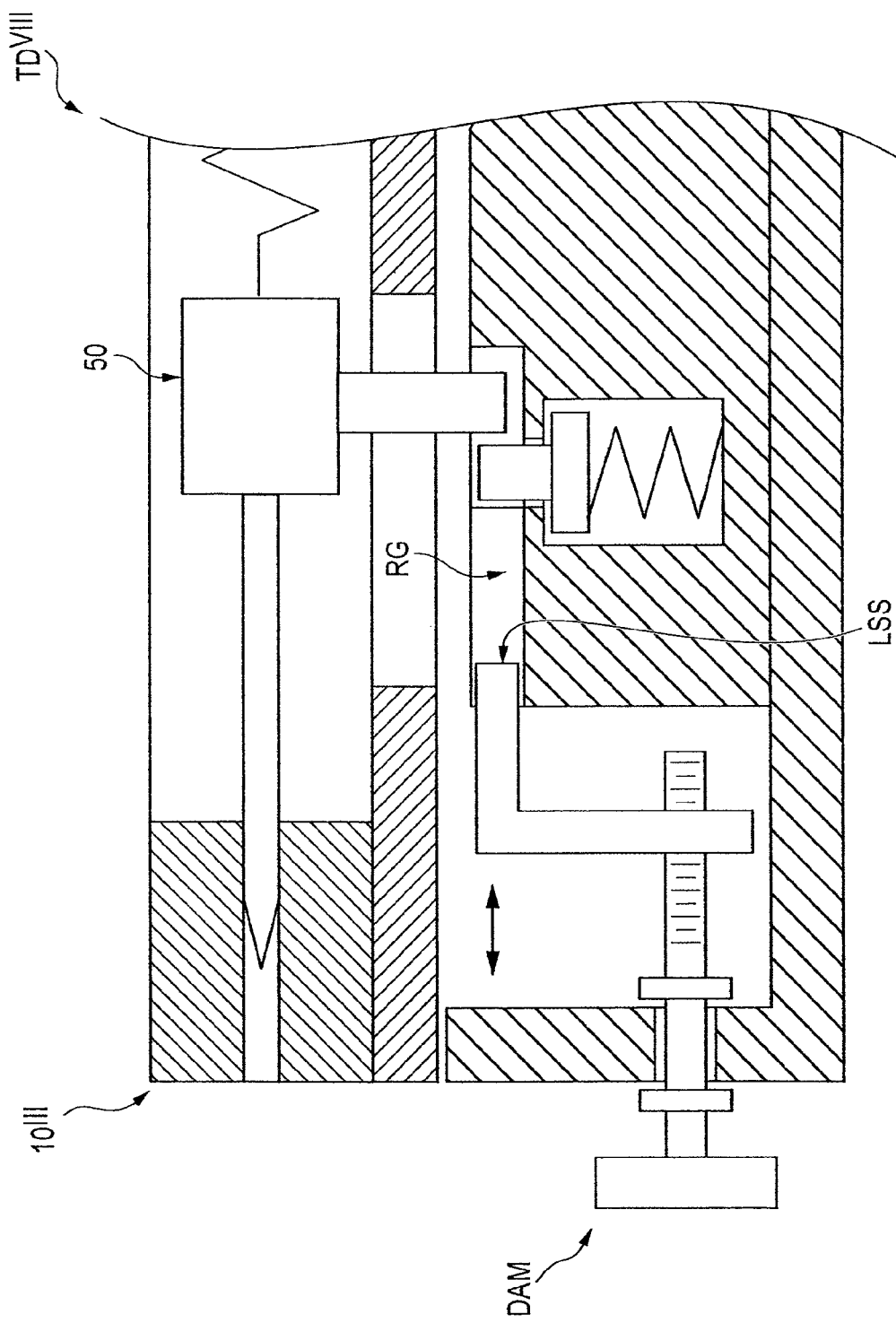
FIG. 63 shows a partial side cross-section view showing the cartridge of FIG. 62 installed on a mounting arrangement similar to that shown in FIG. 48, which is arranged on another embodiment of a testing device. The testing device is similar to that shown in FIG. 59 except that the testing device includes a mechanism for adjusting a depth of penetration of the lancet needles. The door and the trigger mechanism of the testing device are not shown.

FIG. 63 shows a partial side cross-section view showing the cartridge of FIG. 62 installed on a mounting arrangement similar to that shown in FIG. 48, which is arranged on another embodiment of a test device TD$^{VIII}$. The test device TD$^{VIII}$ is similar to that shown in FIG. 59 except that it includes a mechanism DAM for adjusting a depth of penetration of the lancet needles. The mechanism DAM utilizes a dial which rotates a threaded member. An L-shaped member is threadably mounted to the threaded member and has a stop surface LSS which projects into the release groove RG. When the user wishes to adjust a depth of penetration of the lancet needles, the user simply rotates the dial in either direction to cause the stop surface LSS to move forwards and backwards as indicated by the arrows. The invention contemplates that this depth setting arrangement can be used on any of the test devices disclosed herein. The door and the trigger mechanism of the testing device TD$^{VIII}$ are not shown.

FIG. 64 shows a partial side cross-section view showing the cartridge of FIG. 39 installed on the mounting arrangement of FIG. 48 and illustrates one non-limiting way in which the lancet needles 50 can be retained in a retracted position after being moved to the fully extended position. In this embodiment, a retaining locking system RLS having the form of tapered projections retains each lancet needle 50 in a retracted position after the lancet needles have been triggered and used. Such a retention system ensures that the lancet needles 50 remain engages with the guiding groove GG after they are triggered.

Figure 65:
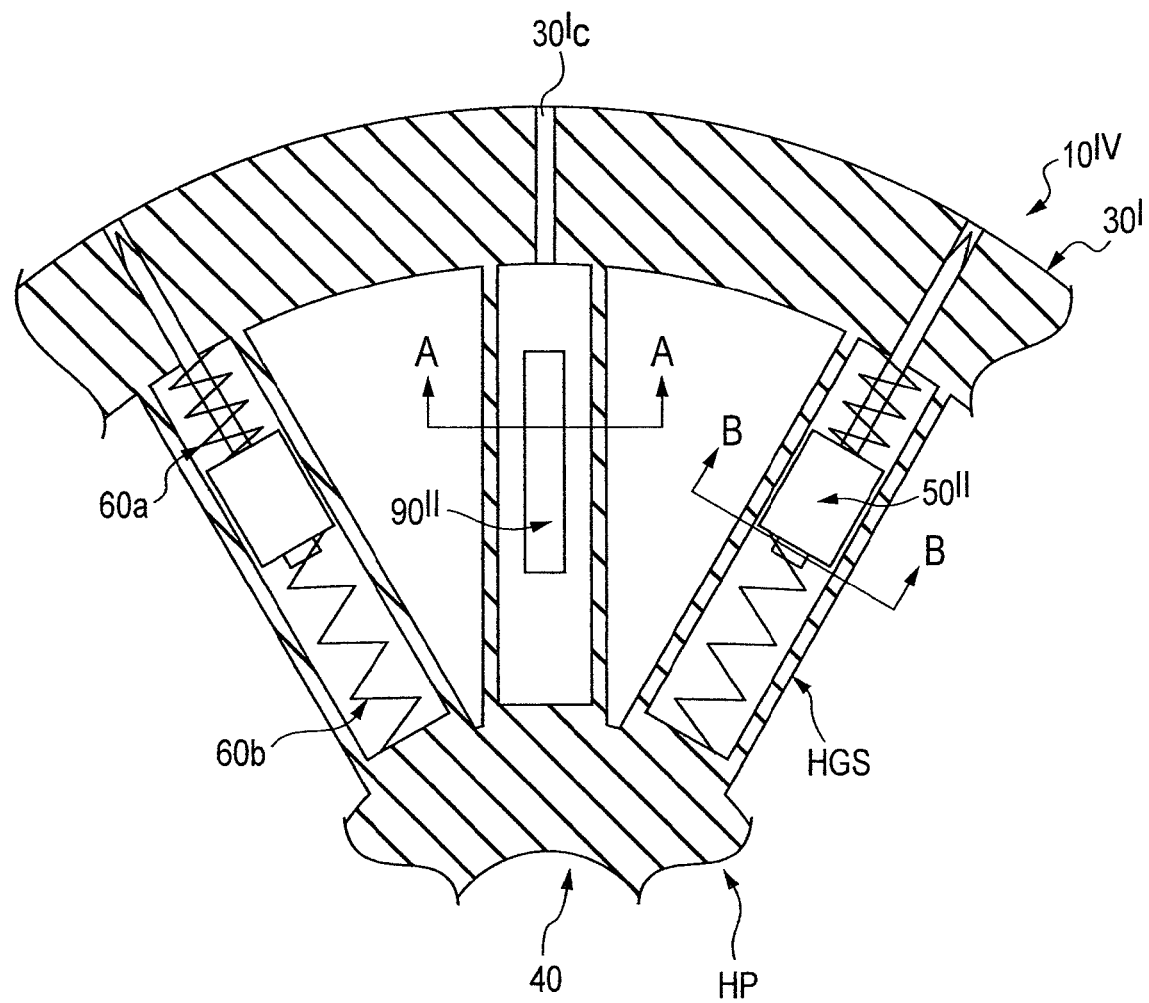
FIG. 65 shows a partial top cross-section view showing another non-limiting embodiment of a cartridge. The cartridge comprises a one-piece member which includes both the ring, lancet needle guiding spokes and a hub portion having a central opening.
Figure 66B:
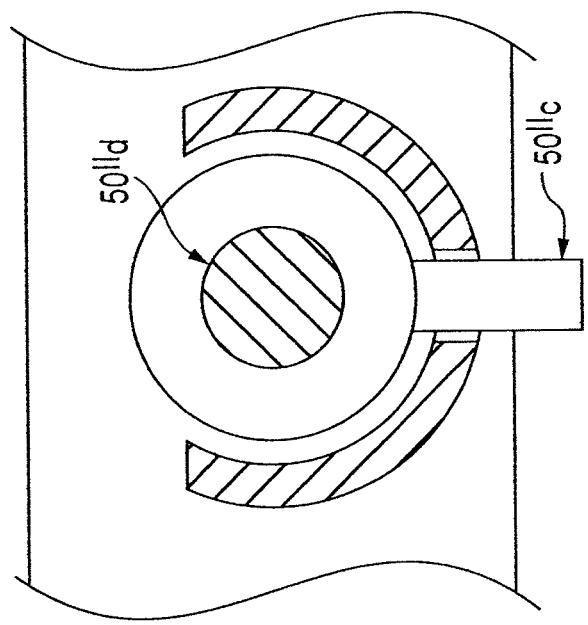
FIG. 66b shows a partial cross-section view through arrows B-B in FIG. 65.
Figure 66A:
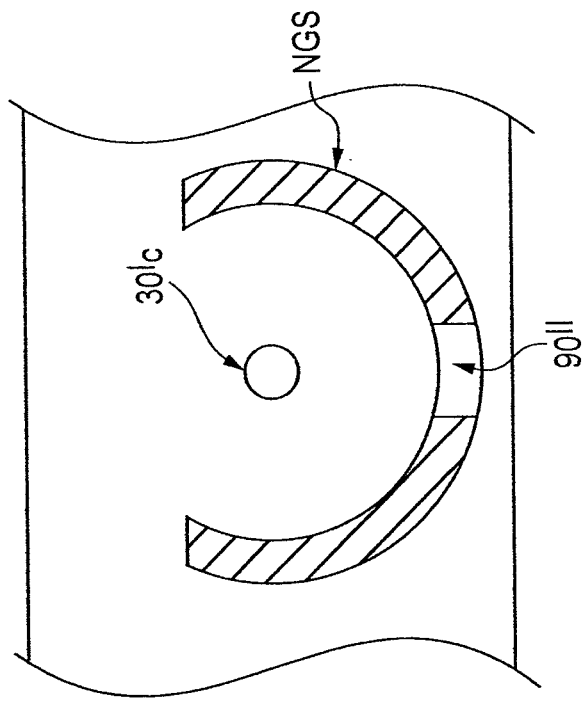
FIG. 66a shows a partial cross-section view through arrows A-A in FIG. 65.

FIGS. 65-66b show another non-limiting embodiment of a cartridge 10$^{IV}$. The spoke in the center is shown with the lancet needle and springs removed. The cartridge 10$^{IV}$ comprises a one-piece member which includes both the ring portion 30′, partially hollow lancet needle guiding spokes NGS, and a hub portion HP which has a central opening 40. The one-piece member can be made of synthetic resin. Each spoke NGS includes a guiding slot 90″ and houses both a lancet needle 50″ and the springs 60a and 60b. As can be seen in FIG. 66a, the spoke NGS has a generally cylindrical configuration which is open to allow insertion of the lancet needle 50″ and springs 60a and 60b. To ensure that the spring 60b remains in the channel formed by the spoke NGS, the lancet needle 50″ includes a centrally disposed rear projection 50″d.

The testing devices can preferably made transparent and/or translucent so that a user will clearly be able to identify when and how much of the cartridge has already been utilized. Of course, the invention is not limited to a body design which is transparent and/or translucent.

It is also possible to provide a number or letter (or other indicia) on each test strip and/or each lancet needle location of the cartridge so that a user will be able to see which test strip or lancet needle is being utilized and how many remain for use. The testing device can also be provided with a system which senses the position of the cartridge and indicates the position number digitally. By way of non-limiting example, this can be accomplished using a bar-code reader system. All the parts of the cartridge, with the exception of the springs and needles (which can respectively be made of spring steel and stainless steel), may be made from plastic materials and can be formed using conventional injection molding techniques or other known manufacturing methods. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A combination of a cartridge and a testing device, the combination comprising:
    a cartridge comprising:
        a plurality of lancet needles movably mounted to a disk-shaped body;
        a plurality of test strips arranged on the disk-shaped body; and
        a mechanism allowing the cartridge to be mounted to the testing device,
    wherein, when installed in the testing device, the cartridge is sized and configured to extend outside of a body of the testing device such that an outer peripheral portion of the cartridge and portions of electrical contacts of the test strips exposable to a user's blood drop are visible and accessible while the testing device is resting on a horizontal surface, such that the portions of the electrical contacts exposed to a user's blood drop extend into a testing area and are visible and accessible to a user from a position above the testing device,
    wherein each of the plurality of lancet needles is generally radially oriented and moves along a generally linear path, and
    wherein each of the plurality of test strips is generally radially oriented.

2. The combination of claim 1, wherein the mechanism allowing the cartridge to be mounted to the testing device comprises an opening.

3. The combination of claim 1, wherein each of the plurality of lancet needles moves along a generally linear path without rotating.

4. The combination of claim 1, further comprising a plurality of springs, each spring having one end coupled to one of the plurality of lancet needles.

5. The combination of claim 1, wherein the cartridge comprises a generally circular shape.

6. The combination of claim 1, wherein the cartridge comprises a generally circular shape having an outer diameter of no greater than about 2 inches.

7. The combination of claim 1, wherein the cartridge comprises a generally circular shape having a thickness of no greater than about 0.25 inches.

8. The combination of claim 1, further comprising a ring-shaped member, wherein each of the plurality of lancet needles is movably mounted to the ring-shaped member.

9. The cartridge of claim 1, wherein the plurality of test strips are non-movably mounted to an upper surface of the disk-shaped body.

10. The cartridge of claim 1, wherein the disk-shaped body comprises a thickness of less than about 0.10 inches.

11. A method of puncturing a surface of skin using the combination of claim 1, the method comprising:
   installing the cartridge on the testing device;
   placing a finger of a user on a portion of the outer peripheral portion of the cartridge;
   triggering the testing device so that one of the plurality of lancet needles is caused to penetrate the user's skin; and
   rotating the cartridge to another position.

12. A combination comprising:
   a cartridge comprising a planar disk-shaped body, a plurality of radially oriented lancet needles mounted to a member that is fixed to an upper surface of the disk-shaped body, a plurality of test strips arranged on the upper surface of the disk-shaped body, and a plurality of springs;
   each spring being structured and arranged to at least one of:
      move one of the plurality of lancet needles towards an extended position; and
      move one of the plurality of lancet needles towards a retracted position; a testing device,
   wherein the cartridge is structured and arranged to be removably mountable to the testing device, and
   wherein, when installed in the testing device, the cartridge is sized and configured to extend outside of a body of the test device such that an outer peripheral portion of the cartridge and portions of electrical contacts of the test strips exposable to a user's blood drop are visible and accessible while the testing device is resting on a horizontal surface, such that the portions of the electrical contacts exposed to a user's blood drop extend into a testing area and are visible and accessible to a user from a position above the testing device.

13. The combination of claim 12, wherein the planar disk-shaped body comprises a center opening and a plurality of radially oriented guide slots, wherein the plurality of radially oriented lancet needles are movable along a generally linear path without substantially rotating, and wherein the center opening allows the cartridge to be removably mounted to the test device.

14. A method of puncturing a surface of skin using the combination of claim 12, the method comprising:
   installing the cartridge on the testing device;
   placing a finger of a user on a portion of the outer peripheral portion of the cartridge;
   triggering the testing device so that one of the plurality of lancet needles is caused to penetrate the user's skin; and
   rotating the cartridge to another position.

15. A testing device comprising:
   a housing; and
   a cartridge comprising:
      a plurality of lancet needles radially oriented and movably mounted to one side of a disk-shaped body;
      the body having test strips integrally formed therein; and
      a plurality of springs,
   wherein the cartridge is movably mounted within the housing, and
   wherein, when installed in the housing, the cartridge is sized and configured to extend outside of a body of the housing such that an outer peripheral portion of the cartridge and portions of electrical contacts of the test strips exposable to a user's blood drop are visible and accessible while the housing is resting on a horizontal surface, such that the portions of the electrical contacts exposed to a user's blood drop extend into a testing area and are visible and accessible to a user from a position above the housing.

16. The testing device of claim 15, wherein the cartridge is generally disk-shaped and comprises a center opening which is rotatably mounted about a hub arranged within the housing.

17. The testing device of claim 15, wherein the plurality of lancet needles are movably mounted to a member that is fixed to the disk-shaped body.

18. The testing device of claim 15, wherein the cartridge is removably mounted to the housing.

19. The testing device of claim 15, wherein the housing comprises a door which can be opened to remove the cartridge.

20. A glucose meter comprising:
   a housing;
   a cartridge comprising a plurality of lancet needles radially oriented and movably mounted to one side of a disk-shaped body having test strips integrally formed therein and slots;
   a plurality of radially movable projecting portions extending through the slots in the disk-shaped body so as to extend to an opposite side of the disk-shaped body, each projecting portion being movable with one of the lancet needles;
   the cartridge being movably and removably mounted within the housing;
   a mechanism which retains the cartridge in at least one rotational position; and
   a device which allows a user to rotate the cartridge between a plurality of positions,
   wherein, when installed in the housing, the cartridge is sized and configured to extend outside of a body of the housing such that an outer peripheral portion of the cartridge and portions of electrical contacts of the test strips exposable to a user's blood drop are visible and accessible while the housing is resting on a horizontal surface, such that the portions of the electrical contacts exposed to a user's blood drop extend into a testing area and are visible and accessible to a user from a position above the housing.

21. The glucose meter of claim 20, wherein the housing comprises a door which can be opened to remove the cartridge.

22. The glucose meter of claim 20, wherein the mechanism which retains the cartridge in at least one rotational position comprises a deflecting member.

23. The glucose meter of claim 20, wherein the device which allows a user to rotate the cartridge between a plurality of positions comprises a motor.

24. The glucose meter of claim 20, further comprising an alignment mechanism allowing the cartridge to be initially mounted within the housing in only a single position.

25. The glucose meter of claim 20, further comprising one of a notch and a groove which ensures that the cartridge is mounted to the housing in a predetermined position.

26. The glucose meter of claim 20, further comprising a locking mechanism preventing rotation of the cartridge once the cartridge has rotated in the housing to a locking position.

27. A method of puncturing a surface of skin using the glucose meter of claim 20, the method comprising:
   installing the cartridge on the housing;
   placing a finger of a user on a portion of the outer peripheral portion of the cartridge;
   triggering the glucose meter so that one of the plurality of lancet needles is caused to penetrate the user's skin; and
   rotating the cartridge to another position.

* * * * *